(12) United States Patent
Campisi et al.

(10) Patent No.: US 9,901,081 B2
(45) Date of Patent: *Feb. 27, 2018

(54) TRANSGENIC MOUSE FOR DETERMINING THE ROLE OF SENESCENT CELLS IN CANCER

(71) Applicants: Buck Institute for Research on Aging, Novato, CA (US); Erasmus University Medical Center Rotterdam, Rotterdam OT (NL); James Mitchell, Boston, MA (US); Wendy Toussaint, Ghent (BE)

(72) Inventors: Judith Campisi, Berkeley, CA (US); Marco Demaria, Groningen (NL); Francis Rodier, Novato, CA (US); Remi-Martin Laberge, San Francisco, CA (US); James Mitchell, Boston, MA (US); Jan H. J. Hoeijmakers, Rotterdam (NL); Wendy Toussaint, Ghent (BE)

(73) Assignees: Buck Institute for Research on Aging, Novato, CA (US); Erasmus University Medical Center Rotterdam, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,991

(22) Filed: Mar. 25, 2016

(65) Prior Publication Data

US 2017/0042129 A1  Feb. 16, 2017

Related U.S. Application Data

(63) Continuation of application No. 13/975,217, filed on Aug. 23, 2013, now abandoned.

(60) Provisional application No. 61/837,090, filed on Jun. 19, 2013, provisional application No. 61/692,622, filed on Aug. 23, 2012.

(51) Int. Cl.
| | |
|---|---|
| *A01K 67/027* | (2006.01) |
| *A61K 49/00* | (2006.01) |
| *C12N 15/85* | (2006.01) |
| *C12N 9/50* | (2006.01) |
| *G01N 33/50* | (2006.01) |

(52) U.S. Cl.
CPC ...... *A01K 67/0275* (2013.01); *A61K 49/0008* (2013.01); *C12N 9/50* (2013.01); *C12N 15/8509* (2013.01); *G01N 33/5011* (2013.01); *G01N 33/5088* (2013.01); *A01K 2217/206* (2013.01); *A01K 2227/105* (2013.01); *A01K 2267/0331* (2013.01); *A01K 2267/0393* (2013.01); *C07K 2319/70* (2013.01); *C12N 2015/8572* (2013.01)

(58) Field of Classification Search
CPC ............ A01K 67/025; A01K 2227/105; A01K 2267/03; A01K 2267/0373; C12N 15/8509; C12N 2015/8527; C12N 2830/008
USPC ................................. 800/18, 3, 10; 435/325
See application file for complete search history.

(56) References Cited

U.S. PATENT DOCUMENTS

| | | |
|---|---|---|
| 4,873,191 A | 10/1989 | Wagner et al. |
| 6,201,020 B1 | 3/2001 | Zhang et al. |
| 7,390,799 B2 | 6/2008 | Bruncko et al. |
| 7,642,260 B2 | 1/2010 | Bruncko et al. |
| 7,767,684 B2 | 8/2010 | Bruncko et al. |
| 7,829,556 B2 | 11/2010 | Bemis et al. |
| 7,842,681 B2 | 11/2010 | Elmore et al. |
| 7,851,626 B2 | 12/2010 | Ding et al. |
| 7,879,857 B2 | 2/2011 | Mabire et al. |
| 7,928,104 B2 | 4/2011 | Mabire et al. |
| 7,973,161 B2 | 7/2011 | Bruncko et al. |
| 8,071,623 B2 | 12/2011 | Jones et al. |
| 8,168,645 B2 | 5/2012 | Baell et al. |
| 8,343,967 B2 | 1/2013 | Ding et al. |
| 8,426,422 B2 | 4/2013 | Hexamer et al. |
| 8,518,970 B2 | 8/2013 | Baell et al. |
| 8,541,417 B2 | 9/2013 | Brown et al. |
| 8,557,983 B2 | 10/2013 | Bruncko et al. |
| 8,563,735 B2 | 10/2013 | Bruncko et al. |
| 8,586,754 B2 | 11/2013 | Bruncko et al. |
| 8,614,318 B2 | 12/2013 | Bruncko et al. |
| 8,624,027 B2 | 1/2014 | Shah et al. |
| 2004/0006233 A1 | 1/2004 | Holt et al. |
| 2004/0180430 A1 | 9/2004 | West et al. |

(Continued)

FOREIGN PATENT DOCUMENTS

| | | |
|---|---|---|
| WO | WO-03028443 A1 | 4/2003 |
| WO | WO-2006018632 A2 | 2/2006 |

(Continued)

OTHER PUBLICATIONS

Robson et al. (2003) J. Biomed. Biotech., 2003:2, 110-137.*
Ray et al. (2003) Canc. Res., vol. 64, 1323-1330.*
Baker et al. (2008) Nat. Cell. Biol., vol. 10(7), 825-836, including Supplementary Information.*
Pajvani et al. (2005) Nat. Med., vol. 11(7), 797-803.*
Wang et al. (2001) J. Biol. Chem., vol. 276, 48655-48661.*
Baker et al. (2011) Nature, vol. 479, 232-237.*
Declaration by Remi-Martin Laberge under 37 CFR 1.132 filed in copending related U.S. Appl. No. 15/067,543 dated May 1, 2017.*
Abate-Daga, et al. Oncolytic adenoviruses armed with thymidine kinase can be traced by PET imaging and show potent antitumoural effects by ganciclovir dosing. PLoS One. 2011;6(10):e26142. doi: 10.1371/journal.pone.0026142. Epub Oct. 18, 2011.

(Continued)

*Primary Examiner* — Anne Marie S Wehbe
(74) *Attorney, Agent, or Firm* — Michael Schiff; Wilson Sonsini Goodrich & Rosati

(57) ABSTRACT

This invention provides a transgenic mouse with a $p16^{INK4a}$ promoter sequence that controls expression of a protein such that it is expressed preferentially in senescent cells. The protein either directly induces apoptosis, or converts a prodrug to a cytotoxic compound. In addition, the mouse is injected with syngeneic tumor cells, or has second transgene that causes tumors to form. Removing senescent cells from the mouse may result in the formation of fewer tumors.

12 Claims, 24 Drawing Sheets

(56) References Cited

U.S. PATENT DOCUMENTS

| | | |
|---|---|---|
| 2005/0019865 A1 | 1/2005 | Kihm et al. |
| 2005/0181076 A1 | 8/2005 | Ziegler |
| 2007/0099186 A1 | 5/2007 | D'Adda Di Fagagna et al. |
| 2008/0108062 A1 | 5/2008 | Sharpless et al. |
| 2008/0216180 A1 | 9/2008 | Abate-Shen et al. |
| 2008/0221132 A1 | 9/2008 | Cai et al. |
| 2008/0234362 A1 | 9/2008 | Chandler |
| 2009/0019554 A1 | 1/2009 | Selkirk et al. |
| 2009/0022465 A1 | 1/2009 | Chen et al. |
| 2009/0193533 A1 | 7/2009 | Edge et al. |
| 2009/0281129 A1 | 11/2009 | Chang et al. |
| 2010/0016218 A1 | 1/2010 | Lichter et al. |
| 2010/0125064 A1 | 5/2010 | Boettcher et al. |
| 2010/0190807 A1 | 7/2010 | Porter et al. |
| 2010/0260733 A1 | 10/2010 | Qi |
| 2010/0292200 A1 | 11/2010 | Kile et al. |
| 2010/0310504 A1 | 12/2010 | Lowe et al. |
| 2011/0023137 A1 | 1/2011 | Chu et al. |
| 2011/0189142 A1 | 8/2011 | May et al. |
| 2011/0212909 A1 | 9/2011 | Wen et al. |
| 2012/0108590 A1 | 5/2012 | Birtalan et al. |
| 2012/0156134 A1 | 6/2012 | Squires |
| 2012/0183534 A1 | 7/2012 | Gruber |
| 2013/0096121 A1 | 4/2013 | Wang et al. |
| 2013/0267534 A1 | 10/2013 | Bruncko et al. |
| 2013/0287763 A1 | 10/2013 | Sathyanarayanan et al. |
| 2013/0288980 A1 | 10/2013 | De Keizer et al. |
| 2013/0302283 A1 | 11/2013 | Kihm |
| 2014/0017341 A1 | 1/2014 | Gourlaouen |
| 2014/0073640 A1 | 3/2014 | Judd et al. |
| 2014/0189897 A1 | 7/2014 | Kirkland et al. |
| 2014/0275082 A1 | 9/2014 | Tao et al. |
| 2014/0329854 A1 | 11/2014 | Larsen et al. |
| 2014/0378683 A1 | 12/2014 | Porter et al. |
| 2015/0044184 A1 | 2/2015 | Chen et al. |
| 2015/0056195 A1 | 2/2015 | Bertolotto-Ballotti |
| 2015/0064137 A1 | 3/2015 | Lichtsteiner et al. |
| 2015/0072950 A1 | 3/2015 | Sauve et al. |
| 2015/0072972 A1 | 3/2015 | Mevellec et al. |
| 2015/0140036 A1 | 5/2015 | Mannick et al. |
| 2015/0151001 A1 | 6/2015 | Squires |
| 2015/0210717 A1 | 7/2015 | Günes et al. |
| 2015/0296755 A1 | 10/2015 | Kirkland et al. |
| 2017/0027139 A1 | 2/2017 | Van Deursen et al. |

FOREIGN PATENT DOCUMENTS

| | | |
|---|---|---|
| WO | WO-2008113131 A1 | 9/2008 |
| WO | WO-2009039553 A1 | 4/2009 |
| WO | WO-2009085216 A2 | 7/2009 |
| WO | WO-2009105234 A2 | 8/2009 |
| WO | WO-2009105533 A2 | 8/2009 |
| WO | WO-2010000491 A1 | 1/2010 |
| WO | WO-2010134790 A2 | 11/2010 |
| WO | WO-2010148447 A1 | 12/2010 |
| WO | WO-2011068561 A1 | 6/2011 |
| WO | WO-2011150016 A1 | 12/2011 |
| WO | WO-2012177927 A1 | 12/2012 |
| WO | WO-2013152038 A1 | 10/2013 |
| WO | WO-2013170174 A1 | 11/2013 |
| WO | WO-2014041125 A1 | 3/2014 |
| WO | WO-2014089124 A1 | 6/2014 |
| WO | WO-2014160661 A2 | 10/2014 |
| WO | WO-2014174511 A1 | 10/2014 |
| WO | WO-2014186878 A1 | 11/2014 |
| WO | WO-2015044649 A1 | 4/2015 |
| WO | WO-2015051766 A1 | 4/2015 |
| WO | WO-2015066442 A1 | 5/2015 |
| WO | WO-2015070280 A1 | 5/2015 |
| WO | WO-2015073644 A1 | 5/2015 |

OTHER PUBLICATIONS

Adams. Healing and hurting: molecular mechanisms, functions, and pathologies of cellular senescence. Mol Cell. Oct. 9, 2009;36(1):2-14. doi: 10.1016/j.molcel.2009.09.021.

Agarwalla, et al. Oncolytic herpes simplex virus engineering and preparation. Methods Mol Biol. 2012;797:1-19. doi: 10.1007/978-1-61779-340-0_1.

Baker, et al. BubR1 Insufficiency Causes Early Onset of Aging-Associated Phenotypes and Infertility in Mice. Genetics, vol. 36, No. 7, Jul. 2004, pp. 744-749.

Baker et al. Clearance of p16Ink4a-positive senescent cells delays ageing-associated disorders. Nature 479(7372):232-236 (2011).

Baker, et al. Clearance of p1ek4a-positive senescent cells delays ageing-associated disorders. Nature, Nov. 10, 2011, 479:232-237.

Baker, et al. Opposing roles for p16Ink4a and p19Arf in senescence and ageing caused by BubR1 insufficiency. Nat Cell Biol. Jul. 2008;10(7):825-36. doi: 10.1038/ncb1744. Epub May 30, 2008.

Baker, et al. Opposing roles for pl6Ink4a and pl9Arf in senescence and ageing caused by BubR1 insufficiency. Nat. Cell Biol., 2008, 10:825-836.

Bennett, et al. SP600125, An Anthrapyrazolone Inhibitor of Jun N-Terminal Kinase. PNAS, vol. 98, No. 24, 20, 2001, pp. 13681-13686.

Campisi, et al. Cellular senescence: a link between cancer and age-related degenerative disease? Semin Cancer Biol. Dec. 2011;21(6):354-9. doi: 10.1016/j.semcancer.2011.09.001. Epub Sep. 10, 2011.

Campisi, et al. Cellular senescence: when bad things happen to good cells. Nature Reviews Molecular Cell Biology 8:729-740, 2007.

Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.

Campisi, J. Senescent cells, tumor suppression, and organismal aging: good citizens, bad neighbors. Cell. Feb. 25, 2005;120(4):513-22.

Chang, et al. Effects of p21 Wafl/Cipl/Sdilon cellular gene expression: Implications for carcinogenesis, senescence, and age-related diseases. PNAS 97(8):4291-4296, 2000.

Chistiakov. How to fight with senescent cells? Geriatr Gerontol Int. Apr. 2011;11(2):233-5. doi: 10.1111/j.1447-0594.2010.00654.x.

Chung, et al. Molecular inflammation: underpinnings of aging and age-related diseases. Ageing Res Rev. Jan. 2009;8(1):18-30. doi: 10.1016/j.arr.2008.07.002. Epub Jul. 18, 2008.

Cibelli, et al. Cloned transgenic calves produced from nonquiescent fetal fibroblasts. Science, 1998, 280:1256-1258.

Co-pending U.S. Appl. No. 13/975,179, filed Aug. 23, 2013.

Co-pending U.S. Appl. No. 13/975,217, filed Aug. 23, 2013.

Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.

Davalos, et al. p53-dependent release of Alarmin HMGB1 is a central mediator of senescent phenotypes. J Cell Biol. May 13, 2013;201(4):613-29. doi: 10.1083/jcb.201206006. Epub May 6, 2013.

Davalos, et al. Senescent cells as a source of inflammatory factors for tumor progression. Cancer Metastasis Rev. Jun. 2010;29(2):273-83. doi: 10.1007/s10555-010-9220-9.

Deursen. Clearance of senescent cells and adult aging phenotypes. Pitts. Jun. 2014. 15 pages.

Deursen, et al. Senescent cells have some nerve! Mayo Clinic. NCI. Mar. 2015. Rochester, MN. 15 pages.

Deursen, et al. Senescent cells shorten health and life span. Mayo Clinic. Berlin. Feb. 2015. 30 pages.

Deursen, et al. Senescent in aging and age-related disease: from mechanism to therapy. Mayo Clinic. ICSA Conference. Jul. 2015. Santiago de Compostela. 40 pages.

Deursen. Senescent Cells as Drivers of Cancer & Aging. Mayo Clinic. NYU Dec. 2014. 55 pages.

Deursen. The role of p16+ (senescent) cells in aging. Erice. Jun. 2015. 17 pages.

Deursen. Understanding Senescence and Chromosomal Instability in Cancer and Aging. Mayo Clinic. Ohio State. Jan. 2015. 49 pages.

(56) References Cited

OTHER PUBLICATIONS

Dieffenbach, et al. PCR Primer: A Laboratory Manual, ed. Cold Spring Harbor Laboratory Press, 1995.
Dimri, et al. A biomarker that identifies senescent human cells in culture and in aging skin in vivo. Proc Natl Acad Sci U S A. Sep. 26, 1995;92(20):9363-7.
Drabek, et al. The expression of bacterial nitroreductase in transgenic mice results in specific cell killing by the prodrug CB1954. Gene Therapy, Feb. 1997, 4(2):93-100.
Efeyan, et al. Induction of p53-dependent senescence by the MDM2 antagonist nutlin-3a in mouse cells of fibroblast origin. Cancer Res. Aug. 1, 2007;67(15):7350-7.
Freund, et al. Inflammatory networks during cellular senescence: causes and consequences. Trends Mol Med. May 2010;16(5):238-46. doi: 10.1016/j.molmed.2010.03.003. Epub May 3, 2010.
Freund, et al. Lamin B1 loss is a senescence-associated biomarker. Mol Biol Cell. Jun. 2012;23(11):2066-75. doi: 10.1091/mbc.E11-10-0884. Epub Apr. 11, 2012.
Gan, et al. PPARy accelerates cellular senescence by inducing p16INK4' expression in human diploid fibroblasts. J. Cell Sci., 2008, 121:2235-2245.
Guatelli, et al. Isothermal, in vitro amplification of nucleic acids by a multienzyme reaction modeled after retroviral replication. Proc. Natl. Acad. Sci. USA, Mar. 1990, 87:1874-1878.
Handschin, et al. Skeletal muscle fiber-type switching, exercise intolerance, and myopathy in PGC-1alpha muscle-specific knockout animals. J Biol Chem. Oct. 12, 2007;282(41):30014-21. Epub Aug. 16, 2007.
Hartman, et al. Mutant mice with small amounts of BubR1 display accelerated age-related gliosis. Neurobiol. Aging, 2007, 28:921-927.
International search report and written opinion dated Apr. 22, 2014 for International PCT Patent Application No. PCT/US2013/072938.
International search report and written opinion dated Apr. 30, 2013 for PCT/US2012/069601.
International search report and written opinion dated May 6, 2015 for PCT/US2015/013376.
International search report and written opinion dated Jun. 29, 2015 for PCT/US2015/013387.
International search report and written opinion dated Aug. 13, 2013 for PCT/US2013/035023.
International Search Report and Written Opinion in International Application No. PCT/US2012/043613, dated Nov. 29, 2012, 9 pages.
International Search Report and Written Opinion received for PCT Patent Application No. PCT/US2013/035020, dated Jul. 22, 2013, 11 pages.
Johnson, et al. Somatic activation of the K-ras oncogene causes early onset lung cancer in mice. Nature. Apr. 26, 2001;410(6832):1111-6.
Kaina, B. DNA damage-triggered apoptosis: critical role of DNA repair, double-strand breaks, cell proliferation and signaling. Biochem Pharmacol. Oct. 15, 2003;66(8):1547-54.
Kim, et al. SP600125, an inhibitor of Jnk pathway, reduces viability of relatively resistant cancer cells to doxorubicin. Biochem Biophys Res Commun. Sep. 25, 2009;387(3):450-5. doi: 10.1016/j.bbrc.2009.07.036. Epub Jul. 14, 2009.
Kirkland, et al. Effects of fat depot site on differentiation-dependent gene expression in rat preadipocytes. Int. J. Obes. Relat. Metab. Disord., 1996, 20(Suppl 3):5102-107.
Krishnamurthy et al. Ink4a/Arf expression is a biomarker of aging. J Clin Invest 114:1299-1307 (2004).
Krtolica, et al. Senescent fibroblasts promote epithelial cell growth and tumorigenesis: a link between cancer and aging. Proc Natl Acad Sci U S A. Oct. 9, 2001;98(21):12072-7. Epub Oct. 2, 2001.
Kuilman, et al. The essence of senescence. Genes Develop., 2010, 24:2463-2479.
Laberge, et al. Glucocorticoids suppress selected components of the senescence-associated secretory phenotype. Aging Cell 11(4):569-578, 2012.
Laberge, et al. Mitochondrial DNA damage induces apoptosis in senescent cells. Cell Death Dis. Jul. 18, 2013;4:e727. doi: 10.1038/cddis.2013.199.
Le, et al. Ionizing radiation-induced long-term expression of senescence markers in mice is independent of p53 and immune status. Aging Cell. Jun. 2010;9(3):398-409. doi: 10.1111/j.1474-9726.2010.00567.x. Epub Mar. 13, 2010.
LeBrasseur, et al. Myostatin inhibition enhances the effects of exercise on performance and metabolic outcomes in aged mice. J. Gerontol. A. Biol. Sci. Med. Sci., 2009, 64:940-948.
Lessene; et al. Structure-guided design of a selective BCL-X(L) inhibitor. Jun. 2013, 9(6), 390-7.
Lewis. PCR's Competitors are alive and well and moving rapidly towards commercialization. Genetic Engineering News, 1992, 12:1, 2 pages.
Lo. Transformation by iontophoretic microinjection of DNA: multiple integrations without tandem insertions. Mol. Cell. Biol., 1983, 3:1803-1814.
Mallet, et al. Conditional cell ablation by tight control of caspase-3 dimerization in transgenic mice. Nat Biotechnol. Dec. 2002;20(12):1234-9. Epub Nov. 18, 2002.
Matsumoto, et al. Aging-associated vascular phenotype in mutant mice with low levels of BubR1. Stroke, 2007, 38:1050-1056.
Moody, et al. Conditional activation of Neu in the mammary epithelium of transgenic mice results in reversible pulmonary metastasis. Cancer Cell. Dec. 2002;2(6):451-61.
Nasu, et al. Suicide gene therapy for urogenital cancer: current outcome and prospects. Mol Urol. 2000 Summer;4(2):67-71.
Office Action dated Jan. 3, 2017 for U.S. Appl. No. 14/792,208.
Office action dated Jan. 9, 2015 for U.S. Appl. No. 12/809,952.
Office action dated Apr. 7, 2015 for U.S. Appl. No. 14/125,841.
Office action dated May 30, 2014 for U.S. Appl. No. 12/809,952.
Office action dated Aug. 13, 2015 for U.S. Appl. No. 14/792,208.
Office action dated Sep. 11, 2015 for U.S. Appl. No. 13/975,179.
Office action dated Sep. 25, 2015 for U.S. Appl. No. 13/975,217.
Office Action dated Nov. 3, 2016 for U.S. Appl. No. 15/067,543.
Office action dated Nov. 25, 2014 for U.S. Appl. No. 13/830,790.
Pajvani, et al. Fat apoptosis through targeted activation of caspase 8: a new mouse model of inducible and reversible lipoatrophy. Nat Med. Jul. 2005; 11(7):797-803. Epub Jun. 19, 2005.
Prieur, et al. Cellular senescence in vivo: a barrier to tumorigenesis. Curr Opin Cell Biol. Apr. 2008;20(2):150-5. doi: 10.1016/j.ceb.2008.01.007. Epub Mar. 18, 2008.
Ray, et al. Imaging tri-fusion multimodality reporter gene expression in living subjects. Cancer Res. Feb. 15, 2004;64(4):1323-30.
Rodier, et al. Persistent DNA damage signalling triggers senescence-associated inflammatory cytokine secretion. Nat Cell Biol. Aug. 2009;11(8):973-9. doi: 10.1038/ncb1909. Epub Jul. 13, 2009.
Roninson. Tumor Cell Senescence in Cancer Treatment. Cancer Research 63(11):2705-2715, 2003.
Sambrook, et al. Molecular Cloning, A Laboratory Manual, second edition, Cold Spring Harbor Press, Plainview; NY. 1989.
Schmitt, et al. A senescence program controlled by p53 and p16INK4a contributes to the outcome of cancer therapy. Cell. May 3, 2002;109(3):335-46.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Sharpless, et al. Telomeres, stem cells, senescence, and cancer. Journal of Clinical Investigation 113(2):160-168, 2004.
Sis, et al. Accelerated expression of senescence associated cell cycle inhibitor p16INK4A in kidneys with glomerular disease. Kidney Int. Feb. 2007;71(3):218-26. Epub Dec. 20, 2006.
Soleimani, et al. A protocol for isolation and culture of mesenchymal stem cells from mouse bone marrow. Nat. Protoc., 2009, 4:102-106.
Stanley et al. Senescence and the Healing Rates of Venous Ulcers. J Vasc Surg. Jun. 2001;33(6):1206-11.
Tchkonia, et al. Fat tissue, aging, and cellular senescence. Aging Cell. Oct. 2010;9(5):667-84.

(56) References Cited

OTHER PUBLICATIONS

Te Poele, et al. DNA damage is able to induce senescence in tumor cells in vitro and in vivo. Cancer Res. Mar. 15, 2002;62(6):1876-83.
Thompson, et al. Germ line transmission and expression of a corrected HPRT gene produced by gene targeting in embryonic stem cells. Cell, 1989, 56:313-321.
Tsuji, et al. Alveolar cell senescence exacerbates pulmonary inflammation in patients with chronic obstructive pulmonary disease. Respiration. 2010;80(1):59-70. doi: 10.1159/000268287. Epub Dec. 17, 2009.
Van Der Putten, et al. Efficient insertion of genes into the mouse germ line via retroviral vectors. Proc. Natl. Acad. Sci. USA, 1985, 82:6148-1652.
Wakayama, et al. Full-term development of mice from enucleated oocytes injected with cumulus cell nuclei. Nature, 1988, 394:369-374.
Wang, et al. Characterization of regulatory elements on the promoter region of p16(INK4a) that contribute to overexpression of p16 in senescent fibroblasts. J Biol Chem. Dec. 28, 2001;276(52):48655-61. Epub Oct. 11, 2001.
Wang, et al. PANIC-ATTAC: a mouse model for inducible and reversible beta-cell ablation. Diabetes, Aug. 2008, 57(8):2137-48.
Weiss. Hot prospect for new gene amplifier. Science, 1991, 254:1292-1293.
Wilmut, et al. Viable offspring derived from fetal and adult mammalian cells. Nature, 1997, 385:810-813.
Zhao; et al. Small molecule inhibitors of MDM2-p53 and MDMX-p53 interactions as new cancer therapeutics. BioDiscovery, Aug. 2013, 8(4), 15 pages.
Baker, et al. Naturally occurring p16(Ink4a)-positive cells shorten healthy lifespan. Nature. Feb. 11, 2016;530(7589):184-9. doi: 10.1038/nature16932.
Braun, et al. Cellular senescence limits regenerative capacity and allograft survival.J Am Soc Nephrol. Sep. 2012;23(9):1467-73. doi: 10.1681/ASN.2011100967. Epub Jul. 12, 2012.
Gorenne, et al. Vascular smooth muscle cell senescence in atherosclerosis. Cardiovasc Res. Oct. 1, 2006;72(1):9-17. Epub Jun. 6, 2006.
International Search Report and Written Opinion dated Jul. 11, 2013 for International PCT Patent Application No. PCT/US2013/036811.
Jia, et al. Cancer gene therapy targeting cellular apoptosis machinery. Cancer Treat Rev. Nov. 2012;38(7):868-76. doi: 10.1016/j.ctrv.2012.06.008. Epub Jul. 15, 2012.
Kassem, et al. Senescence-associated intrinsic mechanisms of osteoblast dysfunctions. Aging Cell. Apr. 2011;10(2):191-7. doi: 10.1111/1474-9726.2011.00669.x. Epub Feb. 18, 2011.
Martin, et al. Aging, articular cartilage chondrocyte senescence and osteoarthritis. Biogerontology. 2002;3(5):257-64.
Martin, et al. The Role of Chondrocyte Senescence in the Pathogenesis of Osteoarthritis and in Limiting Cartilage Repair. J Bone Joint Surg Am, vol. 85, Suppl 2, Apr. 2003, pp. 106-110.
Minamino et al., Vascular Cell Senescence: Contribution to Atherosclerosis. Journal of the American Heart Association, Circ Res. Jan. 5, 2007;100(1):15-26.
Myohanen, et al. Sequence-specific DNA binding activity of RNA helicase A to the p16INK4a promoter. Jan. 12, 2001, 276(2), 1634-42.
Naylor, et al. Senescent cells: a novel therapeutic target for aging and age-related diseases. Jan. 2013, 93(1), 105-16.
Office Action dated Jun. 6, 2016 for U.S. Appl. No. 14/792,208.
Office Action dated Aug. 9, 2017 for U.S. Appl. No. 14/792,208.
Office Action dated Aug. 9, 2017 for U.S. Appl. No. 15/067,543.
Office Communication dated Jul. 31, 2017 for U.S. Appl. No. 14/394,854.
Roberts, et al. Senescence in human intervertebral discs. Eur Spine J. Aug. 2006;15 Suppl 3:S312-6. Epub Jun. 14, 2006.
Robl, et al. Transgenic animal production and animal biotechnology. Theriogenology. Jan. 1, 2007;67(1):127-33.
Strasser, et al. Apoptosis signaling. Annu Rev Biochem. 2000;69:217-45.

\* cited by examiner

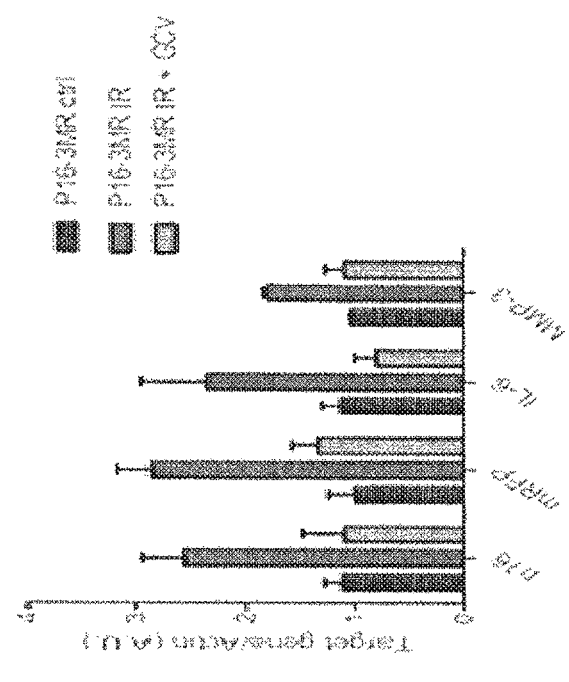
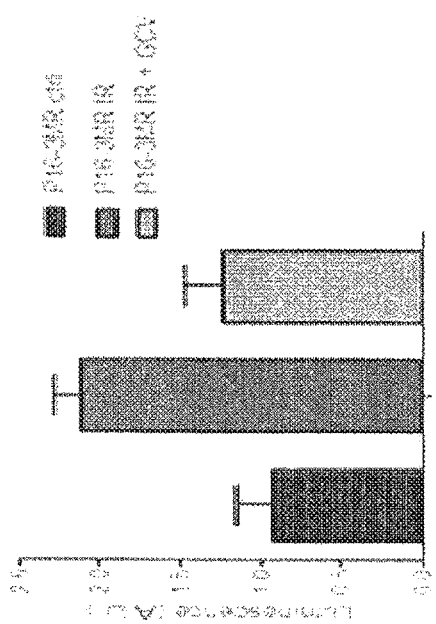
Fig. 1

Entire 9267 nt sequence, uninterrupted
ctacattgtaagcgttaatatttgttaaaaatcgcgttaaatttgttaaatcagctcattt
tttaaccattaggcgaaatcggcaaaatccttataaatcaaaagaatagaccgagatggggt
tgagtgttgtccagttggaacangagtccactattaangaacgtggactccaacgtcaaagg
gcgaaaaaccgtctatcaggcgatggccactacgtgaaccatcaccctaatcaagttttg
gggtcgaggtgccgtaaagcactaaattcggaacoctaaaggagccaccgatttagagcttgac
gggaaaagccggcgaacgtggcgagaaaggaaggggagaaagcgaaaggagcgagcgctagggc
gctggcaatgtgtagcggtcacgctgcgcgtaaccaccacaccegccgcgctaatgcgccgcta
caggcgcgtccattcgccatcaggctgcgcaactgttggaaggcgatcggtgcgggcct
ctgctattacgcagctgcgataaggggatgtgctgcaaggcgatttaagtgggaaagcc
agggttttcccagtcacgacgttgtaaaacgacggccagtgagcgcgctaatacgactcacta
taggcgaattggagctccacgcgcgtggtggccgctctagaactagtgGATCCGTGTAAAGTC
ACTGCTTTATAGCTACATCTGCATAGATCCCCTGTATGAAAGCATGTACTACCTGGATAATAA
TATCTGTATTTTTCTGTAGTAGGAAATCAGTGTAGTTTTTAAAACCAAAAAGTATTGTTATTAA
TCTATCTTTGATCTCAAACAATTTCAATGACCTAGTATAGTGATTTCTACGGAAAGCCCTGCAA
TTTACTCAAAGCAGTTTTTAAATATTGTTTTAAAAGTGTGTGTGTGTGTGTGTGTGTGTGTG
TGTGTGTGTGGTGTTAAAGTCATTTTCAAACCCCTCACAATGTCTTGAATGTGACATTTGAGTC
ATTTATGGTAACTTATAACTCCTTTGAAGAAGTTATTCAGAATGAGGTTCCAGACACACAAAT
GCACAATACACCATTTTTCCTTCCAGTTAACAATCAGAGGGCAACACTTATTTTAAAGGAAAA
TCGACTCCATAAGCGACTTTATAAAGGGGTAGACATAAACCAGTATCAGGGATAAACTCTCCGT
TCCCCTGTTTAACCTAATTTTCCCAGGGCCATCCTGAATACGAATTTTCTCTTGAAATACAGT
CAAAGAAAAAGTGGTAGGCTACAGAGCAGGAGGAAACACTGGACACAGCGCACCCACCCCAGAGT
CACTTCCCTTAATCTAATGACTAGGTTTTTCTGAAAGTTATTTTGTTAGAACACAGGAACTTTT
GCGACCACAGTGATGCTTTTAGAGGGTTGAATCCTCAAAAAGAAAATTAATCGCAACTAGTAGA
AGGGAGATTACTTATTGATTCTTATAACTTCTGCAGGAATACACAGTTATGAGTTAGGGCAAAG
AGAAAATTGACTTTTAATATTCTCTATCACTAACATGAGAGAACATGTATGTGTTCCAAAATAA
TTTTATTTATTGAAAACCCGCTATATACCTGGATTTTCACAGAATATTCATTACTCTCCAAAA
TGGCCTTTTCTAGGTGAATTTTATTTTCCTTACAGACCCTCAAGAAGTTTACATAATTTACTTAA
ACCTGAGGAGAGAGAACAAAGCCTCAGAAAATTTACATAGTTTATTTAAACTAAACTCAGCTTG
CTTGGTAGCAGCTTCTAATCCCAGCAGTTAAAGAGACAGAAGCAGGGCCAACCTGGGTATAAT
ATAAGGTGAGACTCTCCTTTCTTTCTCTCTGTCTCTGTCTGTCTCTGTCTCTGTGTGTGTGT
GTGTGTGTGTGTGTGTGTGTGTCTCCCTCTCTCTCTCTCTCTCTCTCTCTCTCTCTCTCTCTG
TCTCTCTCTCCCTCCCCCTCCCTCCCTCTCCCCCTCCTCTCTCCCTCCCTCTCCCTCCCCCCC
CCCACACATTTGAATTCGTGGAGTTGGTAAATGAGGGGTCAGTTCTCTGTCTGTCTGTAGTTTT
GTGTCCACAGGATATGACTGACATTCTCACCACACACATACAAAGTCAAAAATAGCTGTGGCCA
TATAAAGAATATGGGAGAGAAAATTATTCAAAATCTGCAGAAAATAATGCCAGGCCTTTAATC
CTGGCACCCAGGAGGCAGAAGGGAGACAGAGTTCTGAGTTTATGCTGAGTTCCAGGAGTGGAAG
AAAGCGGCCATTGCCTTTCTGGTGAGGACTGTCTTTTTAAATCCTCCCTTCTGTCCAGTACTGT
AACTCTGCCCAAAGCGTGTTCTTCTTCCTGCCTCACAAGATTGCAAAGACGTTTTTAACGAACA
ATTTAAACCGGTGCAACGTTTATGCGCAGCACACCAACTCATTTAAACAAACAACAGCCCCATA
AAATAGAAATACTTTATAAGCAGATTGCCCTCCGATGACTTCACCCCGTCACTTTTTTATAGTT
GTGTACAGAATCCTAGCACTGATACAGCAACATCAGAAATGTTTCTGCAAATCCTTCGCAAAGA
TTCGGATTTCATACTGGCGTGGTACCCTCCAAAATGAGTTGTTTGAGCTAGGGTTGTTGGGAT
CTCAGCTTGGCGAAGTTGTAGCTCTTTCTTCTGAATAAAAGATGACACAATTTTCTGCTAAGAT

*Fig. 5A*

GTTAAATACCTTAAGTTTCAGTGTAGTGATGAAAATTACCCTCCTTCGTTTTTCTAATACCTGG
GTGTTGCACTGGGGAGGAAGGAGAGATTTCGAGAAGGACTAGTTCACTTTCTCAGAAGACACGT
GTGCACTTCTTTGCTGTGCGGGTCCAGAAGGAGCCCAGCGTGTCAAAGGGTGACCAGCCATGGG
GGAGGGGTGTTAGCGTGGGTAGCAGGCGGGGCTGTCCGATCCTTTAGCGGCTGTTTCAACGCCC
AGCTCTCCTCCTGAACCCTGCATCTCTTCTGTAGTCCGGGCTCCATCCCTTTCCCCTCCCCCAT
CCGGAGGTGGGCGGAACAGCAGTGTTTTCAGGGGTGTTCAATTCATGCTATATTCAGGGCAAAT
AGCGCCACCTATGGCGGGCTGTGGAGCCAGGTCAGGAGCAGAGTGTGGCTCCCCCCTCCCCCCA
CACCATCCTCAGAGGAAGGAAGGAGGGACCCACTGGTCACACGACTGCGCGATTGGGCGGGCAC
TGAATCTCCCGCGAGGAAAGCGAACTCGAGGAGAGCCATCACGCGTAGCatggggagtagcatga
gcaagcctaaggacccagccagtgctctagaggcgtccaagtcgaaccattagtccggcga
tggcaggaacattcctaaaggggacaacatgtgtcgtccattataactggcatgttggaggac
ggcaaaaggtggacagtagtagagatcgcaataaacctttcaaattcatgttggggaaacaag
aagtcattaggggatggaggaggcgtggctcaaatgccgtcggccaaccgctaagctcac
catcagccccgactacgcatacgccgtaccggacatcccggaattaticcccctcacgctacc
ttggtgttgacgtcgaactgttgaagctcgagactagaggagtgcaggtggtgactatctccc
caggagacggcgcacctcccaagcgcggccagactgcgtggtgcactacaccgggatgct
tgatgatggaaagaaagtgattcctcccggacagaaacatgccctttagttatgctaggc
aagctaggagggtgatccgaggctggaaagatggggttgcccagatgatgtgtgggtcagagagcca
acctgactatatctccagatgatctatggtgccactggcacccaggcatcatcccatcccaca
tgccactctcgtcttgatgtggagctctaaactggaaactagtagtgatcacagacttg
gacaaagtttaccaaatgaaaagcaaacctcggggatactgtctgatcatcaacaatcacaatt
ttgcaaatgcacgggagtaagtgcccaactcacatgcattagggacaggaatggaatacactt
gaatgcaggggctttgaccacgaccttgaagagctcattttgagatcaagccccacgatgac
tgcacagtagagctaatctatgagatttgaaaatctaccaactcatggaccacagtaacatgg
actgcttcatctgctgatcctctcccatggagacaagggcatcatctatggaactgatggaca
ggaggcccccatctatgagctgacatctcagttcctggttgaagtgccttccctgctgga
aaacccaaagtgtttttattcaggcctgtcgggggatactaccgaaaggtataacctgttg
agactgatcagaggagcaacccatttagaaatggattataatcacactcaaacgagatatat
cccggatgaggctgacttctgtgtggggatggtcactgtgaatactgtgttcctaccgaaac
cctgcagaggggacctggtacatccagtcactttgccagtgcctgagagagagcgatgtcctcgag
gcgatgatattcactcatcctgactgaagtgaactatgaagtaagcaacaggatgacaagaa
aaacatggggaaacagatgcctcagcctactttcactactagaaaaaacctgtcttcccttct
gatgatacaaggagtgacgacgataagtgaggatcaacctcgaggaatcACGCGTTTAATTAA
CTCGAGGTTTCGAGGTCGACGGTATCGATAAGCTTGATATCGAATTCCGCCCCTCTCCCTCCC
CCCCCCCTAACGTTACTGGCCGAAGCCGCTTGGAATAAGGCCGGTGTGCGTTTGTCTATATGTT
ATTTTCCACCATATTGCCGTCTTTTGGCAATGTGAGGGCCCGGAAACCTGGCCCTGTCTTCTTG
ACGAGCATTCCTAGGGGTCTTTCCCCTCTCGCCAAAGGAATGCAAGGTCTGTTGAATGTCGTGA
AGGAAGCAGTTCCTCTGGAAGCTTCTTGAAGACAAACAACGTCTGTAGCGACCCTTTGCAGGCA
GCGGAACCCCCCACCTGGCGACAGGTGCCTCTGCGGCCAAAAGCCACGTGTATAAGATACACCT
GCAAAGGCGGCACAACCCCAGTCCCACGTTGTGAGTTGGATAGTTGTGGAAAGAGTCAAATGGC
TCTCCTCAAGCGTATTCAACAAGGGGCTGAAGGATGCCCAGAAGGTACCCCATTGTATGGGATC
TGATCTGGGGCCTCGGTGCACATGCTTTACATGTGTTTAGTCGAGGTTAAAAAAACGTCTAGGC

*Fig. 5B*

```
CCCCCGAACCACGGGGACGTGGTTTTCCTTTGAAAAACACGATGATAATATGGCCACAACCATG
GTGAGCAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAACAT
CGAGGACGGCAGCGTGCAGCTCGCCGACCACTACCAGCAGAACACCCCCATCGGCGACGGCCCC
GTGCTGCTGCCCGACAACCACTACCTGAGCACCCAGTCCGCCCTGAGCAAAGACCCCAACGAGA
AGCGCGATCACATGGTCCTGCTGGAGTTCGTGACCGCCGCCGGGATCACTCTCGGCATGGACGA
GCTGTACAAGTAAAGCGGCCGCGATCTTTTTCCCTCTGCCAAAAATTATGGGGACATCATGAAG
CCCCTTGAGCATCTGACTTCTGGCTAATAAAGGAAATTTATTTTCATTGCAATAGTGTGTTGGA
ATTTTTTGTGTCTCTCACTCGGAAGGACATATGGGAGGGCAAATCATTTAAAACATCAGAATGA
GTATTTGGTTTAGAGTTTGGCAACATATGCCATATGCTGGCTGCCATGAACAAAGGTGGCTATA
AAGAGGTCATCAGTATATGAAACAGCCCCCTGCTGTCCATTCCTTATTCCATAGAAAAGCCTTG
ACTTGAGGTTAGATTTTTTTATATTTTGTTTGTGTTATTTTTTCTTAACATCCCTAAAAT
TTTCCTTACATGTTTTACTAGCCAGATTTTTCCTCCTCTCCTGACTACTCCCAGTCATAGCTGT
CCCTCTTCTCTTATGAAGATCCCTCGACCTGCAGCCCAAGCTTGGCGTAATCATGGTCATAGCT
GTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCG
CTTTCCAGTCGGGAAACCTGTCGTGCCAGCGGATCCGCATCTCAATTAGTCAGCAACCATAGTC
CCGCCCCTAACTCCGCCCATCCCGCCCCTAACTCCGCCCAGTTCCGCCCATTCTCCGCCCCATG
GCTGACTAATTTTTTTTATTTATGCAGAGGCCGAGGCCGCCTAAACCGCCGGCCATcgatacgg
tcgacctcgagggggggcccggtaccagctttgttccctttagtgagggttaattgcgcgct
tggcgtaatcatggtcatagctgtttcctgtgtgaaattgttatccgctcacaattccacaca
catacgagccggaagcataaagtgtaaagcctggggtgcctaatgagtgagctaactcacatta
attgcgttgcgctcactgcccgctttccagtcgggaaacctgtcgtgccagctgcattaatgaa
tcggccaacgcgcggggagaggcggtttgcgtattgggcgctcttccgcttcctcgctcactga
ctcgctgcgctcggtcgttcggctgcggcgagcggtatcagctcactcaaaggcggtaatacgg
ttatccacagaatcaggggataacgcaggaaagaacatgtgagcaaaaggccagcaaaaggcca
ggaaccgtaaaaaggccgcgttgctggcgtttttccataggctccgcccccctgacgagcatca
caaaaatcgacgctcaagtcagaggtggcgaaacccgacaggactataaagataccaggcgttt
ccccctggaagctccctcgtgcgctctcctgttccgaccctgccgcttaccggatacctgtccg
cctttctcccttcgggaagcgtggcgctttctcatagctcacgctgtaggtatctcagttcggt
gtaggtcgttcgctccaagctgggctgtgtgcacgaaccccccgttcagcccgaccgctgcgcc
ttatccggtaactatcgtcttgagtccaacccggtaagacacgacttatcgccactggcagcag
ccactggtaacaggattagcagagcgaggtatgtaggcggtgctacagagttcttgaagtggtg
gcctaactacggctacactagaaggacagtatttggtatctgcgctctgctgaagccagttacc
ttcggaaaaagagttggtagctcttgatccggcaaacaaaccaccgctggtagcggtggttttt
ttgtttgcaagcagcagattacgcgcagaaaaaaaggatctcaagaagatcctttgatcttttc
```

*Fig. 5C* tacggggtctgacgctcagtggaacgaaaactcacgttaagggattggtcatgagattatca
aaaaggatcttcacctagatcctttaaattaaaaatgaagttttaaatcaatctaaagtatat
atgagtaaacttggtctgacagttaccaatgcttaatcagtgaggcacctatctcagcgatctg
tctatttcgttcatccatagttgcctgactccccgtcgtgtagataactacgatacgggaggg
ttaccatctggccccagtgctgcaatgataccgcgagacccacgctcaccggctccagatttat
cagcaataaaccagccagccggaagggccgagcgcagaagtggtcctgcaactttatccgcc
tccatccagtctattaattgttgccgggaagctagagtaagtagttcgccagttaatagtttgcgc
aacgttgttgccattgctacaggcatcgtggtgtcacgctcgtcgtttggtatggcttcattca
gctccggttcccaacgatcaaggcgagttacatgatcccccatgttgtgcaaaaaagcggttag
ctccttcggtcctccgatcgttgtcagaagtaagttggccgcagtgttatcactcatggttatg
gcagcactgcataattctcttactgtcatgccatccgtaagatgcttttctgtgactggtgagt
actcaaccaagtcattctgagaatagtgtatgcggcgaccgagttgctcttgcccggcgtcaat
acgggataataccgcgccacatagcagaactttaaaagtgctcatcattggaaaacgttcttcg
gggcgaaaactctcaggatcttaccgctgttgagatccagttcgatgtaacccactcgtgcac
ccaactgatcttcagcatcttttactttcaccagcgtttctgggtgagcaaaaacaggaaggca
aaatgccgcaaaaaagggaataagggcgacacggaaatgttgaatactcatactcttcctttt
caatattattgaagcatttatcagggttattgtctcatgagcggatacatatttgaatgtattt
agaaaaataaacaaataggggttccgcgcacatttccccgaaaagtgccac (SEQ ID
NO:1)

*Fig. 5D* ctaaatgtaagcgttaatatttgttaaaattcgcgttaaatttttgttaaatcagctcattt
tttaaccaataggccgaaatcggcaaaatcccttataaatcaaaagaatagaccgagatagggt
tgagtg (SEQ ID NO:2)

F1 ori:
ttgttccagtttggaacaagagtccactattaaagaacgtggactccaacgtcaaagggcgaaa
aaccgtctatcagggcgatggcccactacgtgaaccatcacccctaatcaagttttttggggtcg
aggtgccgtaaagcactaaatcggaaccctaaagggagcccccgatttagagcttgacggggaa
agccggcgaacgtggcgagaaaggaagggaagaaagcgaaaggagcgggcgctagggcgctggc
aagtgtagcggtcacgctgcgcgtaaccaccacacccgccgcgcttaatgcgccgctacagggc
gcgtc (SEQ ID NO:3)

LacZ alpha:
ccattcgccattcaggctgcgcaactgttgggaagggcgatcggtgcgggcctcttcgctatta
cgccagctggcgaaagggggatgtgctgcaaggcgattaagttgggtaacgccagggttttccc
agtcacgacgt (SEQ ID NO:4)

M13 fwd:
tgtaaaacgacggccagtgagcgcgc (SEQ ID NO:5)

T7:
gtaatacgactcactatagggcgaattggagctccaccgcggtggcggccgctctagaactagtg (SEQ ID NO:6)

BAMH1, p16 promoter:
GATCC (SEQ ID NO:7)

forprimer3, p16 promoter:
GTGTAAAGTCACT (SEQ ID NO:8)

*Fig. 6A* p16 promoter:
CTTTTATAGCTACATCTGCATAGATCCCCTGTATGAAAGCATGTACTACCTGGATAATAATATC
TGTATTTTTCTGTAGTAGGAAATCAGTGTAGTTTTTAAAACCAAAAAGTATTGTTATTAATCTA
TCTTTGATCTCAAACAATTTCAATGACCTAGTATAGTGATTCTACCGGAAAGCCCTGCAATTTA
CTCAAAGCAGTTTTTAAATATTGTTTTAAAAGTGTGTGTGTGTGTGTGTGTGTGTGTGTGTGTG
TGTGTGGTGTTAAAGTCATTTTCAAACCCCTCACAATGTCTTGAATGTGACATTTGAGTCATTT
ATGGTAACTTATAACTCCTTTGAAGAAGTTATTCAGAATTGAGGTTCCAGACACACAAATGCAC
AATACACCATTTTTCCTTCCAGTTAACAATCAGAGGGCAACACTTATTTTAAAGGAAAATCGA
CTCCATAAGGGACTTTATAAAGGGGTAGACATAAACCAGTATCAGGGATAAACTCTCCCTTCCC
CTGTTTAACCTAATTTTCCCAGGGCCATCCTGGAATACGAATTTTCTCTTGAAATACAGTCAAA
GAAAAAGTGGTAGGCTACAGAGCAGAGGAAACACTGGACACAGCGACCCACCCCAGAGTCACTT
CCCTTAATCTAATGACTAGGTTTTTTCTGAAAGTTATTTTGTTAGAACACAGGAACTTTTGCCGA
CCACAGTGATGCTTTTAGAGGGTTGAATCCTCAAAAAGAAAATTAATCGCAACTAGTAGAAGGG
AGATTACTTATTGATTCTTATAACTTCTGCAGGAATACACAGTTATGAGTTAGGGCAAAGAGAA
AATTGACTTTTAATATTCTCTATCACTAACATGAGAGAACATGTATGTGTTCCAAAATAATTTT
TATTTATTGAAAACCCGCTATATACCTGGATTTTCACAGAATATTCATTACTCTCCAAAATGGC
CTTTTCTAGGTGAATTTTATTTTCCTTACAGACCTCAAGAAGTTTACATAATTTACTTAAACCT
GAGGAGAGAGAACAAAGCCTCAGAAAATTTACATAGTTTATTTAAACTAAACTCAGCTTGCTTG
GTAGCAGCTTCTAATCCAGCAGTTAAAGAGACAGAAGCAGGGCCAACCTGGGGTATAATATAA
GGTGAGACTCTCCTTTCTTTCTCTCTGTCTCTGTCTGTCTCTGTCTCTGTGTGTGTGTGTGTGT
GTGTGTGTGTGTGTGTGTCTCCTCTCTCTCTCTCTCTCTCTCTCTCTCTCTCTCTCTCTCTGTCTC
TCTCTCCCTCCCCCTCCCTCCCTCTCCCCCTCCTCTCTCCCTCCCTCTCCCTCCCCCCCCCCA
CACATTTGAATTCGTGGAGTTGGTAAATGAGGGGTCAGTTCTCTGTCTGTCTGTAGTTTTGTGT
CCACAGGATATGACTGACATTCTCACCACACACATACAAAGTCAAAAATAGCTGTGGCCATATA
AAGAATATGGGGAGAGAAAATTATTCAAAATCTGCAGAAAATAATGCCAGGCCTTTAATCCTGG
CACCCAGGAGGCAGAAGGGAGACAGAGTTCTGAGTTTATGCTGAGTTCCAGGAGTGGAAGAAAG
GGCCATTGCCTTCTGGTGAGGACTGTCTTTTAAATCCTCCCTTCTGTCCAGTACTGGTAACT
CTGCCCAAAGCGTGTTCTTCTTCCTGCCTCACAAGATTGCAAAGACGTTTTAACGAACAATTT
AAACCCGTGCAACGTTTATGCGCAGCACCAACCAACTCATTTAAACAAACAACAGCCCCATAAAT
AGAAATACTTTATAAGCAGATTGCCCTCCGATGACTTCACCCCGTCACTTTTTATAGTTGTGT
ACAGAATCCTAGCACTGATACAGCAACATCAGAAATGTTTCTGCAAATCCTTCGCAAAGATTCG
GATTCATACTGGGCGTGGTACCCTCCAAAATGAGTTGTTTGAGCTAGGGTTGTTGGGATCTCA
GCTTGGCGAAGTTGTAGCTCTTTCTTCTGAATAAAAGATGACACAATTTTCTGCTAAGATGTTA
AATACCTTAAGTTTCACTGTAGTGATGAAAATTACCCTCCTTCGTTTTTCTAATACCTGGGTGT
TGCACTGGGGAGGAAGGAGAGATTCGAGAAGGACTAGTTCACTTTCTCAGAAGACACGTGTGC
ACTTCTTTGCTGTGCGGGTCCAGAAGGAGCCCAGCGTGCAAAGGGTGACCAGGCATGGGGAG
GGGTGTTAGCGTGGGTAGCAGGCGGGGCTGTCCGATCCTTTAGCGGCTGTTCAACGCCCAGCT
CTCCTCCTGAACCCTGCATCTCTTCTGTAGTCCGGGCTCCATCCCTTTCCCCTCCCCCATCCGG
AGGTGGGGGAACAGCAGTGTTTTCAGGGGTGTTCAATTCATGCTATATTCAGGGCAAATAGCG
CCACCTATGGCGGGCTGTGGAGCCAGGTCAGGAGCAGAGTGTGGCTCCCCCCCCCCCCCACACC
ATCCTCAGAGGAAGGAAGGAGGGACCCACTGGTCACACGACTGGGCGATTGGGCGGGCACTGAA
TCTCCGCGAGGAAAGCGAACTCGAGGAGAGCCATCACGCGTAGC (SEQ ID NO:9)

*Fig. 6B*

FKBP:
atggggagtagcaagagcaagcctaaggaccccagccagcgctctagaggcgtccaagtcgaaa
ccattagtcccggcgatggcagaacatttcctaaaaggggacaaacatgtgtcgtccattatac
aggcatgttgaggacggcaaaaaggtggacagtagtagagatcgcaataaaccttcaaatc
atgttgggaaaacaagaagtcattaggggatgggaggagggcgtggctcaaatgccgtcggcc
aacgcgctaagctcaccatcagccccgactacgcatacggcgctacggacatcccggaatat
tccccctcacgctaccttggtgtttgacgtcgaactgttgaagctcgagactagaggagtgcag
gtggagactatctccccaggagacgggcgcacttccccaagcgcggccagacctgctggtgc
actacaccgggatgcttgaagatggaaagaaagttgattcctcccgggacagaaacaagcctt
taagttatgctaggcaagcaggaggtgatccgaggctggaagaaggggttgcccagatgagt
gtgggtcagagagccaaactgactatatctccagattatgcctatggtgccactgggcacccag
gcatcatcccaccacatgccactctcgtcttcgatgtggagcttctaaaaactggaaactagt
(SEQ ID NO:10)

Casp8:
agtgaatcacagacttggacaaaagttaccaaatgaaaagcaaacctcggggatactgtctga
tcatcaacaatcacaatttgcataagcacgggagaaagtgcccaaacttcacagcattaggga
caggaaaggaacacacttggatgcaggggcttgaccacgaccttgaagagcttcatttgag
atcaagcccacgatgactgcacagtagagcaaatctatgagattttgaaaatctaccaactca
tggaccacagtaacatggactgcttcatctgctgtatcctctcccatggagacaagggcatcat
ctatggcactgatggacaggaggcccccatctatgagctgacatctcagttcactggttgaag
tgccctccttgctggaaaacccaaagtgttttttattcaggcttgtcaggggaataactacc
agaaaggtatacctgttgagactgattcagaggagcaaccctatttagaaatggattatcatc
accccaaacgagatatatcccggatgaggctgacttctgctggggatggccactgtgaataac
tgtgttcctaccgaaaccctgcagagggaactggtacatccagtcacttgcagagcctga
gagagcgatgtcctcgaggcgatgatattctcaccatcctgactgaagtgaactatgaagtaag
caacaaggatgacaagaataacatggggaaacagatgcctcagcctacttcacactaagaaaa
aaacttgtcttcccttctgat (SEQ ID NO:11)

Flag/Tag/Stop:
Gattacaaggatgacgacgataagtga (SEQ ID NO:12)

3'UTR:
ggatc (SEQ ID NO:13)

Multiple cloning site (MluI, PacI, XhoI, PmeI)
aacctgaggaattcACGCGTTTAATTAACTCGAGGTTT (SEQ ID NO:14)

*Fig. 6C*

IRES, GFP:
TCGAGGTCGACGGTATCGATAAGCTTGATATCGAATTCCGCCCCTCTCCCTCCCCCCCCCTAA
CGTTACTGGCCGAAGCCGGCTTGGAATAAGGCCGGTGTGCGTTTGTCTATATGTTATTTTCCACC
ATATTGCCGTCTTTTGGCAATGTGAGGGCCCGGAAACCTGGCCCTGTCTTCTTGACGAGCATTC
CTAGGGGTCTTTCCCCTCTCGCCAAAGGAATGCAAGGTCTGTTGAATGTCGTGAAGGAAGCAGT
TCCTCTGGAAGCTTCTTGAAGACAAACAACGTCTGTAGCGACCCTTTGCAGGCAGCGGAACCCC
CCACCTGGCGACAGGTGCCTCTGCGGCCAAAAGCCACGTGTATAAGATACACCTGCAAAGGCGG
CACAACCCCAGTGCCACGTTGTGAGTTGGATAGTTGTGGAAAGAGTCAAATGGCTCTCCTCAAG
CGTATTCAACAAGGGGCTGAAGGATGCCCAGAAGGTACCCCATTGTATGGGATCTGATCTGGGG
CCTCGGTGCACATGCTTTACATGTGTTTAGTCGAGGTTAAAAAACGTCTAGGCCCCCCGAACC
ACGGGGACGTGGTTTTCCTTTGAAAAACACGATGATAATATGGCCACAACCATGGTGAGCAAGG
GCGAGGAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCG
TGCAGTGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCGCGCC
GAGGTGAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCTGCTGC
CCGACAACCACTACCTGAGCACCCAGTCCGCCCTGAGCAAAGACCCCAACGA (SEQ ID
NO:15)

Rabbit B-globin PA:
GAAGCGGGATCACATGGTCCTGCTGGAGTTCGTGACCGCCGCCGGGATCACTCTCGGCATGGAC
GAGCTGTACAAGTAAAGCGGCCGCGATCTTTTTCCCTCTGCCAAAAATTATGGGGACATCATGA
AGCCCCTTGAGCATCTGACTTCTGGCTAATAAAGGAAATTTATTTTCATTGCAATAGTGTGTTG
GAATTTTTTGTGTCTCTCACTCGGAAGGACATATGGGAGGGCAAATCATTTAAAACATCAGAAT
GAGTATTTGGTTTAGAGTTTGGCAACATATGCCATATGCTGGCTGCCATGAACAAAGGTGGCTA
TAAAGAGGTCATCAGTATATGAAACAGCCCCCTGCTGTCCATTCCTTATTCCATAGAAAAGCCT
TGACTTGAGGTTAGATTTTTTTATATTTTGTTTTGTGTTATTTTTTCTTTAACATCCCTAAA
ATTTTCCTTACATGTTTTACTAGCCAGATTTTTCCTCCTCCTGACTACTCCCAGTCATAGCT
GTCCCTCTTCTCTTATGAAGATCCCTCGACCTGCAGCCCAAGCTTGGCGTAAT (SEQ ID
NO:16)

M13-rev:
CATGGTCATAGCTGTTTCCTGTGTGA (SEQ ID NO:17)

*Fig. 6D*

LacO:
AATTGTTATCCGCTCACAATTCCACACAACATACGAGCCGGAAGCATAAAGTGTAA
AGCCTGGG
GTGCCTAATGAGTGAGCTAACTCACATTAATTGCGTTGCGCTCACTGCCCGCTTTCC
AGTCGGG
AAACCTGTCGTGCCAGCGGATCCGCATCTCAATTAGTCAGCAACCATAGTCCCGCCC
CTAACTC
CGCCCATCCCGCCCCTAACTCCGCCCAGTTCCGCCCATTCTCCGCCCCATGGCTGACT
AATTTT
TTTTATTTATGCAGAGGCCGAGGCCGCCT (SEQ ID NO:18)

PseI, linker:
AAACGGCCGGCCATcgataccgtcgacctcgagggggggccaggtaccagctttgt (SEQ
ID NO:19)

T3:
Tcccttagtgagggttaatgcgcgcttggcgtaat (SEQ ID NO:20)

M13-rev:
Catggtcatagctgttcctgtgta (SEQ ID NO:21)

LacO:
Aattgttatccgctcacaattccacacaacatacgagccggaagcataaagtgtaaagcctggg
gtgcctaatgagtgagctaactcacattaattgcgttgcgctcactgcccgctttccagtcggg
aaacctgtcgtgccagctgcattaatgaatcggccaacgcgcggggagaggcggtttgcgtatt
gggcgctcttccgcttcctcgctcactgactcgctgcgctcggtcgttcggctgcggcgagcgg
tatcagctcactcaaaggcggtaatacggttatccacagaatcaggggataacgcaggaaagaa
catgtgagcaaaaggccagcaaaaggccaggaaccgtaaaaa (SEQ ID NO:22)

ColE1 origin:
Ggccgcgttgctggcgtttttccataggctccgcccccctgacgagcatcacaaaaatcgacgc
tcaagtcagaggtggcgaaacccgacaggactataaagataccaggcgtttccccctggaagct
ccctcgtgcgctctcctgttccgaccctgccgcttaccggatacctgtccgcctttctccctt
gggaagcgtggcgctttctcatagctcacgctgtaggtatctcagttcggtgtaggtcgttcgc
tccaagctgggctgtgtgcacgaaccccccgttcagcccgaccgctgcgccttatccggtaact
atcgtcttgagtccaacccggtaagacacgacttatcgccactggcagcagccactggtaacag
gattagcagagcgaggtatgtaggcggtgctacagagttcttgaagtggtggcctaactacggc
tacactagaaggacagtatttggtatctgcgctctgctgaagccagttaccttcggaaaaagag
ttggtagctcttgatccggcaaacaaaccaccgctggtagcggtggtttttttgtttgcaagca
gcagattacgcgcagaaaaaaaggatctcaagaagatcctttgatcttttctacggggtctgac
gctcagtggaacgaaaactcacgttaagggattttggtcatgagattatcaaaaaggatcttca
cctagatccttttaaattaaaaatgaagttttaaatcaatctaaagtatatatgagtaaacttg
gtctgacagtta (SEQ ID NO:23)

*Fig. 6E*

AmpR:
Ccaatgcttaatcagtgaggcacctatctcagcgatctgtctatttcgttcatccatagttgcc
tgactccccgtcgtgtagataactacgatacgggagggcttaccatctggccccagtgctgcaa
tgataccgcgagacccacgctcaccggctccagatttatcagcaataaaccagccagccggaag
ggccgagcgcagaagtggtcctgcaactttatccgcctccatccagtctattaattgttgccgg
gaagctagagtaagtagttcgccagttaatagtttgcgcaacgttgttgccattgctacaggca
tcgtggtgtcacgctcgtcgtttggtatggcttcattcagctccggttcccaacgatcaaggcg
agttacatgatcccccatgttgtgcaaaaaagcggttagctccttcggtcctccgatcgttgtc
agaagtaagttggccgcagtgttatcactcatggttatggcagcactgcataattctcttactg
tcatgccatccgtaagatgcttttctgtgactggtgagtactcaaccaagtcattctgagaata
gtgtatgcggcgaccgagttgctcttgcccggcgtcaatacgggataataccgcgccacatagc
agaactttaaaagtgctcatcattggaaaacgttcttcggggcgaaaactctcaaggatcttac
cgctgttgagatccagttcgatgtaacccactcgtgcacccaactgatcttcagcatcttttac
tttcaccagcgtttctgggtgagcaaaaacaggaaggcaaaatgccgcaaaaaagggaataagg
gcgacacggaaatgttgaatactcatactcttcctttttcaatattattgaagcattatcagg
gttattgtctcatgagcggatacatatttgaatgtatttagaaaaataaacaaatagggggttcc
gcgcacatttccccgaaaagtgccac (SEQ ID NO:24)

*Fig. 6F*

ATGGCTTCCAAGGTGTACGACCCCGAGCAACGCAAACGCATGATCACTGGGCCTCAGTGGTGGGCTCGCTGCAAG
CAAATGAACGTGCTGGACTCCTTCATCAACTACTATGATTCCGAGAAGCACGCCGAGAACGCCGTGATTTTCTGC
ATGGTAACGCTGCCTCCAGCTACCTGTGGAGGCACGTCGTGCCTCACATCGAGCCCGTGGCTAGATGCATCATCCC
TGATCTGATCGGAATGGGTAAGTCCGGCAAGAGCGGGAATGGCTCATATCGCCTCCTGGATCACTACAAGTACCT
CACCGCTTGGTTCGAGCTGCTGAACCTTCCAAAGAAAATCATCTTTGTGGGCCACGACTGGGGGGCTTGTCTGGCC
TTTCACTACTCCTACGAGCACCAAGACAAGATCAAGGCCATCGTCCATGCTGAGAGTGTCGTGGACGTGATCGAGT
CCTGGGACGAGTGGCCTGACATCGAGGAGGATATCGCCCTGATCAAGAGCGAAGAGGGCGAGAAAATGGTGCTT
GAGAATAACTTCTTCGTCGAGACCATGCTCCCAAGCAAGATCATGCGGAAACTGGAGCCTGAGGAGTTCGCTGCC
TACCTGGAGCCATTCAAGGAGAAGGGCGAGGTTAGACGGCCTACCCTCTCCTGGCCTCGCGAGATCCCTCTCGTTA
AGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGA
GTTCGTGAAGGTGAAGGGCCTCCACTTCAGCCAGGAGGACGCTCCAGATGAAATGGGTAAGTACATCAAGAGCTT
CGTGGAGCGCGTGCTGAAGAACGAGCAGCTCGAGAATTCTCACGCGTCTGCAGGATATCAAGCTTCCACCATGGC
CTCCTCCGAGGACGTCATCAAGTTCATGCGCTTCAAGGTGCGCATGGAGGGCTCCGTGAACGGCCACGAGTTCGA
GATCGAGGGCGAGGGCGAGGGCCGCCCCTACGAGGGCACCCAGACCGCCAAGCTGAAGGTGACCAAGGGCGGC
CCCCTGCCCTTCGCCTGGGACATCCTGTCCCCTCAGTTCCAGTACGGCTCCAAGGCCTACGTGAAGCACCCCGCCG
ACATCCCCGACTACTTGAAGCTGTCCTTCCCCGAGGGCTTCAAGTGGGAGCGCGTGATGAACTTCGAGGACGGCG
GCGTGGTGACCGTGACCCAGGACTCCTCCCTGCAGGACGGCGAGTTCATCTACAAGGTGAAGCTGCGCGGCACCA
ACTTCCCCTCCGACGGCCCCGTAATGCAGAAGAAGACCATGGGCTGGGAGGCCTCCACCGAGAGGATGTACCCCG
AGGACGGCGCCCTGAAGGGCGAGATCAAGATGAGGCTGAAGCTGAAGGACGGCGGCCACTACGACGCCGAGGT
CAAGACCACCTACATGGCCAAGAAGCCCGTGCAGCTGCCCGGCGCCTACAAGACCGACATCAAGCTGGACATCAC
CTCCCACAACGAGGACTACACCATCGTGGAACAGTACGAGCGCGCCGAGGGCCGCCACTCCACCGGCGCCACCGC
GGGCCCGGGATCCGCCACCATGCCCACGCTACTGCGGGTTTATATAGACGGTCCCCACGGGATGGGGAAAACCAC
CACCACCACGCAACTGCTGGTGGCCCTGGGTTCGCGCGACGATATCGTCTACGTACCCGAGCCGATGACTTACTGG
CGGGTGCTGGGGCTTCCGAGACAATCGCGAACATCTACACCACACAACACCGCCTCGACCAGGGTGAGATATCG
GCCGGGACGCGGCGGTGGTAATGACAAGCGCCCAGATAACAATGCCTTATGCCGTGACCGACGCCGTTCTGGCT
CCTCATATCGGGGGGAGGCTGGAGCTCACATGCCCCGCCCCCGGCCCTCACCATCTTCCTCGACCGCCATCCCA
TCGCCTTCATGCTGTGCTACCCGGCCGCGCGGTACCTTATGGGCAGCATGACCCCCCAGGCCGTGCTGGCGTTCGT
GGCCCTCATCCCGCCGACCTTGCCCGGCACCAACATCGTGCTTGGGGCCCTTCCGAGGACAGACACATCGACCG
CCTGGCCAAACGCCAGCGCCCCGGCGAGCGGCTGGACCTGGCTATGCTGGCTGCGATTCGCCGCGTTTACGGGCT
ACTTGCCAATACGGTGCGGTATCTGCAGTGCGGCGGGTCGTGGCGGGAGGACTGGGGACAGCTTCGGGGACGG
CCGTGCCGCCCAGGGTGCCGAGCCCCAGAGCAACGCGGGCCCACGACCCCATATCGGGGACACGTTATTTACCC
TGTTTCGGGCCCCCGAGTTGATGGCCCCCAACGGCGACCTGTATAACGTGTTTGCCTGGGCCTTGGACGTCTTGGC
CAAACGCCTCCGTTCCATGCACGTCTTTATCCTGGATTACGACCAATCGCCCGCCGGCTGCCGGGACGCCCTGCTG
CAACTTACCTCCGGGATGGTCCAGACCCACGTCACCACCCCCGGCTCCATACCGACGATATGCGACCTGGCGCGCA
CGTTTGCCCGGGAGATGGGGGAGGCTAACTGA (SEQ ID NO:25)

*Fig. 7*

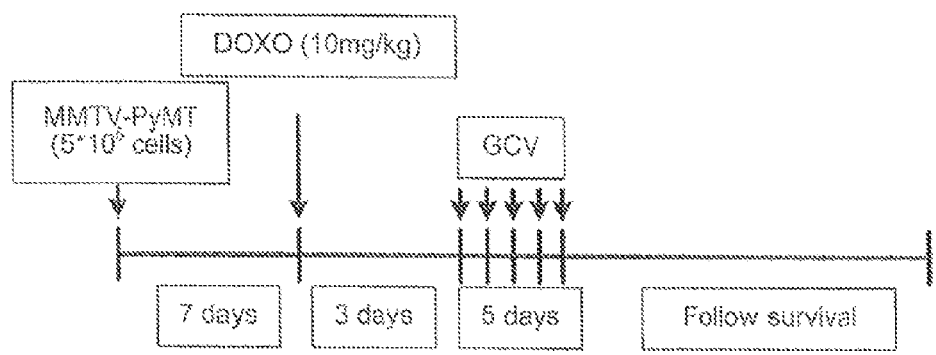
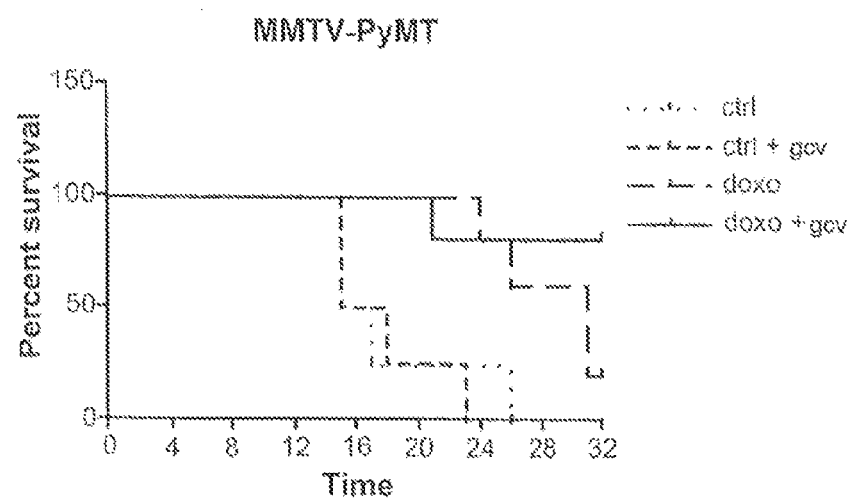
Fig. 13

TRANSGENIC MOUSE FOR DETERMINING THE ROLE OF SENESCENT CELLS IN CANCER

CROSS-REFERENCE TO RELATED APPLICATIONS

This application is a continuation application of U.S. application Ser. No. 13/975,217, filed Aug. 23, 20163, which claims the benefit under 35 U.S.C. § 119(e) to U.S. Provisional Application No. 61/692,622, filed Aug. 23, 2012 and U.S. Provisional Application No. 61/837,090, filed Jun. 19, 2013, which applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200201_408_SEQUENCE_LISTING.txt. The text file is 31 KB, was created on Aug. 21, 2013, and is being submitted electronically via EFS-Web.

BACKGROUND

Technical Field

This disclosure relates to non-human animal models for cancers (solid and liquid), methods for screening therapeutic agents for treating cancer, and methods for treating or preventing cancer.

Description of the Related Art

Cancer includes a broad range of diseases and affects approximately one in four individuals worldwide. In the United States, cancer is the second leading cause of death, accounting for 23% of all deaths. In 2010, nearly 1.5 million people in the United States were diagnosed with one of the ten most common cancers. More than 400,000 people died who had one of these ten cancers. While the five-year relative survival rate for all cancers diagnosed is approximately 68%, treatments and their rates of success vary significantly among cancer types. Given the morbidity and mortality associated with all types of cancers, a need exists in the art for additional methods to identify effective treatments.

BRIEF SUMMARY

Briefly, non-human animal cancer models are provided herein for identifying and characterizing agents useful for therapy and prophylaxis of cancers, including agents useful for diminishing side effects related to cancer therapies and reducing metastatic disease.

In one embodiment, a non-human animal model for cancer is provided herein, which comprises a non-human animal that (a) exhibits a tumor and (b) comprises a transgene selectively expressed by senescent cells. In a specific embodiment, the transgene comprises a senescent cell-specific promoter, and in a more specific embodiment, the promoter is derived from $p16^{Ink4a}$. In certain embodiments, the transgene expresses at least one detectable label, a cytotoxic agent, a cytotoxicity-activating molecule, an RNA, or a combination thereof. The detectable label is selected from the group consisting of (a) luciferase; (b) a red fluorescent protein; (c) a green fluorescent protein; and (d) a luciferase and a red fluorescent protein. In other particular embodiments, the cytotoxicity-activating molecule is selected from the group consisting of a truncated herpes simplex virus thymidine kinase and a FK506-binding protein (FKBP)-caspase fusion polypeptide. Accordingly, in an embodiment, the detectable label is selected from the group consisting of (a) luciferase; (b) a red fluorescent protein; (c) a green fluorescent protein; and (d) a luciferase and a red fluorescent protein; and wherein the cytotoxicity-activating molecule is selected from the group consisting of a truncated herpes simplex virus thymidine kinase and a FKBP-caspase fusion polypeptide. In more specific embodiments, the transgene comprises (a) a $p16^{Ink4a}$ promoter operatively linked to a polynucleotide sequence encoding a fusion polypeptide comprising an FKBP domain and a caspase domain, and to a polynucleotide sequence encoding a green fluorescence protein, or (b) a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene). In a still another specific embodiment, the transgene comprises (a) a $p16^{Ink4a}$ promoter operatively linked to a polynucleotide sequence encoding a FKBP-caspase fusion polypeptide (p16-FKBP-caspase transgene), and to a polynucleotide sequence encoding a green fluorescence protein. In another specific embodiment, a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene). In embodiments of these models, the tumor results at least in part from (1) a genetic modification; (2) a diet modification; (3) a chemical induction; (4) radiation induction; (5) a viral infection; or (6) a combination of any two or more of (1)-(5). In still other embodiments, the tumor results at least in part from a genetic modification, wherein the genetic modification comprises (1) expression of a second transgene; (2) reduced or abrogated expression of an endogenous gene, or (3) a combination thereof. In a specific embodiment, when the genetic modification comprises the second transgene, the second transgene encodes (a) mutant K-Ras or (b) a HER2 under control of a doxycycline-inducible promoter. In other specific embodiments, the chemical induction is a chemotherapy that induces cellular senescence, and in yet another embodiment, the radiation induction induces cellular senescence. In yet another embodiment, the tumor is a carcinogen-inducible skin tumor. In particular embodiments, the tumor is formed by engrafting a plurality of tumor cells into the non-human animal. In one embodiment, a tumor cell line is the source of the tumor cells, and in yet another embodiment, the tumor cells are prepared from a primary culture of tumor cells isolated from a subject. In another embodiment, the tumor is a metastatic tumor.

In another embodiment, a non-human animal model provided herein comprises a transgene that comprises a senescent cell-specific promoter operatively linked to a polynucleotide encoding (a) at least one detectable label, (b) a cytotoxic agent, (c) a cytotoxicity-activating molecule, (d) an RNA, or (e) any combination of (a), (b), (c), and (d); and that exhibits a tumor. In particular embodiments, the transgene comprises a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene) and that has been engrafted with tumor cells, which tumor cells form the tumor in the non-human animal. In other specific embodiments, the transgene comprises a p16$^{Ink4a}$ promoter operatively linked to a polynucleotide sequence encoding a fusion polypeptide comprising an FKBP domain and a caspase domain, and to a polynucleotide sequence encoding a green fluorescence protein, and further comprises a second transgene that encodes (a) mutant K-Ras or (b) HER2 under control of a doxycycline-inducible promoter.

Also provided herein in another embodiment is a method for identifying a therapeutic agent effective for treating or preventing a cancer. In one embodiment, the method comprises (a) administering a candidate therapeutic agent to an animal of any of the animal models described above and herein; (b) (1) determining tumor progression in the treated animal and comparing to tumor progression in an untreated control cancer model animal; or (2) determining the level of suppression of cellular senescence in the treated animal and comparing to the level of cellular senescence in the untreated control animal; wherein (1) suppression of tumor progression or (2) suppression of cellular senescence in the treated animal compared with the untreated animal, identifies an agent effective for treating or preventing cancer. In a specific embodiment, step (b) comprises (1) determining tumor progression exhibited in the treated animal, and comparing to tumor progression exhibited in an untreated control cancer model animal; and (2) determining the level of suppression of cellular senescence in the treated animal and comparing to the level of cellular senescence in the untreated control animal; wherein (1) suppression of tumor progression and (2) suppression of cellular senescence in the treated animal compared with the untreated animal identifies an agent effective for treating or preventing cancer. In a particular embodiment, suppression of cellular senescence comprises suppression of the expression or secretion of one or more senescent cell-associated molecules in the treated animal. In other particular embodiments, suppression of cellular senescence comprises reducing the quantity of senescent cells in the treated animal.

In another embodiment, a therapeutic agent for treating or preventing a cancer is provided herein, which therapeutic agent is identified according to the methods described above and herein.

In one embodiment, a method is provided herein for treating or preventing a cancer in a subject who has a cancer, who is in cancer remission, or who is at risk of developing a recurrence of the cancer, comprising administering to the subject a therapeutic agent identified by any of the methods described above and herein.

In another embodiment, a method for producing the non-human animal of any of the models described above and herein is provided, which method comprises (a) providing a non-human animal that comprises a transgene selectively expressed by senescent cells; and (b) engrafting a plurality of tumor cells into the animal to produce a tumor.

Also provided herein in another embodiment is an isolated cell or cell line derived from any one of the animal models described herein.

In yet another embodiment provided herein is a method for identifying a therapeutic agent effective for treating or preventing a toxic side effect of a cancer therapy, said method comprising: (a) administering a candidate therapeutic agent to an animal of any of the animal models described above and herein; (b) (1) determining at least one physiological effect in the treated animal and comparing the at least one physiological effect in an untreated control cancer model animal; or (2) determining the level of suppression of cellular senescence in the treated animal and comparing to the level of cellular senescence in the untreated control animal; wherein (1) suppression of the toxic side effect or (2) suppression of cellular senescence in the treated animal compared with the untreated animal, identifies an agent effective for treating or preventing a toxic side effect of the cancer therapy.

In another embodiment, a therapeutic agent for treating or preventing a toxic side effect of a cancer therapy is provided herein, which therapeutic agent is identified according to the methods described above and herein.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIGS. 1A and 1B show radiation induces persistent senescent cells in p16-3MR transgenic mice and that GCV treatment leads to depletion of senescent cells and reducing the level of several SASP biomarkers. The transgenic p16-3MR mice were mock irradiated (Ctrl) or irradiated (IR) (7 Gy whole body X-ray), housed for 3 months, and then treated with vehicle or GCV as described herein. Various tissues were isolated (results here shown are for lung tissue) and measured for bioluminescence (FIG. 1A) and the abundance of mRNAs encoding the p16INK4a, mRFP, IL-6 and MMP-3 proteins. Results are shown in arbitrary units (AU) after setting Ctrl levels at 1.

FIGS. 5A-5D provide a listing of an exemplary transgene selectively expressed in senescent cells, the nucleic acid sequence of a pBLUESCRIPT II KS vector containing a p16$^{Ink4a}$ promoter-FKBP-caspase-IRES-GFP nucleic acid construct.

FIGS. 6A-6F provide a listing of the nucleic acid sequences of FIG. 1 with the various vector components and construct components labeled.

FIG. 7 represents an exemplary 3MR transgene sequence.

FIG. 13 presents a schematic (top) of a mammary cancer animal model study in which p16-3MR transgenic mice were injected with MMTV-PyMT cells, followed by treatment with doxorubicin (DOXO) and ganciclovir (GCV). Percent survival of animals was monitored over time (30 days) (bottom).

DETAILED DESCRIPTION

Figure 2:
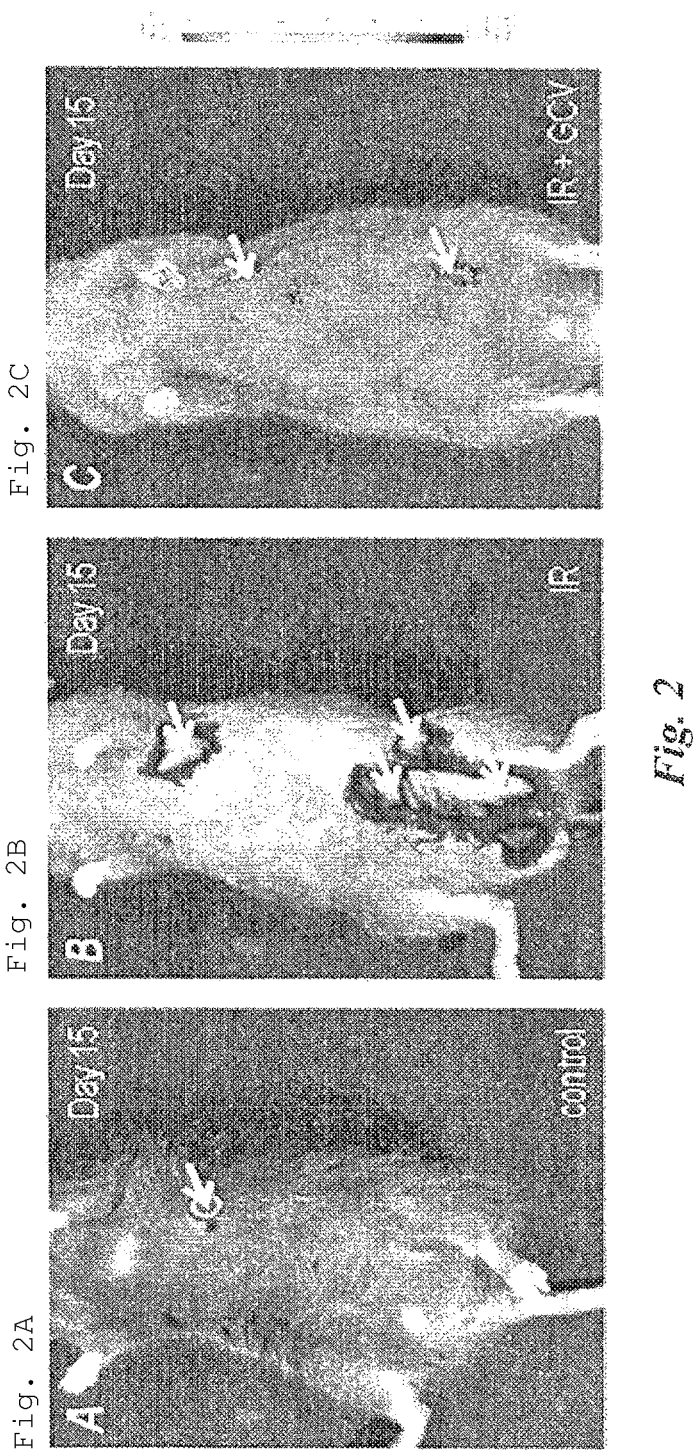
FIGS. 2A-2C show senescent cells induced in p16-3MR transgenic mice by irradiation promote primary and metastatic tumor growth. The transgenic p16-3MR mice were mock-irradiated (Ctrl) or irradiated (IR). Three months later, the irradiated mice were treated with vehicle (IR) or GCV (IR+GCV), then injected with fLUC-expressing B16 melanoma cells into the tail veins. Fifteen days later, bioluminescence of the B16 melanoma cells was measured.

Provided herein are non-human animals and animal models for identifying therapeutic agents that are useful for treating or preventing cancer, including metastatic cancer, by suppressing cellular senescence. The role that senescence plays in various diseases has been the subject of much research and speculation. However, the relationship between senescence and cancer occurrence, tumor progression, and metastasis has not been definitely established, and a need exists for therapeutic agents that suppress cellular senescence and that are useful for treating or preventing cancer. Models described herein may also be useful for identifying agents that can be used as prophylactic agents, that is, reducing the likelihood of occurrence of a cancer. Methods for producing the animal and the animal model, and methods for using the model to identify therapeutic agents are also provided. The therapeutic agents useful for suppressing cellular senescence and for treating or preventing cancer include small molecules, antibodies, polypeptides, peptides, peptibodies, and nucleic acids.

Transgenic Animals with Senescent Cell-Specific Transgene Expression

Certain aspects of the present disclosure employ non-human animals, particularly genetically modified non-human animals, wherein the animals comprise a transgene expressed under the control of a senescent cell-specific promoter. By operably linking a senescent cell-specific promoter of a transgene to a nucleic acid sequence encoding a polypeptide of interest (e.g., a detectable label or cytotoxicity-activating molecule), senescent cells within an animal can be monitored and/or deleted in a controlled and user-determined fashion. In certain embodiments, for example, the present disclosure employs transgenic non-human animals that can be induced to delete senescent cells in vivo at a predetermined and desired point in time, such as at a particular stage of development or disease.

As further described herein, the non-human animals comprising such a transgene may be advantageously crossed with animals which, due to one or more genetic modifications, for example, are known to develop a phenotype associated with a specific disease of interest, such as a cancer, including particular types of tumors (both liquid and solid) and including metastatic cancer. In this way, an animal model may be generated according to the present disclosure in which the role of senescent cells in the initiation, development, progression and/or treatment of a cancer (or tumor) may be evaluated, and in which screening may be carried out in order to identify therapeutic agent that suppress or otherwise advantageously affect senescent cell survival, viability and/or clearance in the context of a cancer in the animal. The animal model and methods described herein also may be used to identify agents that will reduce the occurrence or severity of a side effect associated with cancer therapies such as chemotherapy and radiation.

A senescent cell-specific promoter sequence present within a transgene according to the present disclosure can be essentially any sequence that selectively drives expression of a polypeptide encoded by the transgene or expression of a nucleic acid sequence (e.g., an RNA) in senescent cells, while driving less, little, or no expression of the encoded polypeptide or nucleic acid sequence in non-senescent cells. In certain exemplary embodiments, a senescent cell-specific promoter used in accordance with the present disclosure may include, without limitation, a $p16^{Ink4a}$ promoter sequence, a p21cip promoter sequence, or a Pai1 promoter sequence.

In certain embodiments, the present disclosure provides a non-human animal model comprising a transgene that comprises (1) a senescent cell-specific promoter operatively linked to a polynucleotide encoding (a) at least one detectable label, (b) a cytotoxic agent, (c) a cytotoxicity-activating molecule, (d) an RNA, or (e) any combination of (a), (b), (c) and (d); and that exhibits a tumor.

It will be understood that a senescent cell-specific promoter can be operably (operatively) linked to a nucleic acid sequence encoding any polypeptide of interest. In certain embodiments, the polypeptide of interest is selected from a detectable label, a cytotoxic molecule (e.g., a polypeptide capable of killing a cell in which it is expressed), and a cytotoxicity-activating molecule (e.g., a polypeptide capable of facilitating the killing of a senescent cell in which it is expressed). In certain embodiments, the transgene can be operably linked to an RNA (e.g., siRNA, shRNA, microRNA, and the like, which reduces or abrogates the expression of one or more genes important or essential for senescent cell survival), or a combination thereof. Depending on the polypeptide of interest that is encoded by the transgene, it will be understood that different promoter features may be advantageous or desired. For example, as will be understood, in embodiments wherein a transgene encodes a polypeptide that is directly cytotoxic to cells in which it is expressed, the senescent cell-specific promoter of the transgene will need to be an inducible promoter in order to control the timing of expression of the cytotoxic polypeptide, and thereby control the deletion of senescent cells in the animal. If, on the other hand, a transgene encodes a cytotoxicity-activating polypeptide, the transgene promoter need not be inducible. Rather, the inducibility of the system in this instance relies upon the timing of exposure of the cytotoxicity-activating molecule expressed by senescent cells to its activating agent, as further described below.

Any number of detectable labels may be operably linked to a senescent cell-specific promoter. Many such detectable labels, and the means by which they can be detected, have been described and are well known and established in the art. In some embodiments, the detectable label comprises one or more fluorescent or bioluminescent labels, many of which are well known and established in the art. For example, the fluorescent protein may be any protein that fluoresces and that may be visualized when expressed in senescent cells under the control of a senescent cell-specific promoter as described herein. Illustrative fluorescent proteins can include, for example, green fluorescent protein (GFP), modified or enhanced green fluorescent protein (EGFP), red fluorescent protein (RFP), and various other known fluorescent proteins such as EBFP, EBFP2, Azurite, mKalama1, ECFP, Cerulean, CyPet, YFP, Citrin, Venus, and Wet. Other illustrative fluorescent or bioluminescent proteins include, for example, infrared-fluorescent proteins (IFPs), mRFP1, mCherry, mOrange, DsRed, tdTomato, mKO, TagRFP, mOrange2, maple, TagRFP-T, Firefly Luciferase, *Renilla* Luciferase and Click Beetle Luciferase. Still other illustrative labels can include yellow fluorescent protein, cyan FP, blue FP, red FP and their enhanced versions. It will be understood that essentially any of a number of other luminescent or fluorescent proteins that can emit light can be used in this context.

In certain specific embodiments, a detectable label present within a transgene according to the disclosure is selected from the group consisting of (a) luciferase; (b) a red fluorescent protein; (c) a green fluorescent protein; and (d) a luciferase and a red fluorescent protein.

Any of a number of cytotoxicity-activating molecules may be operably linked to a senescent cell-specific promoter to produce a suitable transgene for use in the context of the present disclosure. Following its expression in a senescent cell-specific fashion, the cytotoxicity-activating molecule is one that is capable of inducing the controllable killing of the senescent cells in which it is expressed upon administration of an activating agent to the transgenic animal. Illustrative examples of cytotoxicity-activating molecules include, but are not limited to herpes simplex virus (HSV) thymidine kinase (TK) polypeptides and FK506 binding protein (FKBP)-caspase fusion polypeptide. FK506 binding protein includes a variant thereof, such as a Phe36Val mutant.

For example, in a specific embodiment, the cytotoxicity-activating molecule encoded by the transgene is a herpes simplex virus (HSV) thymidine kinase (TK) polypeptide (including truncated TK polypeptides) and the activating agent is the pro-drug ganciclovir, which is converted to a toxic moiety that is lethal to the cell in which it is expressed.

In other embodiments, the cytotoxicity-activating molecule encoded by the transgene comprises two or more polypeptide sequences fused together (e.g., a fusion polypeptide). An example of such a fusion polypeptide can be a FKBP-caspase-8 fusion polypeptide. See, e.g., Pajvani et al., *Nat. Med.*, 11:797-803 (2005) and Baker et al., *Nature* 479:232-36 (2011). Such fusion polypeptides may comprise, for example, one or more catalytic domains of human caspase-8 fused to one or more FKBP domains. Following transgene expression, adjacent FKBP molecules in the encoded polypeptide can be activated via forced dimerization using a suitable activating agent, thereby allowing for the regulated ablation of cells in which the fusion polypeptide is expressed. In a specific example, the p20 and p10 domains of human caspase-8 are fused to serial FKBPv (Phe36Val mutant FKBP) domains. Other examples of such polypeptides include, without limitation, a FKBP-caspase-1 fusion polypeptide or FKBP-caspase-3 fusion polypeptide (see, e.g., Mallet et al., *Nat. Biotechnol.* 20:1234-39 (2002)). In these and related embodiments, an illustrative activating agent used to induce cytotoxicity of senescent cells expressing the fusion polypeptide include the compound FK1012 analog AP20187 (referred to herein as AP20187) and related analogs. (See, e.g., U.S. Patent Application Publication No. 2004/0006233, the disclosure of which is incorporated herein by reference). To increase local concentrations of a FKBP-caspase fusion polypeptide, a myristoylation sequence may be included in the transgene to provide membrane attachment for the FKBP-caspase fusion polypeptide.

In this way, administration of a suitable cytotoxicity activating molecule to an animal at a desired time provides an effective means for selectively killing (e.g., by apoptosis) the senescent cells that express the cytotoxicity-activating molecule in the animal. In certain specific embodiments, less than 1%, 5%, 10% or 20% of non-senescent cells of the transgenic mouse are killed when an activating compound is administered to a transgenic mouse comprising a transgene encoding a cytotoxicity activating molecule.

In another embodiment, any of a number of nucleotide sequences encoding small RNAs whose expression affects expression or secretion of senescence cell-associated molecules may be operatively linked to a senescent cell-specific promoter. Such small RNAs include siRNA, shRNA, microRNA and the like (see, Finnegan and Matzke, J. Cell Sci. 226:4689-93, 2003). In certain embodiments, the expression of such small RNAs is under the control of an inducible senescent cell-specific promoter. Upon induction, the expression of the small RNAs down-regulates the expression or secretion of senescent cell-associated molecules of interest.

In some cases, a polypeptide encoded by a transgene of the present disclosure will be engineered to include one or more other elements, such as an affinity tag (e.g., a Flag tag), cellular localization sequence (e.g., myristoylation sequence) or any other desired element of interest.

In light of the above general disclosure, it will be evident that various more specific transgenes and transgenic non-human animals are provided for use herein. For example, in a specific embodiment, the animal model will comprise a transgene wherein a senescent cell-specific promoter directs expression of a detectable label selected from the group consisting of (a) luciferase; (b) a red fluorescent protein; (c) a green fluorescent protein; and (d) a luciferase and a red fluorescent protein; and further directs expression of a cytotoxicity-activating molecule selected from the group consisting of a truncated herpes simplex virus thymidine kinase and a FKBP-caspase fusion polypeptide.

In another specific embodiment, an animal model includes a transgene comprising (a) a $p16^{Ink4a}$ promoter operatively linked to a polynucleotide sequence encoding a FKBP-caspase fusion polypeptide (p16-FKBP-caspase transgene) and to a polynucleotide sequence encoding a green fluorescent protein; or (b) a $p16^{Ink4a}$ promoter operatively linked to a polynucleotide sequence encoding a fusion polypeptide comprising a luciferase, a red fluorescent protein, and a truncated herpes simplex virus thymidine kinase (tTK) (p16-3MR transgene), which may be called herein a trimodal fusion protein (3MR). In more specific embodiments, luciferase is *renilla* luciferase and red fluorescent protein is a monomeric red fluorescent protein. A $p16^{Ink4a}$ promoter may comprise a full-length promoter sequence or may comprise a functional (i.e., operable) truncation (or fragment) thereof (see, e.g., Wang et al. *J. Biol. Chem.* 276:48655-61 (2001)).

The non-human animal models of the present disclosure can be implemented in essentially any type of animal. Most typically, the animal model will be a mammal. In more specific embodiments, illustrative animal models include, but are not limited to, models derived from farm animals such as pigs, goats, sheep, cows, horses, and rabbits, rodents such as rats, guinea pigs, and mice, and non-human primates such as baboons, monkeys, and chimpanzees.

Transgenic nonhuman animal of the present disclosure can include, without limitation, founder transgenic non-human animals as well as progeny of the founders, progeny of the progeny, and so forth, provided that the progeny retain the transgene. The nucleated cells of the transgenic nonhuman animals provided herein can contain a transgene that includes a senescent cell-specific promoter sequence (e.g., a $p16^{Ink4a}$ promoter sequence, or an operable truncation thereof), operably linked to a nucleic acid sequence encoding a polypeptide of interest, such as a polypeptide that comprises a detectable label, a polypeptide capable of killing a cell (e.g., a cytotoxic polypeptide) and/or a polypeptide capable of facilitating the killing of a cell (e.g., a cytotoxicity-activating polypeptide), or a combination thereof.

In the context of transgenic animal production, operably linking a promoter sequence of interest to a nucleic acid sequence encoding a polypeptide of interest is well known and established. This generally involves positioning a regulatory element (e.g., a promoter sequence, an inducible element and/or an enhancer sequence) relative to a nucleic acid sequence encoding a polypeptide in such a way as to permit or facilitate expression of the encoded polypeptide. In the transgenes disclosed herein, for example, a promoter sequence (e.g., a $p16^{Ink4a}$ promoter sequence, or an operable truncation thereof) can be positioned 5' relative to a nucleic acid encoding a polypeptide of interest (e.g., an FKBP-caspase-8 fusion protein or a 3MR fusion protein).

Various techniques known in the art can be used to introduce transgenes into nonhuman animals to produce founder lines, in which the transgene is integrated into the genome. Such techniques include, without limitation, pronuclear microinjection (See, e.g., U.S. Pat. No. 4,873,191), retrovirus mediated gene transfer into germ lines (Van der Putten et al., Proc. Natl. Acad. Sci. USA, 82:6148-1652 (1985)), gene targeting into embryonic stem cells (Thompson et al., Cell 56:313-321 (1989)), electroporation of embryos (Lo, Mol. Cell. Biol., 3:1803-1814 (1983)), and in vitro transformation of somatic cells, such as cumulus or mammary cells, followed by nuclear transplantation (Wilmut et al., Nature, 385:810-813 (1997); and Wakayama et al., Nature, 394:369-374 (1998)). For example, fetal fibroblasts can be genetically modified to contain a desired transgene construct, and then fused with enucleated oocytes. After activation of the oocytes, the eggs are cultured to the blastocyst stage. See, for example, Cibelli et al., Science, 280:1256-1258 (1998). Standard breeding techniques can be used to create animals that are homozygous for the transgene from the initial heterozygous founder animals. Homozygosity is not required, however, as the phenotype can be observed in hemizygotic animals.

Once transgenic non-human animals have been generated, expression of an encoded polypeptide can be assessed using standard techniques. Initial screening can be accomplished by Southern blot analysis to determine whether or not integration of the transgene has taken place. For a description of Southern analysis, see sections 9.37-9.52 of Sambrook et al., 1989, Molecular Cloning, A Laboratory Manual, second edition, Cold Spring Harbor Press, Plainview; NY. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, *Genetic Engineering News,* 12:1 (1992); Guatelli et al., *Proc. Natl. Acad. Sci. USA,* 87:1874-1878 (1990); and Weiss, *Science,* 254:1292-1293 (1991).

Expression of a nucleic acid sequence encoding a polypeptide of interest in senescent cells of transgenic non-human animals can be assessed using techniques that include, without limitation, Northern blot analysis of tissue samples obtained from the animal, in situ hybridization analysis, Western analysis (immunoblot analysis), immunoassays such as enzyme-linked immunosorbant assays, and reverse-transcriptase PCR (RT-PCR).

It will be understood that the present disclosure also provides tissues (e.g., skin, eye, fat, muscle, lung, heart, bone, liver, intestine, kidney, spleen, brain, cartilage, marrow, adrenal glands, ovaries, and testes) and cells or cell lines (e.g., fat cells, preadipocytes, skin or lung fibroblasts, muscle satellite cells, osteoblasts, bone marrow progenitor cells, neuronal progenitor cells, hepatocytes, endothelial cells, chondroblasts, and splenocytes cells) obtained from a transgenic nonhuman animal provided herein. In particular embodiments, the cell line is a tumor cell line established from a tumor present in the animal of the model described herein.

Polypeptide sequences and the encoding polynucleotide sequences for proteins, protein domains and fragments thereof, for proteins described herein such as HSV thymidine kinase (TK) polypeptides, FK506 binding protein (FKBP) and domains thereof, caspase(s) and domains thereof, the detectable fluorescent, bioluminescent polypeptides that are described herein include natural and recombinantly engineered variants. These variants retain the function and biological activity (including enzymatic activities if applicable) associated with the parent (or wildtype) protein. Conservative substitutions of amino acids are well known and may occur naturally in the polypeptide (e.g., naturally occurring genetic variants) or may be introduced when the polypeptide is recombinantly produced. Amino acid substitutions, deletions, and additions may be introduced into a polypeptide using well-known and routinely practiced mutagenesis methods (see, e.g., Sambrook et al. *Molecular Cloning: A Laboratory Manual,* 3d ed., Cold Spring Harbor Laboratory Press, N Y 2001)). Oligonucleotide-directed site-specific (or segment specific) mutagenesis procedures may be employed to provide an altered polynucleotide that has particular codons altered according to the substitution, deletion, or insertion desired. Deletion or truncation variants of proteins may also be constructed by using convenient restriction endonuclease sites adjacent to the desired deletion. Alternatively, random mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra).

Differences between a wild type (or parent) polynucleotide or polypeptide and the variant thereof, may be determined by methods routinely practiced in the art to determine identity, which are designed to give the greatest match between the sequences tested. Methods to determine sequence identity can be applied from publicly available computer programs. Computer program methods to determine identity between two sequences include, for example, BLASTP, BLASTN (Altschul, S. F. et al., *J. Mol. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual,* Altschul, S., et al., NCBI NLM NIH Bethesda, Md.

Assays for determining whether a polypeptide variant folds into a conformation comparable to the non-variant polypeptide or fragment include, for example, the ability of the protein to react with mono- or polyclonal antibodies that are specific for native or unfolded epitopes, the retention of ligand-binding functions, the retention of enzymatic activity (if applicable), and the sensitivity or resistance of the mutant protein to digestion with proteases (see Sambrook et al., supra). Polypeptides, variants and fragments thereof, can be prepared without altering a biological activity of the resulting protein molecule (i.e., without altering one or more functional activities in a statistically significant or biologically significant manner). For example, such substitutions are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified protein for the ability to function in a biological assay, or to bind to a cognate ligand or target molecule.

Non-Human Animals Models for Cancer

The present disclosure provides for transgenic non-human animal models for cancer that comprise a transgene selectively expressed by senescent cells and methods for producing these animal models. Such animal models allow for controlled clearing of senescent cells and monitoring of senescent cells to determine the effect of removal of senescent cells on tumor progression, including tumor growth, number of tumors, and tumor metastasis, and to identify and characterize therapeutic agents.

In the models described herein, a tumor may result, at least in part, from engrafting tumor cells, a genetic modification, a diet modification, chemical induction, radiation induction, virus infection, mechanical induction, or any combination thereof. In one embodiment, a non-human animal models for cancer exhibits a tumor that is engrafted into the animal, such as by injection of tumor cells (i.e., a plurality of tumor cells) either systemically such as by injection (e.g., into the tail vein) or by implantation of tumor cells at a location (e.g., mammary fat pad) or in a particular organ. One source of tumor cells is a cultured cell line, such as any number of cell lines available from cell depositories, such as American Type Culture Collection (Manassas, Va.).

Tumor cells may also be obtained or derived from a tumor and then prepared as a primary culture (i.e., a culture of cells obtained directly from a subject) to engraft into the animals of the model. Typically when the animal, such as a mouse, that is being engrafted is not immunocompromised or immunosuppressed (e.g., a SCID mouse), the source of the tumor is another animal of the same species. Tumor cells include those that are very aggressive (e.g., the melanoma cell line B16), which may be particularly useful for examining metastasis and for identifying agents that inhibit, slow, or prevent metastatic tumors.

Tumor cell lines or a primary culture of tumor cells may be derived or obtained from any one of the many tumor types known and available including solid and liquid tumors. The tumor cells may be derived from a solid tumor, by way of example, without limitation, melanoma, prostate cancer, testicular cancer, breast cancer, brain cancer, pancreatic cancer, colon cancer, thyroid cancer, stomach cancer, lung cancer, ovarian cancer, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer. Liquid tumors from which cell lines or primary cultures may be obtained are classified in the art as those that occur in blood, bone marrow, and lymph nodes and include generally, leukemias (myeloid and lymphocytic), lymphomas (e.g., Hodgkin lymphoma), and melanoma (including multiple myeloma). Leukemias include for example, acute lymphoblastic leukemia (ALL), acute myeloid leukemia (AML), chronic lymphocytic leukemia (CLL), chronic myelogenous leukemia (CML), and hairy cell leukemia. An extensive listing of tumor/cancer types is available at the Internet site, cancer.gov/cancertopics/types/alphalist.

In another embodiment, the animal exhibiting a tumor is exposed to a carcinogen or is infected with a tumor virus or a combination thereof. By way of example, skin carcinogenesis may be induced by a carcinogen (e.g., UV light, chemical carcinogens) (see also, e.g., Slaga et al., *J. Investig. Dermatol. Symp. Proc.* 1:151-56 (1996); Lynch et al., *Toxicologic Pathology* 7:853-64 (2007); Filler et al., *Cold Spring Harbor Protocols* doi:10.1101/pdg.prot4837 (2007)). In other embodiments of the model described herein, the animals may be exposed to a carcinogen and a tumor-promoting agent. In other specific embodiments, a tumor develops in the animal of the model due, at least in part, to activation of an oncogene, which may be either exogenously introduced or may be an endogenous oncogene. Murine tumor viruses that may be used in the animal models described herein include without limitation, murine mammary tumor virus, murine leukemia viruses including Abelson, Gross, Moloney, Friend, and Rauscher; Rous sarcoma virus, and mouse sarcoma virus.

The transgenic cancer models described herein comprise exposing or treating the animals to a senescence stress, such as a chemical or radiation (i.e., non-lethal radiation) that induces senescence. In specific embodiments, the chemical is a chemotherapy drug, which includes a wide range of chemicals. Radiation and chemotherapies are cytotoxic agents that selectively target tumor cells by exploiting differential characteristics of the tumor cell compared with a normal cell. By way of example, differential characteristics and properties of tumor cells include high proliferation rates, hypoxia, aberrant metabolism, less effective repair capacity, and genomic instability.

In other embodiments, use of the cancer model described herein, wherein the transgenic animals comprise a senescent cell specific promoter, comprises examination of endogenously generated senescent cells and the effect of these cells on tumor progression, including metastatic growth. In these embodiments, the animals are not exposed to an exogenous senescence stressor such as chemotherapy or radiation, and senescent cells develop and accumulate endogenously over a longer period of time (e.g., greater than 1 year, including 13, 14, 15, 16, 17, and 18 months after birth).

Radiation therapy comprises use of high-energy radiation to shrink tumors and to kill cancer cells by damaging their DNA. Radiation includes X-rays, gamma rays, and charged particles. The radiation may be delivered by a machine outside the animal body (e.g., external-beam radiation therapy) or the radioactive material placed in the body near cancer cells (i.e., internal radiation therapy). Radiation therapy also includes systemic radiation therapy that uses radioactive substances, such as radioactive iodine, that is administered systemically (for example, parenterally or orally).

Numerous chemotherapeutic drugs are used in the oncology art and include, without limitation, alkylating agents; antimetabolites; anthracyclines, plant alkaloids; and topoisomerase inhibitors. Alkylating agents include by way of example, cisplatin, carboplatin, oxalaplatin, cyclophosphamide, mechlorethamine, chlorambucil, ifosfamide. Exemplary antimetabolites include nucleosides antagonists, such as purines (for example, azathioprine, mercaptopurine) and pyrimidines. Other examples of nucleoside antagonists include 5-fluorouracil, 6-mercaptopurine, arabinosylcytosine, capecitabine, clofarabine, cytarabine, dacarbazine, fludarabine, gemcitabine and nelarabine. *Vinca* alkaloids, include for example, vincristine, vinblastine, vinorelbine, vindesine; taxane and its analogs and derivatives; and podophyllotoxin. Exemplary topoisomerase inhibitors are type I topoisomerase inhibitors such as the camptothecins, for example, irinotecan and topotecan. Other topoisomerase inhibitors are type II topoisomerase inhibitors, for example, amascrine, etoposide, etoposide phosphate, and teniposide, which are semisynthetic derivatives of eipoodophyllotoxins. Cytotoxic antibiotics that are chemotherapeutic agents include without limitation doxorubicin, daunorubicin, valrubicin, idarubicin, epirubicin, bleomycin, plicamycin, and mitomycin. In particular embodiments, the animal model employs doxorubicin, cisplatin, carboplatin, oxalaplatin, or docetaxel (or any paclitaxel).

In the model, animals are monitored for size of the tumor(s) (area and/or volume), tumor progression, tumor growth, tumor multiplicity, tumor colonization, presence and extent of metastasis including location of tumor(s), and overall survival. In certain instances described herein, metastatic growth of a tumor is considered a side effect (i.e., resulting from or caused by) the senescence stress (e.g., chemotherapy or radiotherapy). In certain embodiments, when the cancer animal model is used for determining toxic side effects of a particular cancer therapy or for identifying therapeutic agents useful for ameliorating toxic side effects of a cancer therapy, animals can be monitored for one or more of food consumption, water consumption, body mass, spontaneous activity and behavior, voluntary exercise, oxygen consumption, carbon dioxide production. Tests and assays may also be performed to assess cognitive ability, memory and learning, anxiety, motor function, and the like. By way of non-limiting example, locomoter deficits may be evaluated by determining s tremor, rigidity, bradykinesia, and/or postural instability. Nonmotor symptoms such as olfactory deficits, sleep impairment, and neuropsychiatric disorders can also be evaluated. Methods for detecting, monitoring, quantifying or assessing behavioral deficiencies are also known in the art, including eight-arm radial maze paradigm, non-matching-to-sample task, allocentric place determination task in a water maze, Morris maze test, visuospatial tasks, and delayed response spatial memory task, olfactory novelty test.

The animal models described herein may be used for identifying therapeutic agents useful for ameliorating toxic side effects of a cancer therapy, for example, side effects caused by radiotherapy or chemotherapy (see, e.g., National Cancer Institute web site). In certain embodiments, the methods may be used to identify therapeutic agents that ameliorate acute toxic side effects. Acute toxic side effects include but are not limited to gastrointestinal toxicity (e.g., nausea, vomiting, constipation, anorexia, diarrhea), peripheral neuropathy, fatigue, malaise, low physical activity, hematological toxicity (e.g., anemia), hepatotoxicity, alopecia (hair loss), pain, infection, mucositis, fluid retention, dermatological toxicity (e.g., rashes, dermatitis, hyperpigmentation, urticaria, photosensitivity, nail changes), mouth, gum or throat problems, or any toxic side effect caused by the cancer therapy. In other embodiments, the animal models may be used for identifying therapeutic agents useful for ameliorating toxic side effects of a cancer therapy that are chronic toxic side effects.

In more specific embodiments, the acute toxicity may be an acute toxicity comprising energy imbalance and may comprise one or more of weight loss, endocrine change(s) (e.g., hormone imbalance, change in hormone signaling), and change(s) in body composition. In certain embodiments, an acute toxicity comprising energy imbalance, which relates to decreased or reduced ability of the subject animal to be physically active, as indicated by decreased or diminished expenditure of energy than would be observed in a mouse of the models described herein who did not receive the cancer therapy. By way of non-limiting example, such an acute toxic effect that comprises energy imbalance includes low physical activity. In other particular embodiments, energy imbalance comprises fatigue or malaise.

In other embodiments, methods are provided for identifying therapeutic agents useful for ameliorating toxic side effects of a cancer therapy, which toxic effects are chronic or long term side effects. Chronic toxic side effects typically result from multiple exposures to or administrations of a cancer therapy over a longer period of time. Certain toxic effects appear long after treatment (also called late toxic effects) and result from damage to an organ or system by the therapy. Organ dysfunction (e.g., neurological, pulmonary, cardiovascular, and endocrine dysfunction) has been observed in patients who were treated for cancers during childhood (see, e.g., Hudson et al., *JAMA* 309:2371-81 (2013)). Chronic and/or late toxic side effects that occur in subjects who received chemotherapy or radiation therapy include by way of non-limiting example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease. Accordingly, the animal models described herein may be useful for identifying therapeutic agents that ameliorate these chronic side effects.

In one embodiment, a non-human animal model for cancer as described herein may be further genetically modified to comprise expression of at least one additional transgene (referred to herein as a second transgene) (i.e., dual transgenic model). For example, a second transgene may comprise a nucleotide sequence that encodes an oncogene or other protein associated with tumor initiation and/or progression (e.g., members of the Ras proto-oncogene family (K-Ras, H-Ras, and N-Ras); HER2), which may be a mutant polypeptide (i.e., not comprising the wild-type sequence) that is operatively linked to regulatory expression elements. Alternatively, the genetic modification may include reduced or abrogated expression of an endogenous gene (i.e., gene knockout model), or a combination thereof, which results in or contributes to initiation and/or continued tumor growth, tumor progression, metastasis, or which establishes a tumor in a particular organ (e.g., breast, lung, prostate). In certain instances, controlled expression of the second transgene is desirable and the engineered transgene is therefore inducible. By way of example, a transgene useful in the cancer models described herein may express doxycycline-inducible HER2.

In one embodiment, to create the animal models as described herein, a transgenic parent animal comprising a transgene selectively expressed by a senescent cell (for convenience, referred to as a "first transgenic animal") and a second genetically modified tumor-related parent animal (for convenience, referred to as a "second genetically modified parent animal") may be crossed (or bred) with each other. A transgenic animal comprising a transgene selectively expressed by a senescent cell may be any transgenic animal that comprises a senescent cell-specific promoter within a transgene that selectively drives expression of a polypeptide encoded by the transgene in senescent cells. In certain embodiments, a first transgenic parent animal comprises a transgene comprising a p16$^{Ink4a}$ promoter in frame to express an at least one FKBP domain and at least one caspase domain (e.g., FKBP-caspase fusion polypeptide described herein) or the transgene comprises the p16-3MR transgene described herein. In other embodiments, a parent animal comprises a transgene comprising a p16$^{Ink4a}$ promoter in frame to express a at least one FKBP domain and at least one caspase domain (e.g., FKBP-caspase fusion polypeptide described herein) and comprises the p16-3MR transgene described herein. In still another embodiment, a parent animal comprises a transgene comprising a p16$^{Ink4a}$ promoter in frame to express a at least one FKBP domain and at least one caspase domain (e.g., FKBP-caspase fusion polypeptide described herein) or the transgene comprises the p16-3MR transgene described herein, and which parent animal has a BubR1 hypomorphic (BubR1H/H) genetic background (see, e.g., Baker et al., *Nature* 479:232-236 (2011); International Application Publication No. WO 2012/177927). The second genetically modified parent animal exhibits a tumor or cancer-related genotype or phenotype (e.g., transgenic or knockout model). F1 progeny from a cross between these parental animals are multi-transgenic animals which express the transgenes from each parent. Additional crosses for selection of progeny with heterozygous or homozygous knockout genes may be necessary.

In an alternative embodiment, a multi-transgenic model may be derived by directly introducing a transgene into the germline of another genetically modified animal. For example, a K-Ras transgene or a HER2 transgene can be co-injected into single cell embryos harvested from p16$^{Ink4a}$ promoter-FKBP-caspase transgenic mice. In another example, p16$^{Ink4a}$ promoter-FKBP-caspase transgene may be injected into single cell embryos harvested from a second transgenic mouse (e.g., a K-Ras transgenic mouse or a HER2 transgenic mouse). A person having skill in the art will understand that various injection/recipient embryo combinations may be employed to create a multi-transgenic animal model. Co-injection of different transgenes for generating multi-transgenic mice can be accomplished by these and other methods routinely practiced in the art (see, e.g., Oddo et al., 2003, *Neuron* 39:409-421; U.S. Pat. No. 7,479, 579). In certain specific embodiments, the K-Ras transgenic animal is a K-RasLA1 transgenic animal (see, e.g., Johnson et al., *Nature* 410:1111-16 (2001)).

Non-human animal models for cancer with senescent cell-specific transgene expression created by cross-breeding, transgene injection, or other methods may be confirmed for genotype or transgene expression. Resulting offspring may be genotyped by Southern blot analysis or PCR techniques on DNA extracted from tissue samples (e.g., tail tips or ear punches) using transgene specific probes or primers, respectively. The level of mRNA expression of the transgenes in tissues of transgenic animals may also be assessed using techniques including Northern blot analysis, in situ hybridization, RT-PCR, or real-time PCR. Transgenic proteins may also be detected in tissue samples from transgenic animals using antibodies specific for a polypeptide expressed by the transgene and/or antibodies that are specific for a detectable label that is co-expressed by the transgene, for example.

In another embodiment, for producing the animal model described herein, a knock out or knock-down animal may be crossed with a transgenic animal that expresses a senescent cell-specific transgene. Gene knock-outs allow assessment of in vivo function of a gene that has been altered and used to replace a normal copy. Knock-out modifications include insertion of mutant stop codons, deletion of DNA sequences, or inclusion of recombination elements (lox p sites) recognized by enzymes such as Cre recombinase. Cre-lox system allows for the ablation of a given gene or the ablation of a certain portion of gene sequence. To create a transgenic animal, an altered version of a gene of interest (e.g., a cancer-related gene or a gene encoding a senescent cell associated polypeptide) can be inserted into an animal germ line using standard techniques of oocyte microinjection or transfection, or microinjection into stem cells. For oocyte injection, one or more copies of the altered/mutated gene of interest can be inserted into the pronucleus of a just-fertilized oocyte. The oocyte is then re-implanted into a pseudo-pregnant foster mother. The liveborn progeny can be screened for transgene integrants by analyzing the DNA from tissue samples. Retroviral infection of early embryos may also be performed to insert the altered gene. Embryos are infected during early stages of development to generate a chimera, some of which will lead to germline transmission. Alternatively, if it is desired to inactivate or replace the endogenous gene, mutant alleles may be introduced by homologous recombination into embryonic stem cells. Embryonic stem cells containing a knock out mutation in one allele of the gene being studied are introduced into early embryos. The resultant progeny are chimeras containing tissues derived from both the transplanted ES cells and host cells. Chimeric animals may be mated to assess whether the mutation is incorporated into the germ line. Chimeric animals that are each heterozygous for the knock-out mutation are mated to produce homozygous knock out animals. Mutations in the mouse germline may also be created by injecting oligonucleotides containing the mutation of interest. Gene knock down uses RNAi technology to repress endogenous gene expression in vivo or in vitro. Lentiviral vectors expressing siRNAs or shRNAs may be used to transduce preimplantation mouse embryos for silencing of their specific target genes (see e.g., Tiscornia et al., 2003, *Proc. Natl. Acad. Sci. USA* 100:1844-1848; Singer et al., *Nature Protocols* 1:286-292; Szulc et al., 2006, *Nature Methods* 3:109-116).

Transgenic non-human animal models for cancer as described herein may comprise at least a second transgene, associated with a cancer or tumor, in addition to the first transgene selectively expressed by senescent cells. A second transgene may comprise a wildtype or mutant copy of a human gene of interest.

In certain embodiments, a non-human animal model for cancer as described herein comprises expression of a second transgene, wherein the second transgene comprises a nucleotide sequence encoding a mutant K-Ras or HER2 under control of a doxycycline-inducible promoter, or a combination thereof.

In other certain embodiments, a non-human animal model for cancer as described herein comprises reduced or abrogated expression of an endogenous gene, resulting from heterozygous or homozygous mutation of a gene. In addition to genes that are known or believed to be associated with tumorigenesis (e.g., oncogenes), expression of a gene encoding a senescence cell-associated polypeptide may be reduced or abrogated.

In other certain embodiments, a non-human animal model of cancer disease as described herein may comprise a combination of expression of a second transgene and reduced or abrogated expression of an endogenous gene.

In certain embodiments, the present disclosure provides for an animal model comprising a p16$^{Ink4a}$ promoter, or an operable truncation thereof, operatively (i.e., operably) linked to a polynucleotide sequence encoding at least one FKBP domain and at least one caspase domain (e.g., FKBP-caspase fusion polypeptide (p16-FKBP-caspase transgene)), and to a polynucleotide sequence encoding a green fluorescent protein. Alternatively, a p16$^{Ink4a}$ promoter may be operatively linked to a polynucleotide sequence encoding a fusion polypeptide comprising a luciferase, a red fluorescent protein, and a truncated herpes simplex virus thymidine kinase (p16-3MR transgene); wherein the model further comprises a second transgene comprising a nucleotide sequence encoding mutant K-Ras, doxycycline-inducible HER2, or a combination thereof.

In yet another embodiment, the present disclosure provides for a method of producing a non-human animal model for cancer comprising a non-human animal that exhibits a tumor and comprises a transgene selectively expressed by senescent cells. In another embodiment, a method for producing a non-human animal model for cancer comprises (a) providing an animal comprising the transgene selectively expressed by senescent cells; and (b) breeding the animal of step (a) with an animal comprising a genetic modification associated with cancer to produce a multi-transgenic animal. An animal comprising a genetic modification associated with cancer may be a knockout, knockdown, or transgenic animal. In a specific embodiment, the animal of step (b) is a transgenic animal comprising a transgene encoding mutant K-Ras or that encodes doxycycline inducible HER2. The transgenic animals of the model described herein are in certain embodiments, exposed to a carcinogen, or exposed to a chemical that is a chemotherapy or exposed to radiation. In certain embodiments, the animals are exposed to both chemotherapy and radiation.

Non-human animal models for cancer with senescent cell specific transgene expression, as described herein, are useful in tracking or monitoring senescence cells. For example, animal models comprising transgenes expressing detectable labels may be used in imaging senescent cells, determining ratio of senescent cells in a tissue, and/or monitoring the elimination of senescent cells. In addition, such models may also be used in characterizing drug candidates for treating or preventing cancer, such as the tissue specificity of such candidates. For example, these models expressing detectable labels under the control of senescent cell-specific promoters may be used to determine the tissue type in which a drug candidate suppresses cellular senescence using the detectable labels. Animal models comprising transgenes expressing cytotoxicity-activating molecules allow for titrating the elimination of senescent cells by modulating concentrations of activating agents.

Also contemplated is the use of non-genetic models of cancer may also be induced, at least in part, by chemicals (including chemotherapies), radiation, diet, or mechanical/electrolytic means. Non-human animal models for cancer with senescent cell specific transgene expression, as described herein, may be used to evaluate effects of senescent cell ablation on tumorigenesis and tumor progression, including metastasis. By eliminating senescent cells or effects of senescent cell associated molecules at various times in an animal model for cancer, the role of senescent cells in vivo in promoting tumor growth, progression, and metastasis, for example, may be tested. In certain embodiments, senescent cell ablation may be accomplished by administration of FK1012 analog AP20187, which induces dimerization of membrane-bound myristolylated FKBP-caspase fusion protein expressed in senescent cells via the $p16^{Ink4a}$ promoter, resulting in activation of apoptosis. In other embodiments, when the cytotoxicity activating molecule is Herpes simplex truncated thymidine kinase, senescent cell ablation may be accomplished by administration of ganciclovir. Senescent cell ablation may also be performed by candidate therapeutic agents.

In certain embodiments, also provided herein are isolated cells and/or cell lines derived from the non-human animal models for cancer with senescent cell specific transgene expression, as described herein. Primary cell cultures derived from the non-human animal models or continuous cell lines may be generated from the non-human animal models. Methods for deriving a continuous cell line from transgenic animals are known in the art (see, e.g., Small et al., 1985, Mol. Cell. Biol. 5:642-648; Morgan et al., 1994, Dev. Biol. 162:486-98; U.S. Pat. No. 5,814,716; U.S. Pat. No. 6,583,333; U.S. Pat. No. 6,825,394). Isolated cells or cell lines may be derived from any organ, tissue, or bodily fluid from the animal model. The cells and cell lines may be cultured under conditions and in media appropriate to maintain the health and propagation of the cells, as desired, using techniques and procedures routinely practiced in the cell culture art. These isolated cells or cell lines may be used to identify and characterize therapeutic agents that suppress cellular senescence and that are useful for treating or preventing cancer.

Methods for Identifying Therapeutic Agents

The non-human animal models and cell lines derived therefrom as described herein may be used to identify therapeutic agents effective for treating or preventing cancer. Such animal models and cell lines are particularly useful for identifying therapeutic agents effective for treating or preventing cancer by suppressing cellular senescence. Therapeutic agents include small molecules, antibodies, antigen-binding fragments, polypeptides, peptides, peptibodies, hormones, and nucleic acids.

In one embodiment, the present disclosure provides a method for identifying a therapeutic agent effective for treating or preventing cancer (or for inhibiting or reducing tumor progression or metastasis), comprising: (a) administering a candidate therapeutic agent to the animal of any of the animal cancer models described herein to provide a treated animal, and (b) determining tumor progression exhibited in the treated animal, and comparing to tumor progression exhibited in an untreated control cancer model animal. The suppression of tumor progression in the treated animal compared with the untreated animal identifies an agent effective for treating or preventing cancer.

In another embodiment, a method is provided for identifying a therapeutic agent effective for treating or preventing a cancer, comprises (a) administering a candidate therapeutic agent to the animal of any of the cancer animal models described herein to provide a treated animal; and (b) (1) determining tumor progression exhibited in the treated animal, and comparing to tumor progression exhibited in an untreated control cancer model animal; or (2) determining the level of suppression of cellular senescence in the treated animal and comparing to the level of cellular senescence in the untreated control animal; wherein (1) suppression of tumor progression and (2) suppression of cellular senescence in the treated animal compared with the untreated animal, identifies an agent effective for treating or preventing cancer. Specific embodiments of the methods are described in greater detail herein.

As described herein, candidate therapeutic agents are screened in the animal model to identify agents that decrease, reduce, inhibit, or prevent tumor cell proliferation and are thereby useful for treating and/or preventing a cancer (which may be a metastatic cancer). A therapeutic agent useful for treating and/or preventing a cancer is capable of preventing, inhibiting, stabilizing, and/or reversing proliferation, colonization, differentiation and/or development of abnormally proliferating cells.

Tumor progression may be monitored by any one or more of the following measures: size and location of a tumor, extent of metastasis, symptomatology of an animal, or by length of time for tumor progression, and/or survival of the animal, including whether length of time to death or to when the animal appears moribund is increased compared to the appropriate control. Suppressing cellular senescence may comprise one or both of (1) selectively destroying or facilitating selective destruction of a senescent cell; and (2) inhibiting expression or secretion of one or more senescence cell-associated molecules by the senescent cell. The model may also be used in the methods described herein for characterizing a therapeutic agent that suppresses cellular senescence and that reduces or inhibits tumor proliferation, which may be determined by any one or more of tumor size, tumor growth, tumor number, and extent of metastasis (i.e., location of tumor cells if not at the tumor colonization site or number of tumors that have spread from the site of colonization). In certain embodiments, the effectiveness of an agent is determined by survival of the treated animals. A person skilled in the art readily understands that determination of tumor progression, morbidity, or mortality in treated animals is determined by comparison to untreated animals.

In one embodiment, the non-human animal models and cell lines derived therefrom as described herein may be used to identify therapeutic agents that when administered to a subject suppress cellular senescence in the treated subject and alter the phenotype of the disease (i.e., decrease or reduce one or more phenotypic characteristics, parameters, symptoms, or markers of the disease to be treated).

As used herein and in the art, the terms cancer or tumor are clinically descriptive terms which encompass diseases typically characterized by cells that exhibit abnormal cellular proliferation. The term cancer is generally used to describe a malignant tumor or the disease state arising from the tumor. Alternatively, an abnormal growth may be referred to in the art as a neoplasm. The term tumor, such as in reference to a tissue, generally refers to any abnormal tissue growth that is characterized, at least in part, by excessive and abnormal cellular proliferation. A tumor may be metastatic and capable of spreading beyond its anatomical site of origin to other areas throughout the body of the subject.

In another embodiment of the animal models described herein, the present disclosure provides a method for identifying a therapeutic agent effective for treating or preventing (ameliorating) a toxic side effect of a cancer therapy comprising: (a) administering a candidate therapeutic agent to the animal of any of the animal cancer models described herein to provide a treated animal, and (b) determining at least one physiological effect (which may be detected by macroscopic observation of the animal (i.e., symptomatology) or by measuring a parameter (e.g., respiration parameters, food intake, water intake, resting time, time of physical activity, calorie expenditure) exhibited in the treated animal, and comparing to the same at least one physiological effect exhibited in an untreated control cancer model animal. The suppression of tumor progression in the treated animal compared with the untreated animal identifies an agent effective for treating or preventing (ameliorating) a toxic side effect.

In another embodiment, a method is provided for identifying a therapeutic agent effective for treating or preventing (ameliorating) a toxic side effect of a cancer therapy, comprises (a) administering a candidate therapeutic agent to the animal of any of the cancer animal models described herein to provide a treated animal; and (b) (1) determining at least one physiological effect (which may be detected by macroscopic observation of the animal (i.e., symptomatology) or by measuring a parameter (e.g., respiration parameters, food intake, water intake, resting time, time of physical activity, calorie expenditure) exhibited in the treated animal, and comparing to the same at least one physiological effect exhibited in an untreated control cancer model animal; or (2) determining the level of suppression of cellular senescence in the treated animal and comparing to the level of cellular senescence in the untreated control animal; wherein (1) suppression of tumor progression and (2) suppression of cellular senescence in the treated animal compared with the untreated animal, identifies an agent effective for treating or preventing (ameliorating) a toxic side effect. Specific embodiments of the methods are described in greater detail herein.

A therapeutic agent that selectively destroys a senescent cell or facilitates selective destruction of a senescent cell kills, removes, clears, reduces viability, or decreases survival of a senescent cell (i.e., in some manner reduces the quantity of viable senescent cells in the animal or in the cell-based assay) in a statistically significant or biologically significant manner when compared with the capability of the therapeutic agent to kill, remove, clear, reduce viability, or decrease survival of a non-senescent cell. Such therapeutic agents may therefore be useful for treating or preventing a cancer in a subject to whom the agent is administered. In certain embodiments, selective destruction of senescent cells in the animal model described herein can be monitored by determining the level of a detectable label or labels that is expressed in senescent cells of the animal.

In one embodiment, a method is provided for identifying a therapeutic agent that inhibits tumor cell proliferation by suppressing cellular senescence. Candidate therapeutic agents may be administered to a test animal of any one of the animal models described herein. In particular embodiments, the test animal is a transgenic animal comprising a transgene that includes a nucleic acid that allows for controlled clearance of senescence cells (e.g., $p16^{ink4a}$ positive senescent cells). In a specific embodiment, a transgenic non-human animal as described herein, such as a transgenic mouse that comprises the transgene called herein INK-ATTAC (see FIG. 5) or the transgene p16-3MR, is used in the method. To identify a therapeutic agent or to confirm the activity of a candidate therapeutic agent, the candidate agent is administered to the transgenic animal prior to, concurrent with, or subsequent to engrafting the animal with tumor cells. In certain embodiments, the phenotype of the disease, in this instance cancer (i.e., the presence of detectable tumor cells), is induced by aging of the non-human animal, a genetic modification, diet modification, chemical induction, or any combination thereof, which also contributes to or causes cells to enter senescence.

In one embodiment, the animal models comprise chemical induction or radiation induction. The chemical induction or radiation induction induces or promotes cellular senescence and may be referred to as a senescence stress or stressor. Also as described herein, in certain embodiments, cellular senescence may be induced by administering to the animal a cell (or biological) damaging therapy (i.e., a senescence stress or stressor), which includes cytotoxic and genotoxic (i.e., DNA damaging) therapies, such as by way of non-limiting example, irradiation, a chemotherapeutic drug, and an agent that induces endogenous oncogene expression. The cell-damaging therapy that induces cellular senescence, the tumor cells (if engrafted and not endogenously induced), and the candidate therapeutic agent may be administered to the animal in any order. In certain embodiments, the cell-damaging therapy is administered first, followed by the candidate therapeutic agent, which is then followed by engraftment of the tumor cells. In other embodiments, the tumor cells are engrafted first, followed by administration of the cell damaging therapy, which is then followed by administration of the therapeutic agent. In other specific embodiments, the cell-damaging therapy and therapeutic agent are administered concurrently (for example, within 1-2 hours). The age of the animals used in the animal models described herein, quantity of candidate therapeutic agents, cell damaging therapy if used, quantity of tumor cells and administration regimen can be readily determined by persons skilled in the art using routinely practiced techniques and procedures in the art.

In more specific embodiments, a method for identifying an agent comprises inducing tumor formation (i.e., engrafting tumor cells or permitting a tumor to develop endogenously) followed by administration of the damaging therapy (e.g., senescence stress) and the candidate therapeutic agent in either order. Accordingly, in a specific embodiment, animals in which a tumor has been induced or is present, the damaging therapy is administered followed by the candidate agent; in other embodiments, the candidate agent is administered prior to the damaging therapy. In still other embodiments, the damaging therapy and the candidate agent are administered prior to induction or development of the tumor. In more specific embodiments, the damaging therapy is administered prior to the candidate agent, and in other specific embodiments, the candidate agent is added prior to the damaging therapy. As described herein, the animal cancer models are useful for determining whether an agent is capable of suppressing cellular senescence and determining whether the suppression of cellular senescence inhibits colonization of a tumor or tumor progression, including whether the agent inhibits or reduces metastasis.

A person skilled in the art will also readily appreciate that when performing analyses in animal models, appropriate controls are included. By way of non-limiting example, a group of animals will receive a candidate therapeutic agent (or a composition or a vehicle comprising the agent), which animals may be referred to as treated animals. Another group of animals will receive vehicle only or another appropriate control composition that does not include an anti-tumor agent. A third group may receive a therapeutic agent known to provide the desired effect in the animal (e.g., an agent that suppresses cellular senescence and that inhibits tumor proliferation, reduces tumor size, and/or inhibits metastasis). In certain embodiments, a group of animals is treated with a known agent that inhibits tumor proliferation, reduces tumor size, and/or inhibits metastasis. The phenotype (or one or more phenotypic markers or characteristics) of the treated animal is then compared with the phenotype of the control animals that do not receive the candidate agent.

Positive control animal groups may also be included in the methods for identifying a therapeutic agent. By way of example, the animal models described herein comprise a transgene that includes a senescent cell specific promoter that is operatively linked to a polypeptide (which may be a fusion polypeptide) comprising a cytotoxicity—activating molecule (e.g., HSV truncated TK, FKBP-caspase polypeptide). Accordingly, when cells are induced to senescence by normal aging or by any one of the molecules, methods, or genetic modifications described herein, the fusion polypeptide expresses the cytotoxicity-activating molecule. By way of example, a positive control animal model group that expresses the FKBP-caspase polypeptide (e.g., an INK-ATTAC animal) may be treated with AP20187 and related analogs, for example, which results in senescent cell destruction. By way of additional example, a transgenic animal (e.g., a P16-3MR animal) that expresses a fusion polypeptide comprising HSV truncated TK can be administered a prodrug, such as ganciclovir, that is activated when the truncated thymidine kinase is expressed in senescent cells, resulting in destruction of the senescent cell.

As described herein, a desirable therapeutic agent is an agent that suppresses cellular senescence resulting in inhibition of tumor proliferation in a statistically significant manner. Tumor proliferation may be determined by tumor size, which can be measured in various ways familiar to a person skilled in the tumor animal model art, such as by palpation or measurement of the volume or area of a tumor (which may be performed postmortem), location(s) of the tumor (e.g., to determine if tumor cells have metastasized from the primary tumor site (i.e., the site where the tumor cells initially colonize). The effect of the therapeutic agent on tumor proliferation may also be evaluated by examining differentiation of the tumor cells.

Suppressing cellular senescence may comprise one or both of (1) selectively destroying or facilitating selective destruction of a senescent cell; and (2) inhibiting expression or secretion of one or more senescence cell-associated molecules including senescence-cell associated polypeptides (e.g., cytokines, chemokines, growth factors) by the senescent cell.

Determining the effectiveness of a therapeutic agent or a candidate therapeutic agent to inhibit tumor progression or to suppress senescence as described herein in an animal model is typically performed using one or more statistical analyses with which a skilled person will be familiar. By way of example, statistical analyses such as two-way analysis of variance (ANOVA) may be used for determining the statistical significance of differences between animal groups treated with an agent and those that are not treated with the agent (i.e., negative control group). Statistical packages such as SPSS, MINITAB, SAS, Statistika, Graphpad, GLIM, Genstat, and BMDP are readily available and routinely used by a person skilled in the animal art.

Cellular senescence is a stable and essentially permanent arrest of cell proliferation, which is accompanied by extensive changes in gene expression. Many types of cells, both normal cells and tumor cells, undergo senescence in response to stress. As described in the art, the phenotype of a senescence cell, such as the phenotype referred to as senescence associated secretory phenotype (SASP), is typified by secretion of numerous cytokines (e.g., inflammatory cytokines), growth factors, extracellular matrix components (ECM) and ECM-degrading enzymes, and proteases, for example. While proliferative arrest poses a formidable barrier to tumor progression (see, e.g., Campisi, *Curr. Opin. Genet. Dev.* 21:107-12 (2011); Campisi, *Trends Cell Biol.* 11:S27-31 (2001); Prieur et al., *Curr. Opin. Cell Biol.* 20:150-55 (2008)), and molecules secreted by senescent cells can stimulate tissue repair (see, e.g., Adams, *Molec. Cell* 36:2-14 (2009); Rodier et al., *J. Cell Biol.* 192:547-56 (2011)), senescent cells also secrete molecules that can cause inflammation (see, e.g., Freund et al., *Trends Mol. Med.* 16:238-46 (2010); Davalos et al., *Cancer Metastasis Rev.* 29:273-83 (2010)). Low-level, chronic inflammation is a hallmark of aging tissues, and inflammation is a major cause of, or contributor to, virtually every major age-related pathology, including cancer (Ferrucci et al., 2004, *Aging Clin. Exp. Res.* 16:240-243; Franceschi et al., 2007, Mech. Ageing Dev. 128:192-105; Chung et al., 2009, *Ageing Res. Rev.* 8:18-30; Davalos et al., 2010, *Cancer Metastasis Rev.* 29:273-283; Freund et al., 2010, *Trends Molec. Med.* 16:238-248). Thus, senescent cells, which increase with age and at sites of age-related pathology, might stimulate local chronic inflammation and tissue remodeling, thereby fueling both the degenerative diseases of aging as well as age-related cancer.

A senescent cell may exhibit any one or more of the following characteristics. (1) Senescence growth arrest is essentially permanent and cannot be reversed by known physiological stimuli. (2) Senescent cells increase in size, sometimes enlarging more than twofold relative to the size of non-senescent counterparts. (3) Senescent cells express a senescence-associated β-galactosidase (SA-β-gal), which partly reflects the increase in lysosomal mass. (4) As described herein, most senescent cells express p16INK4a, which is not commonly expressed by quiescent or terminally differentiated cells. (5) Cells that senesce with persistent DNA damage response signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction—induced foci (TIF). (6) Senescent cells express and may secrete molecules called herein senescent cell-associated molecules, which in certain instances may be dependent on persistent DDR signaling for their expression. (7) The nuclei of senescent cells lose structural proteins such as Lamin B1 or chromatin-associated proteins such as histones and HMGB1. See, e.g., Freund et al., *Mol. Biol. Cell* 23:2066-75 (2012); Davalos et al., *J. Cell Biol.* 201:613-29 (2013); Ivanov et al., *J. Cell*

*Biol.* DOI: 10.1083/jcb.201212110, page 1-15; published online Jul. 1, 2013; Funayama et al., *J. Cell Biol.* 175:869-80 (2006)).

Senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities. Without wishing to be bound by theory, the negative effects of senescent cells are believed to be the result of, at least in part, the secretion of pro-inflammatory cytokines, chemokines, growth factors, and proteases that comprise the SASP of a senescent cell (see, e.g., Coppe et al., PLoS Biol. 6:2853-68 (2008)). Senescent cell-associated molecules that comprise the SASP can disrupt normal tissue structure and function and stimulate malignant phenotypes in pre-malignant or non-aggressive cancer cells (see, e.g., Coppe et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005). ECM associated factors include inflammatory proteins and mediators of ECM remodeling and which are strongly induced in senescent cells (see, e.g., Kuilman et al., *Nature Reviews* 9:81-94 (2009)). Other senescent cell-associated molecules include extracellular polypeptides (proteins) described collectively as the DNA damage secretory program (DDSP) (see, e.g., Sun et al., *Nature Medicine* published online 5 Aug. 2012; doi:10.1038/nm.2890). Senescent cell-associated proteins also include cell surface proteins (or receptors) that are expressed on senescent cells, which include proteins that are present at a detectably lower amount or are not present on the cell surface of a non-senescent cell.

Senescence cell-associated molecules include secreted factors which may make up the pro-inflammatory phenotype of a senescent cell (e.g., SASP). These factors include, without limitation, GM-CSF, GROα, GROα,β,γ, IGFBP-7, IL-1α, IL-6, IL-7, IL-8, MCP-1, MCP-2, MIP-1α, MMP-1, MMP-10, MMP-3, Amphiregulin, ENA-78, Eotaxin-3, GCP-2, GITR, HGF, ICAM-1, IGFBP-2, IGFBP-4, IGFBP-5, IGFBP-6, IL-13, IL-1β, MCP-4, MIF, MIP-3α, MMP-12, MMP-13, MMP-14, NAP2, Oncostatin M, osteoprotegerin, PIGF, RANTES, sgp130, TIMP-2, TRAIL-R3, Acrp30, angiogenin, Axl, bFGF, BLC, BTC, CTACK, EGF-R, Fas, FGF-7, G-CSF, GDNF, HCC-4, 1-309, IFN-γ, IGFBP-1, IGFBP-3, IL-1 R1, IL-11, IL-15, IL-2R-α, IL-6 R, I-TAC, Leptin, LIF, MMP-2, MSP-a, PAI-1, PAI-2, PDGF-BB, SCF, SDF-1, sTNF RI, sTNF RII, Thrombopoietin, TIMP-1, tPA, uPA, uPAR, VEGF, MCP-3, IGF-1, TGF-β3, MIP-1-delta, IL-4, FGF-7, PDGF-BB, IL-16, BMP-4, MDC, MCP-4, IL-10, TIMP-1, Fit-3 Ligand, ICAM-1, Axl, CNTF, INF-γ, EGF, BMP-6. Additional identified factors, which include those sometimes referred to in the art as senescence messaging secretome (SMS) factors, some of which are included in the listing of SASP polypeptides, include without limitation, IGF1, IGF2, and IGF2R, IGFBP3, IDFBP5, IGFBP7, PA11, TGF-β, WNT2, IL-1α, IL-6, IL-8, and CXCR2-binding chemokines. Cell-associated molecules also include without limitation the factors described in Sun et al., *Nature Medicine*, supra, and include, for example, products of the genes, MMP1, WNT16B, SFRP2, MMP12, SPINK1, MMP10, ENPP5, EREG, BMP6, ANGPTL4, CSGALNACT, CCL26, AREG, ANGPT1, CCK, THBD, CXCL14, NOV, GAL, NPPC, FAM150B, CST1, GDNF, MUCL1, NPTX2, TMEM155, EDN1, PSG9, ADAMTS3, CD24, PPBP, CXCL3, MMP3, CST2, PSG8, PCOLCE2, PSG7, TNFSF15, C17orf67, CALCA, FGF18, IL8, BMP2, MATN3, TFP1, SERPINI 1, TNFRSF25, and IL23A. Senescent cell-associated proteins also include cell surface proteins (or receptors) that are expressed on senescent cells, which include proteins that are present at a detectably lower amount or are not present on the cell surface of a non-senescent cell.

A therapeutic agent of interest includes an agent that selectively destroys or facilitates selective destruction of a senescent cell and/or in some manner is effective for inhibiting expression or secretion of a senescence cell-associated molecule, including a senescence cell-associated protein, or a protein that is present on the cell surface of a senescent cell. Therapeutic agents of interest also include agents that inhibit transcription or translation of a senescence cell-associated polypeptide (protein), or a protein that is present on the cell surface of a senescent cell. Such agents are useful for treating or preventing cancer.

A therapeutic agent that "selectively" destroys or facilitates "selective" destruction of a senescent cell is an agent that preferentially (or to a greater degree) destroys or facilitates destruction or facilitates clearance of a senescent cell. In other words, the therapeutic agent destroys or facilitates destruction of a senescent cell in a biologically, clinically, and/or statistically significant manner compared with its capability to destroy or facilitate destruction of a non-senescent cell. By way of non-limiting example, the therapeutic agent may directly or indirectly kill a senescent cell by disrupting the integrity of the cell membrane; inhibiting one or more metabolic processes in the cell; enhancing or stimulating a signaling pathway that leads to apoptosis or necrosis of the senescent cell; disrupt transcription or translation of genes or proteins, respectively, necessary for cell survival; and/or binding to the senescent cell to facilitate clearance or removal of the cell, for example, clearance by immune cells. As described herein, the presence of senescent cells in the transgenic animals comprising a senescent cell specific promoter can be monitored and determined by expression or presence (or lack of expression or presence) of one or more detectable labels (e.g., a luciferase or fluorescent polypeptide) that is operatively linked to the promoter.

In particular embodiments, the level of transcription, expression, or secretion can be determined for one or more senescence cell-associated polypeptides. An effective therapeutic agent that suppresses cellular senescence reduces or inhibits expression, secretion, or production of a senescence cell-associated polypeptide in a statistically significant or biologically significant manner compared to the appropriate controls. Proteins that comprise senescence cell-associated molecules and methods for evaluating expression and secretion of SASP proteins are described in the art (see, e.g., Freund et al., *Trends Mol. Med.* 16:283-46 (2010) and references cited therein; Sun et al., *Nature Med.*, published online 5 Aug. 2012; doi: 10.1038/nm.2890). Senescent cells may also be detected by determining the presence and level of senescence-associated-β-galactosidase (SA-β-Gal). A decrease or reduction in the level of expression or secretion of one or more senescence cell-associated molecules (including senescence cell-associated polypeptides), SA-β-Gal, or reduction in the quantity of senescent cells and a reduction in proliferation phenotype in the test animal compared with the control animal identifies a therapeutic agent.

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta gal (SA-Bgal) (see, e.g., Dimri et al., *Proc. Natl. Acad. Sci. USA* 92: 9363-9367 (1995). The presence of the senescent cell-associated polypeptide p16 can be determined by any one of numerous immunochemistry methods practiced in the art, such as immunoblotting analysis. Expression of p16 mRNA in a cell can be measured by a variety of techniques practiced in the art including quantitative PCR. The presence and level of senescence cell associated polypeptides (e.g., polypeptides of the SASP) can be determined by using automated and high throughput assays, such as an automated Luminex array assay described in the art (see, e.g., Coppe et al., *PLoS Biol* 6: 2853-68 (2008)). For monitoring a DNA damage response, the various DNA damage response indicators can be detected, for example, according to the method of Rodier et al., *Nature Cell Biol* 11: 973-979 (2009)).

Therapeutic agents of interest include those that are activated or that are pro-drugs which are converted to the active form by enzymes that are expressed at a higher level in senescent cells than in non-senescent cells. Other therapeutic agents of interest include those that bind to proteins on the cell surface of a cell that are present exclusively or at a greater level on senescent cells compared with non-senescent cells (see, e.g., International Patent Application Publication No. WO 2009/085216). In certain embodiments, a therapeutic agent that specifically binds to a senescent cell has at least 2, 4, 8, 10, 50, 100, or 1000 fold greater affinity for a senescent cell than for a non-senescent cell, or in certain embodiments, the therapeutic agent does not detectably bind to a non-senescent cell. A protein present at a greater level on a senescent cell than on a non-senescent cell may be a protein that is typically an intracellular protein and not detectable on the cell surface of a non-senescent cell. Other therapeutic agents of interest that suppress cellular senescence include those that are activated by a metabolic process that occurs more frequently or at a higher rate in senescent cells than in a non-senescent cells.

Potential therapeutic agents may be identified from "libraries" or collections of compounds, compositions, or molecules. A source of small molecules, peptides, and oligonucleotides includes combinatorial libraries that may be screened to identify a therapeutic agent useful for treating of preventing a cancer. Other exemplary libraries comprise peptides or polypeptides that represent a complementarity determining region (CDR) of an antibody.

In one embodiment, therapeutic agents useful for treating or preventing cancer are small organic molecules that suppress cellular senescence. A small molecule compound of interest may be further derivatized, either randomly or by SAR, to obtain compounds with improved anti-cellular senescence activity and more effective anti-cancer agents. Small organic molecules typically have molecular weights less than $10^5$ daltons, less than $10^4$ daltons, or less than $10^3$ daltons.

A therapeutic agent includes an antibody, or antigen-binding fragment thereof, that specifically binds to a cognate antigen that is overly expressed, selectively expressed, or only expressed by senescent cell compared with a non-senescent, normal cell. The antibody may be an antibody that is internalized by the senescent cell via interaction with its cognate antigen. These specific antibodies may be polyclonal or monoclonal, prepared by immunization of animals and subsequent isolation of the antibody, or cloned from specific B cells according to methods and techniques routinely practiced in the art and described herein. A variable region or one or more complementarity determining regions (CDRs) may be identified and isolated from antigen-binding fragment or peptide libraries. An antibody, or antigen-binding fragment thereof, may be recombinantly engineered and/or recombinantly produced.

An antibody may belong to any immunoglobulin class, for example IgG, IgE, IgM, IgD, or IgA and may be obtained from or derived from an animal, for example, fowl (e.g., chicken) and mammals, which include but are not limited to a mouse, rat, hamster, rabbit, or other rodent, a cow, horse, sheep, goat, camel, human, or other primate. The antibody may be an internalising antibody. For use in human subjects, antibodies and antigen-binding fragments are typically human, humanized, or chimeric to reduce an immunogenic response by the subject to non-human peptides and polypeptide sequences.

Binding properties of an antibody to its cognate antigen may generally be determined and assessed using immunodetection methods including, for example, an enzyme-linked immunosorbant assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., Harlow et al., *Antibodies: A Laboratory Manual*, Cold Spring Harbor Laboratory (1988)). As used herein, an antibody is said to be "immunospecific," "specific for" or to "specifically bind" to a cognate antigen if it reacts at a detectable level with the antigen or immunogen. Affinities of antibodies and antigen binding fragments thereof can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.).

The antibody may be a monoclonal antibody that is a human antibody, humanized antibody, chimeric antibody, bispecific antibody, or an antigen-binding fragment (e.g., F(ab')$_2$, Fab, Fab', Fv, and Fd) prepared or derived therefrom. An antigen-binding fragment may also be any synthetic or genetically engineered protein that acts like an antibody in that it binds to a specific antigen to form a complex. For example, antibody fragments include isolated fragments consisting of the light chain variable region, Fv fragments consisting of the variable regions of the heavy and light chains, recombinant single chain polypeptide molecules (scFv proteins), and minimal recognition units consisting of the amino acid residues that mimic the hypervariable region. In certain other embodiments, antibodies are multimeric antibody fragments such as miniantibodies, bispecific and bifunctional antibodies comprising a first Fv specific for an antigen associated with a second Fv having a different antigen specificity, and diabodies and the like. Useful methodologies are described generally, for example in Hayden et al., *Curr Opin. Immunol.* 9:201-12 (1997) and Coloma et al., *Nat. Biotechnol.* 15:159-63 (1997); U.S. Pat. No. 5,910,573); (Holliger et al., *Cancer Immunol. Immunother.* 45:128-30 (1997); Drakeman et al., *Expert Opin. Investig. Drugs* 6:1169-78 (1997); Koelemij et al., *J. Immu-* nother. 22:514-24 (1999); Marvin et al., *Acta Pharmacol. Sin.* 26:649-58 (2005); Das et al., *Methods Mol. Med.* 109:329-46 (2005)).

A minimal recognition unit or other antigen binding fragment may be identified from a peptide library. Such peptides may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833). A peptide that is a minimal recognition unit or a CDR (i.e., any one or more of three CDRs present in a heavy chain variable region and/or one or more of three CDRs present in a light chain variable region) may be identified by computer modeling techniques, which can be used for comparing and predicting a peptide sequence that will specifically bind to a polypeptide of interest as described herein (see, e.g., Bradley et al., *Science* 309:1868 (2005); Schueler-Furman et al., *Science* 310:638 (2005)).

Antibodies may generally be prepared by any of a variety of techniques known to persons having ordinary skill in the art. Immunogens used to immunize animals and/or to screen for antibodies of desired specificity include proteins isolated from senescent cells that, for example, are present on the cell surface of a senescent cell in greater quantity or having a different conformation than on a non-senescent cell; and senescent cell extracts, including outer membrane preparations, organelles isolated from senescent cells, and the like. Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Schlebusch et al., *Hybridoma* 16:47-52 (1997) and references cited therein; Rader et al., *J. Biol. Chem.* 275: 13668-76 (2000); Popkov et al., *J. Mol. Biol.* 325:325-35 (2003); Andris-Widhopf et al., *J. Immunol. Methods* 242: 159-31 (2000)). Antibodies isolated from non-human species or non-human immunoglobulin libraries may be genetically engineered according to methods described herein and known in the art to "humanize" the antibody or fragment thereof.

Useful strategies for designing humanized antibodies may include, for example by way of illustration and not limitation, identification of human variable framework regions that are most homologous to the non-human framework regions of a chimeric antibody (see, e.g., Jones et al., *Nature* 321:522-25 (1986); Riechmann et al., *Nature* 332:323-27 (1988)). A humanized antibody may be designed to include CDR loop conformations and structural determinants of non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989)). Computer modeling may also be used to compare human structural templates selected by sequence homology with the non-human variable regions.

A therapeutic agent also includes a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)).

Therapeutic agents such as polypeptides, peptides, peptibodies, antibodies, and antigen binding fragments (i.e., peptides or polypeptides comprising at least one antibody V region) or other agents that specifically to a senescent cell can be linked to (i.e., conjugated to, fused to, or in some manner joined to or attached to) a second agent that selectively destroys or facilitates selective destruction of senescent cells. When delivered to the senescent cell by binding of the agent to the senescent cell, the cytotoxic moiety selectively destroys the senescent cell. If the agent is recombinantly produced, a nucleotide sequence encoding the cytotoxic moiety may be linked in frame to the agent and to one or more regulatory expression sequences to produce a fusion protein comprising the agent and cytotoxic moiety. Such second agents include cytotoxic molecules, including toxins derived from plants and microorganisms, as well as small molecules do not selectively bind to senescent cells in the absence of being linked to the aforementioned antibody, polypeptide, or peptide.

In certain embodiments, a therapeutic agent is a polynucleotide or oligonucleotide that specifically hybridize to a portion of the genome or mRNA of a cell that is a senescent cell or that is in a tumor microenvironment and may be induced to senescence by a cell damaging (i.e., biologically damaging) medical therapy. polynucleotides and oligonucleotides are provided that are complementary to at least a portion of a nucleotide sequence encoding a senescent cellular polypeptide of interest (e.g., a short interfering nucleic acid, an antisense polynucleotide, a ribozyme, or a peptide nucleic acid) and that may be used to alter gene and/or protein expression. As described herein, these polynucleotides that specifically bind to or hybridize to nucleic acid molecules that encode a cellular polypeptide may be prepared using the nucleotide sequences available in the art. In another embodiment, nucleic acid molecules such as aptamers that are not sequence-specific may also be used to alter gene and/or protein expression.

Antisense polynucleotides bind in a sequence-specific manner to nucleic acids such as mRNA or DNA. Identification of oligonucleotides and ribozymes for use as antisense agents and identification of DNA encoding the genes for targeted delivery involve methods well known in the art. For example, the desirable properties, lengths, and other characteristics of such oligonucleotides are well known. Antisense technology can be used to control gene expression through interference with binding of polymerases, transcription factors, or other regulatory molecules (see Gee et al., In Huber and Carr, *Molecular and Immunologic Approaches,* Futura Publishing Co. (Mt. Kisco, N.Y.; 1994)).

Short interfering RNAs may be used for modulating (decreasing or inhibiting) the expression of a gene encoding a senescent cell-associated polypeptide. For example, small nucleic acid molecules, such as short interfering RNA (siRNA), micro-RNA (miRNA), and short hairpin RNA (shRNA) molecules may be used according to the methods described herein to modulate the expression of a cellular polypeptide of interest. A siRNA polynucleotide preferably comprises a double-stranded RNA (dsRNA) but may comprise a single-stranded RNA (see, e.g., Martinez et al. *Cell* 110:563-74 (2002)). A siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein and known and used by persons skilled in the art.

In certain other embodiments, methods are provided herein for identifying a therapeutic agent that suppresses cellular senescence by using the animal models described herein. Candidate therapeutic agents may be administered to an animal of the animal model to provide a treated animal, followed by determining suppression of cellular senescence as described herein (i.e., determining the level or extent to which the candidate agent kills or facilitates killing of a senescent cell or determining the level of one or more senescence cell-associated molecules including senescence cell-associated polypeptides expressed or secreted by a senescent cell). The capability of the agent to suppress cellular senescence is determined by comparing the level or extent to which the candidate agent kills or facilitates killing of a senescent cell and/or comparing the level of one or more senescence cell-associated proteins expressed or secreted by a senescent cell in the treated animal with an untreated (i.e., vehicle only or placebo) control animal. A statistically or biologically significant decrease or reduction of cellular senescence in the treated animal compared with untreated, control animal thereby identifies an agent that suppresses cellular senescence. As described herein, positive control animal groups (i.e., those that include an agent capable of destroying or facilitating destruction of a senescent cell or that inhibit or reduce expression or secretion of one or more senescence cell-associated polypeptides) may also be included in such methods.

Also provided herein are methods for identifying a therapeutic agent for treating and/or preventing a cancer that employ primary cells from an animal model mouse or a cell line prepared from cells isolated from the animal model mouse. In one embodiment, primary cells or a cell line derived from the animal model mouse may be used in screening (including high throughput methods) for therapeutic agents that suppress cellular senescence. The cells may be exposed to, contacted, mixed with, or in some manner permitted to interact with an agent (e.g., a medical therapy) that induces cellular senescence prior to, concurrent with, or subsequent to contact with a candidate therapeutic agent. Suppression of cellular senescence may be determined by any of the methods described herein or in the art.

High throughput screening, typically automated screening, of a large number of candidate therapeutic agents from synthetic or natural product libraries may be used to identify therapeutic agents. The candidate therapeutic agents to be screened may be organized in a high throughput screening format such as using microfluidics-based devices, or a 96-well plate format, or other regular two dimensional array, such as a 384-well, 48-well or 24-well plate format, or an array of test tubes. The format is therefore amenable to automation. An automated apparatus that is under the control of a computer or other programmable controller may be used for one or more steps of the methods described herein. A controller may monitor the results of each step of the method and may automatically alter the testing paradigm in response to those results.

Pharmaceutical Compositions and Methods of Treatment

The present disclosure further provides for pharmaceutical compositions comprising any of the agents that are useful for treating or preventing cancer and that suppress cellular senescence, which agents are identified according to the methods described herein and a pharmaceutically acceptable excipient. The therapeutic agents described herein may be formulated in a pharmaceutical composition for use in treatment or preventive (or prophylactic) treatment (e.g., reducing the likelihood of occurrence, of exacerbation of disease, or occurrence or recurrence of one or more symptoms of the disease). The methods and excipients described herein are exemplary and are in no way limiting. Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed 2006, and in *Remington: The Science and Practice of Pharmacy* (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

The pharmaceutical compositions may be in the form of a solution. Alternatively, they may be in the form of a solid, such as powder, tablets, or the like.

The present disclosure also provides a method for treating or preventing cancer in a subject who has or who is at risk of developing cancer comprising administering a therapeutic agent that selectively suppresses cellular senescence in the subject, thereby treating or preventing cancer in the subject.

As understood by a person skilled in the medical art, the terms, "treat" and "treatment," refer to medical management of a disease, disorder, or condition of a subject (i.e., patient) (see, e.g., Stedman's Medical Dictionary). "Preventing cancer" refers to reducing the likelihood of occurrence of a cancer or reoccurrence of the cancer.

A therapeutic agent for "treating" cancer provides an improvement or increase of the therapeutic and/or prophylactic benefit compared with the benefit observed in the absence of administering the agent. For example, therapeutic benefit includes any one or more of reducing the size of the tumor(s), inhibiting tumor progression, inhibiting tumor growth, delaying tumor colonization, and/or inhibiting, preventing, or delaying metastasis of a tumor. Therapeutic and/or prophylactic benefit for subjects to whom the agents are administered, includes, for example, an improved clinical outcome, wherein the object is to prevent or slow or retard (lessen) an undesired physiological change associated with the cancer, or to prevent or slow or retard (lessen) the expansion or severity of such disease. As discussed herein, enhancing the effectiveness of a medical therapy may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

Subjects who have cancer include a subject who is in remission (also called cancer remission herein), whether partial or complete. Remission refers to a decrease in or disappearance of signs and symptoms of cancer. In partial remission, some but not all, signs and symptoms of cancer have disappeared. In complete remission, all signs and symptoms of cancer have disappeared and if cancer cells remain, they are not detectable. Subjects who are in remission, either partial or complete, and who have a risk of cancer recurrence may be treated with a therapeutic agent described herein.

Patients who are at risk of developing a cancer include those who have one or more genetic mutations that increase the likelihood that the subject will develop the cancer. By way of example, human genes BRCA1 and BRCA2 belong to a class of genes known as tumor suppressors. Mutation(s) of these genes has been linked to hereditary breast and ovarian cancer. BRCA1 mutations may also increase a woman's risk of developing colon, uterine, cervical, and pancreatic cancer. Certain mutations in BRCA2 also increase the risk of pancreatic cancer as well as stomach cancer, gallbladder and bile duct cancer, and melanoma. Men with certain BRCA1 mutations and/or BRCA2 mutations also have an increased risk of breast cancer and, and possibly, of pancreatic cancer, testicular cancer, and early-onset prostate cancer. Subjects at risk of developing a cancer also include those who have xeroderma pigmentosum that results from mutations in XPD helicase, which is required for nucleotide excision repair.

The effectiveness of a therapeutic agent can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of the treatment of a therapeutic agent or pharmaceutical composition can be analyzed using techniques known in the art, such as comparing symptoms of patients suffering from a particular type of cancer that have received the treatment with those of patients with the same or similar type of cancer without such a treatment or with placebo treatment.

In certain embodiments of the method for treating or preventing cancer, the therapeutic agents are identified according to the screening methods provided herein. In certain other embodiments, the therapeutic agents may be other agents known in the art that selectively suppresses cellular senescence and that treat and/or prevent cancer. The therapeutic agents or pharmaceutical compositions that selectively suppress cellular senescence and that are useful for treating or preventing cancer provided herein may be administered orally, topically, transdermally, parenterally, by inhalation spray, vaginally, rectally, or by intracranial injection, or any combination thereof. In one embodiment, the therapeutic agents or compositions comprising the agents are administered parenterally, such as via subcutaneous, intravenous, intramuscular, or intracisternal injection, or via infusion techniques.

The therapeutic agents or pharmaceutical compositions that selectively suppress cellular senescence provided herein are administered to a subject who has or is at risk of developing cancer at a therapeutically effective dose. A "therapeutically effective dose" of a specific therapeutic agent refers to that amount of the agent sufficient to result in reducing the severity of, eliminating, or delaying the onset or reoccurrence of one or more symptoms of a cancer in a statistically significant manner. Such a dose may be determined or adjusted depending on various factors including the specific therapeutic agents or pharmaceutical compositions, the routes of administration, the subject's condition, that is, stage of the disease, severity of symptoms caused by the disease, general health status, as well as age, gender, and weight, and other factors apparent to a person skilled in the medical art. Similarly, the dose of the therapeutic for treating a disease or disorder may be determined according to parameters understood by a person skilled in the medical art. Optimal doses may generally be determined using experimental models and/or clinical trials. Design and execution of pre-clinical and clinical studies for a therapeutic agent (including when administered for prophylactic benefit) described herein are well within the skill of a person skilled in the relevant art. The optimal dose of a therapeutic may depend upon the body mass, weight, or blood volume of the subject. For example, an amount between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight (which can be administered as a single dose, daily, weekly, monthly, or at any appropriate interval) of a therapeutic agent may be administered.

This disclosure contemplates a dosage unit comprising a pharmaceutical composition provided herein. Such dosage units include, for example, a single-dose or a multi-dose vial or syringe, including a two-compartment vial or syringe, one comprising the pharmaceutical composition of this disclosure in lyophilized form and the other a diluent for reconstitution. A multi-dose dosage unit can also be, e.g., a bag or tube for connection to an intravenous infusion device.

Accordingly, provided herein are methods for treating or preventing (i.e., reducing the likelihood of occurrence or recurrence) cancer in a subject who has cancer or who is at risk of developing cancer, said method comprising administering a therapeutic agent that selectively suppresses cellular senescence in the subject, thereby treating or preventing cancer in the subject. In certain embodiments, suppressing cellular senescence comprises suppressing the expression or secretion of one or more senescence cell-associated molecules of senescent cells. In other certain embodiments, suppressing cellular senescence comprises reducing the quantity of senescent cells.

EXAMPLES

Example 1

Preparation of p16-3MR Transgenic Mice

To examine the role of senescent cells in cancer, in the risk of developing cancer or in side effects arising after cancer treatment, a transgenic mouse comprising a $p16^{Ink4a}$ promoter operatively linked to a trimodal fusion protein was generated to allow for detection of senescent cells and for selective clearance of senescent cells in those transgenic mice.

The promoter, $p16^{Ink4a}$, which is transcriptionally active in senescent cells but not in non-senescent cells (see, e.g., Wang et al., *J. Biol. Chem.* 276:48655-61 (2001); Baker et al., *Nature*, supra) was engineered into a nucleic acid construct. The $p16^{Ink4a}$ gene promoter (approximately 100 kilobase pairs) was introduced upstream of a nucleotide sequence encoding a trimodal reporter fusion protein. Alternatively, a truncated $p16^{Ink4a}$ promoter may be used (see FIGS. 5 and 6 providing an exemplary vector and exemplary promoter sequence) (see, e.g., Baker et al., *Nature*, supra; International Application Publication No. WO/2012/177927; Wang et al., *J. Biol. Chem.* 276:48655-61 (2001)). The trimodal reporter protein is termed 3MR and consists of *renilla* luciferase (rLUC), monomeric red fluorescent protein (mRFP) and a truncated herpes simplex virus thymidine kinase (tTK) (see, e.g., Ray et al., *Cancer Res.* 64:1323-30 (2004)). Thus, the expression of 3MR is driven by the $p16^{Ink4a}$ promoter in senescent cells only. The polypeptide sequences and the encoding polynucleotides for each of the three proteins are known in the art and are available in public databases, such as GenBank. An exemplary sequence (SEQ ID NO:25) for the 3MR transgene is provided in FIG. 7. The 3MR transgene was inserted into a BAC vector using techniques routinely practiced by person skilled in the molecular biology art. The detectable markers, rLUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57Bl6 background, were established and bred using known procedures for introducing transgenes into animals (see, e.g., Baker et al., Nature, supra). The transgenic mice are called p16-3MR herein.

Example 2

Senescent Cells can be Detected and Cleared in Transgenic p16-3MR Mice

Senescent cells can be detected using a variety of biomarkers, including the strongly upregulated p16-INK4a tumor suppressor protein (Campisi et al., *Nature Rev. Molec. Cell Biol.* 8:729-40 (2007)). Using such markers, it was shown that both normal and tumor cells undergo senescence, in mice and humans, after exposure to ionizing radiation or DNA-damaging chemotherapy (Coppe et al., *PLoS Biol.* 6:2853-68 (2008); Schmitt et al., *Cell* 109:335-46 (2002); to Poele et al., *Canc. Res.* 62:1876-83 (2002); Le et al., *Aging Cell* 9:398-409 (2010)). For example, p16-3MR transgenic mice will accumulate senescent cells when exposed to genotoxins (e.g., ionizing radiation, DNA damaging chemicals), epigenomic toxins (e.g., compounds that perturb histone modifications or DNA methylation), strong mitogenic signals (e.g., activated oncogenes, elevated levels of growth factors, certain hormones). But, as noted herein, one advantage of the p16-3MR transgenic mice is that they express tTK, which allows for selective killing of senescent cells by administering pro-drug ganciclovir (GCV) to the mice since GCV is converted into a cytotoxin by tTK. Therefore, the clearance of senescent cells in p16-3MR transgenic mice exposed to radiation was examined after GCV treatment.

Briefly, a group of p16-3MR transgenic mice were exposed to whole body ionizing radiation (7 Gy X-ray) and a control group of p16-3MR transgenic mice were mock-irradiated. After three months, the mice were treated with GCV (25 mg/kg) or vehicle only, and then at least two weeks later bioluminescence in tissues was examined after administering the rLUC substrate.

In several tissues, irradiated mice (IR) showed a greater than 2-fold higher bioluminescence than unirradiated mice (Ctrl), indicating that rLUC is expressed three months after radiation exposure and, therefore, the presence of senescent cells is persisting (see FIG. 1A, showing bioluminescence results in lung tissue). Moreover, mice treated with GCV exhibited rLUC expression levels comparable to unirradiated mice, indicating that GCV resulted in elimination of senescent cells (FIG. 1A).

As is known in the literature, senescent cells also secret molecules that can cause inflammation (Freund et al., *Trends Mol. Med.* 16:238-46 (2010)), which, if chronic, will fuel various pathologies, including cancer (Davalos et al., *Cancer Metastasis Rev.* 29:273-83 (2010))—this is often referred to as senescence-associated secretory phenotype (SASP). For example, IL-6 (interleukin-6) and MMP-3 (matrix metalloproteinase-3) are two prominent SASP components. Hence, RNA expression levels of various biomarkers associated with SASP were examined, including p16INK4a (p16), IL-6 and MMP-3. In addition, the level of the mRFP reporter was measured. FIG. 1B shows that GCV returned p16INK4a (p16), IL-6, MMP-3 and mRFP expression levels to those found in the unirradiated control mice. Furthermore, GCV notably had no detectable effect on expression levels when given to wild-type, non-transgenic C57B16 mice (data not shown).

Example 3

Cellular Senescence Increases the Likelihood of Cancer and Metastasis

To examine the role of senescence in contributing to, inducing or increasing the likelihood of tumor formation or growth and metastasis, tumor engraftment was monitored in p16-3MR transgenic mice that were either depleted of senescent cells and in mice that had senescent cells (naturally developed or induced).

Briefly, $10^6$ B16 mouse melanoma cells, a highly aggressive cell line that is syngeneic with p16-3MR transgenic mice (C57B16 background), that express firefly luciferase (fLUC, to enable their detection by bioluminescence) were injected into the tail vein of the p16-3MR transgenic mice three months after being either mock irradiated or irradiated, as described in Example 2. B16 mouse melanoma cells first colonize the lung, where they form primary tumors approximately two weeks after injection, and thereafter metastasize to distal tissues to form secondary tumors in, for example, the pancreas, liver and visceral fat. The biolumninescence markers, fLUC and rLUC are distinguishable because the enzymes use different substrates.

Figure 8:
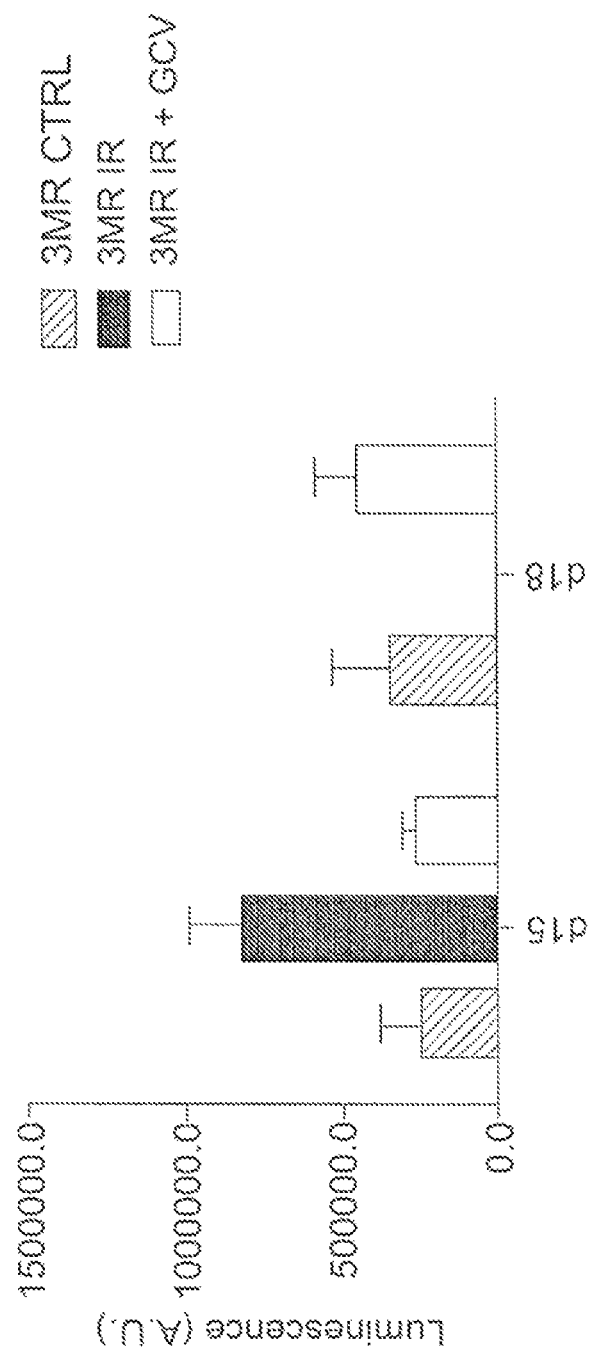
FIG. 8 shows full body rLUC luminescence measurements of the B16 melanoma cells from the mice in FIGS. 2A-2C. Irradiated mice were moribund at day 15-16 and were sacrificed.

As shown in FIG. 2, tumor progression occurred much faster in the irradiated mice as compared to the mock-irradiated mice. Fifteen days after the injection, mock-irradiated (Ctrl) mice had some relatively small lung nodules (see FIG. 2A). In contrast, irradiated mice had significantly more primary tumors and, additionally, the animals harbored a large number of metastatic tumors (see FIG. 2B)—these animals were moribund between days 15 and 16 after injection. Strikingly, irradiated mice in which senescent cells were cleared after GCV treatment showed much smaller primary tumors and many fewer metastases (see FIG. 2C). B16 mouse melanoma cells were detected in the mice—15-18 days post-injection by measuring fLUC biolumenscence. Irradiated mice were moribund at days 15-16 post-injection and sacrificed. Fifteen days after the injection, mock-irradiated (Ctrl) mice and irradiated mice in which senescent cells were cleared after GCV treatment both had relatively low levels of B16 cells as detected by luminescence (see FIG. 8). Irradiated mice had significantly larger numbers of B16 cells as detected by luminescence (see FIG. 8). On day 18, irradiated mice in which senescent cells were cleared after GCV treatment still showed relatively low levels of B16 cells as did the mock-irradiated control (Ctrl) mice (see FIG. 8).

Figure 3:
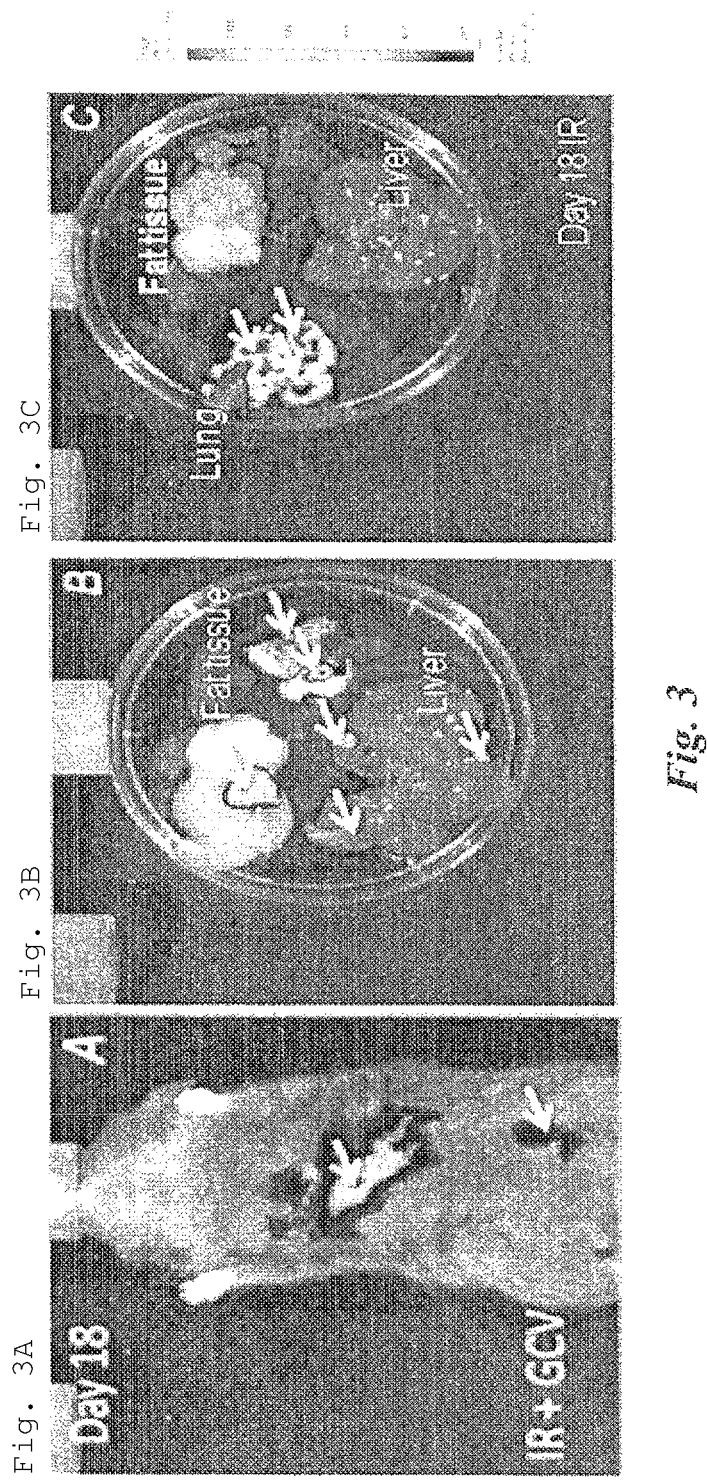
FIGS. 3A-3C show that elimination of senescent cells suppresses the development of metastases. The p16-3MR transgenic mice of FIG. 2 were followed for an additional three days (i.e., day 18). The irradiated mice treated with GCV (in which senescent cells were eliminated) eventually developed primary tumors in the lungs (FIG. 3A). But, despite the presence of primary tumors in the lung, the fat and liver tissues remained relatively metastasis free (FIG. 3C). In contrast, irradiated mice not treated with GCV (which retain senescent cells) showed metastatic tumors in the liver and fat tissue (FIG. 3B).

Eighteen days after injecting the B16 melanoma cells, large primary lung tumors were evident in the irradiated mice that received GCV treatment (see FIG. 3A). But, despite the presence of tumors in the lungs, the distal organs remained almost devoid of metastases (see FIG. 3A; see also FIG. 3C showing liver and fat tissue). This was in sharp contrast to irradiated mice not treated with GCV, in which the liver and fat harbored multiple metastatic tumors (see FIG. 3B), which were already present by day 15.

Luminescent metastatic nodules were also counted in control, irradiated, and irradiated+GCV treated mice as provided in Table 1 below. As nodules are difficult to count in fat tissue, metastatic cells were represented as an estimated % of total area of fat.

TABLE

Detection of metastatic B16 melanoma cells 18 days after injection

|  | Control mice | Irradiated mice | Irradiated + GCV |
|---|---|---|---|
| Lung | Too numerous to count (TNTC) | TNTC | TNTC |
| Liver | 6.25 ± 1.7 nodules | 14.5 ± 2.8 nodules | 7 ± 3.6 nodules |
| Fat | 50% | 100% | 25% |

Figure 9A:
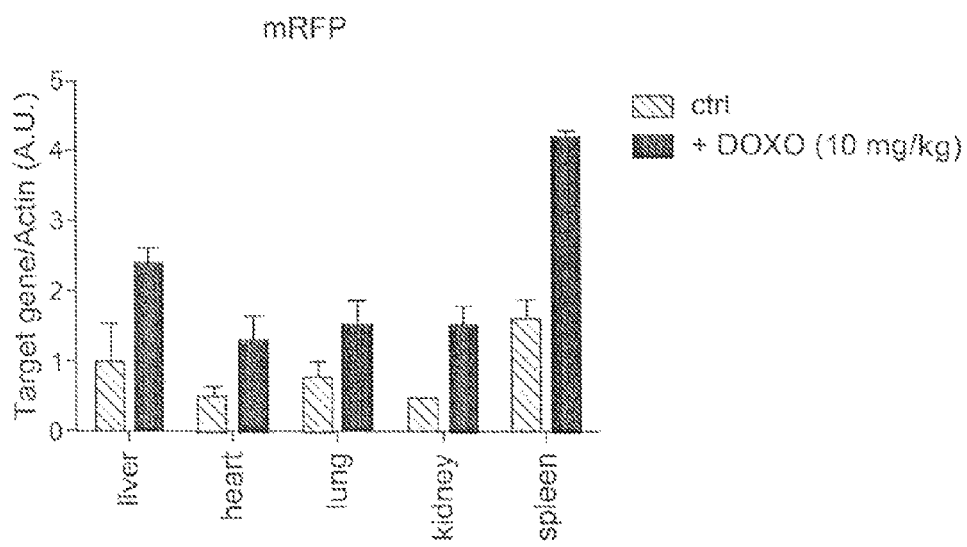
FIGS. 9A-9B show that treatment with doxorubicin induces persistent senescent cells in p16-3MR transgenic mice. The transgenic p16-3MR mice were mock treated with vehicle (Ctrl) or treated with 10 mg/kg of doxorubicin (DOXO). Various tissues were isolated (liver, heart, lung, kidney, and spleen) and measured for abundance of mRNAs encoding mRFP (FIG. 9A) and p16INK4a (FIG. 9B) (normalized to actin).
Figure 9B:
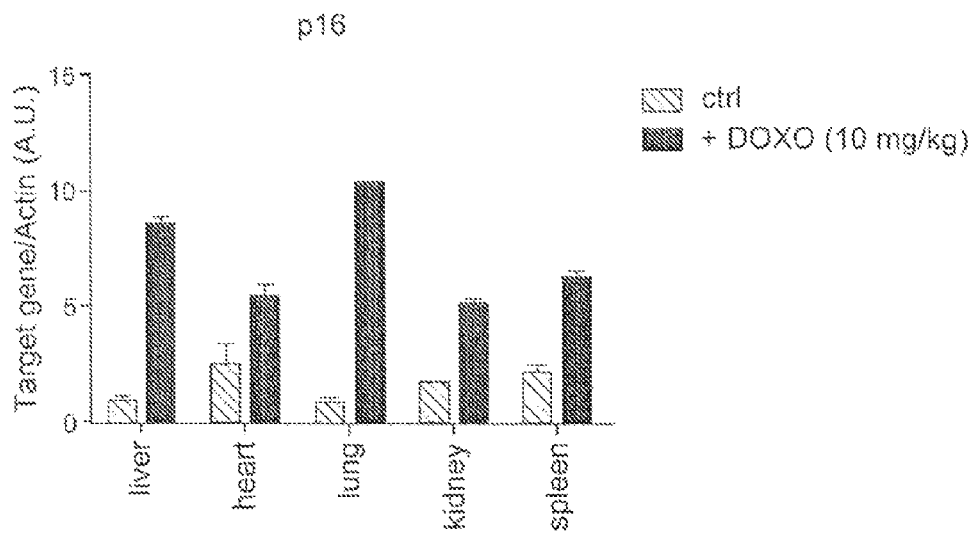

Similar results were observed when the senescent cell accumulation was induced with the chemotherapeutic agent, doxorubicin. Using p16-3MR mice, treatment doxorubicin (10 mg/kg) induced the persistent presence of senescent cells in tissues, similar to the effects of radiation. Various tissues were isolated (liver, heart, lung, kidney, and spleen) and measured for abundance of mRNAs encoding mRFP and p16INK4a as markers for senescent cells (see FIGS. 9A and 9B, respectively). Doxorubicin-treated mice consistently expressed higher levels of mRFP and p16INK4a in all tissues compared to untreated control mice.

Also similar to the effects of radiation, doxorubicin treatment stimulated the growth of B16 melanoma cells that were injected subcutaneously. Again, similar to radiation GCV (which eliminates senescent cells in p16-3MR mice) substantially reduced the size of B16 melanoma tumors in mice pre-treated with doxorubicin. Briefly, p16-3MR transgenic mice were treated with vehicle (ctrl) or 10 mg/kg doxorubicin. Seven days after doxorubicin treatment, mice were treated daily with GCV (25 mg/kg) for 7 days or vehicle only. 3 days after the last GCV treatment, $4 \times 10^5$ B16 mouse melanoma cells were injected subcutaneously into the p16-3MR transgenic mice, and mice were sacrificed after 12 days for analysis.

Figure 10:
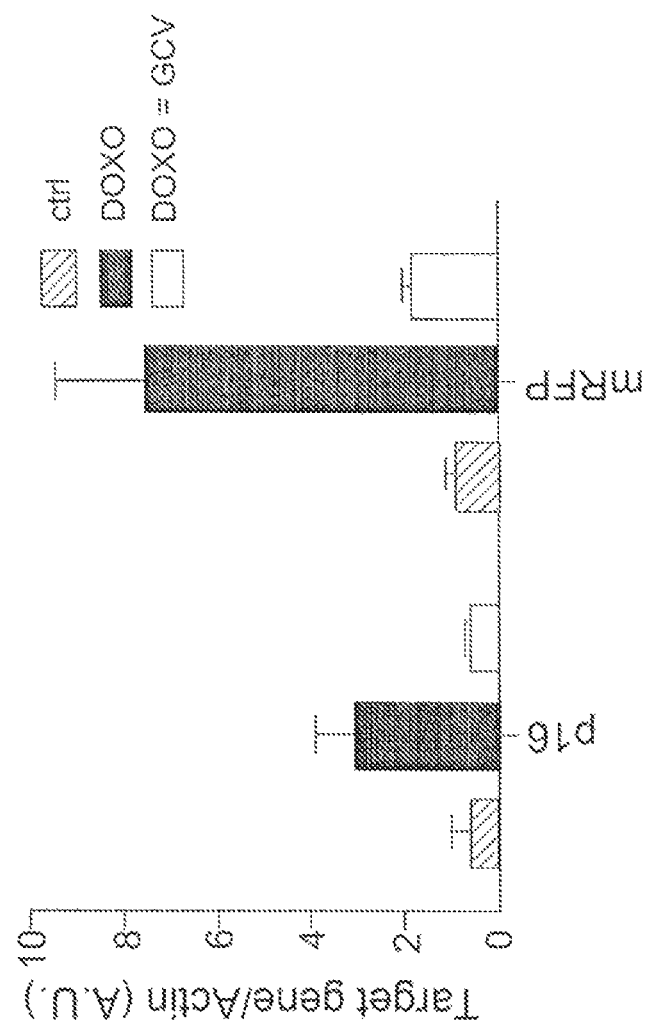
FIG. 10 shows that doxorubicin induces persistent senescent cells in p16-3MR transgenic mice and that GCV treatment leads to depletion of senescent cells and reducing the level of SASP biomarkers, p16INK4 and mRFP. Skin biopsies were isolated and measured for abundance of p16INK4 and mRFP (normalized to actin). Results are shown in arbitrary units (AU) after setting Ctrl levels at 1.

Skin biopsies were collected and measured for abundance of senescent cell biomarkers (p16INK4a and mRFP mRNAs). As shown in FIG. 10, skin biopsies from doxorubicin treated mice showed increased senescence as compared to skin biopsies from untreated control mice, as measured by p16INK4a and mRFP expression. In contrast, doxorubicin-treated mice in which senescent cells were cleared by GCV treatment showed low levels of p16INK4a and mRFP expression.

Figure 11:
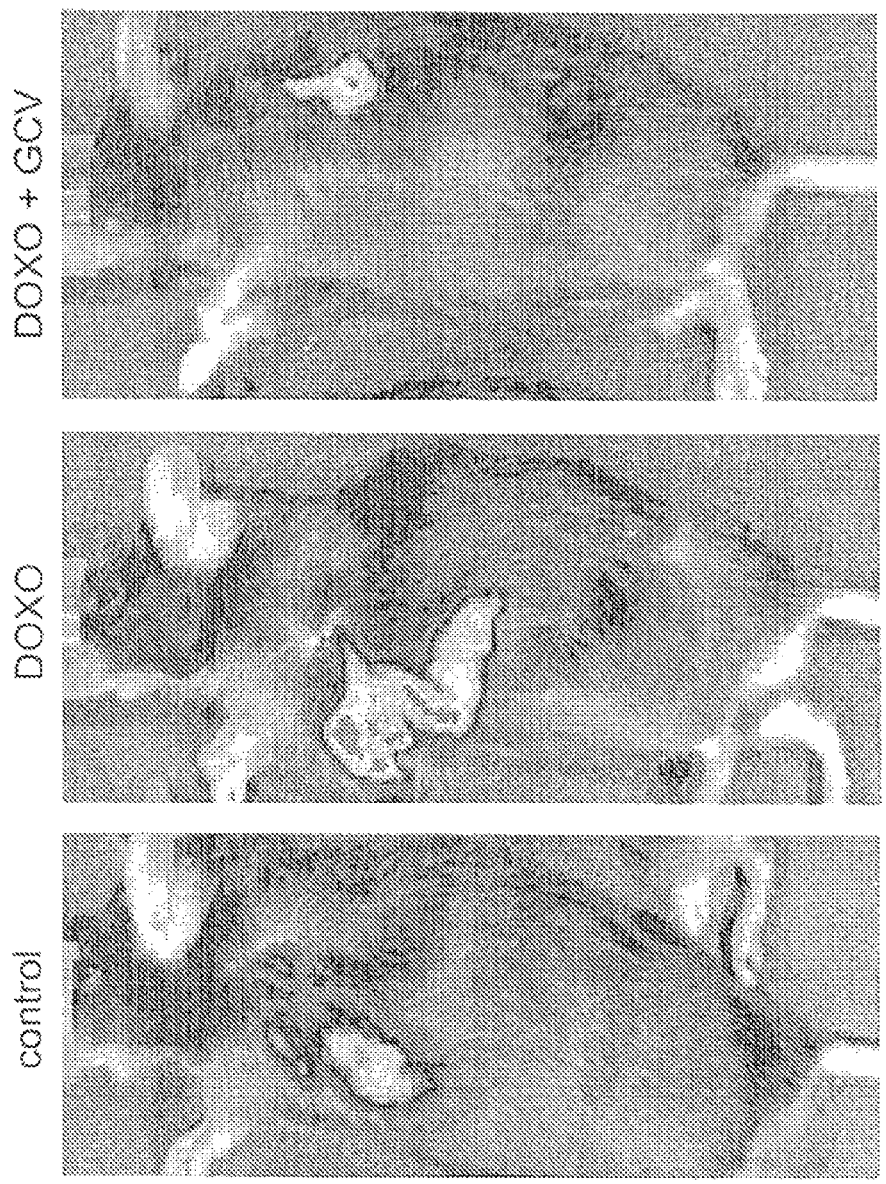
FIG. 11 shows senescent cells induced in p16-3MR transgenic mice by doxorubicin treatment promoted primary tumor growth. The transgenic p16-3MR mice were vehicle-treated (Ctrl) or treated with doxorubicin (10 mg/kg). 7 days later, the doxorubicin treated mice were mock treated with vehicle (DOXO) or GCV (DOXO+GCV), then injected subcutaneously with fLUC-expressing B16 melanoma cells. Twelve days later, bioluminescence of the B16 melanoma cells was measured.
Figure 12:
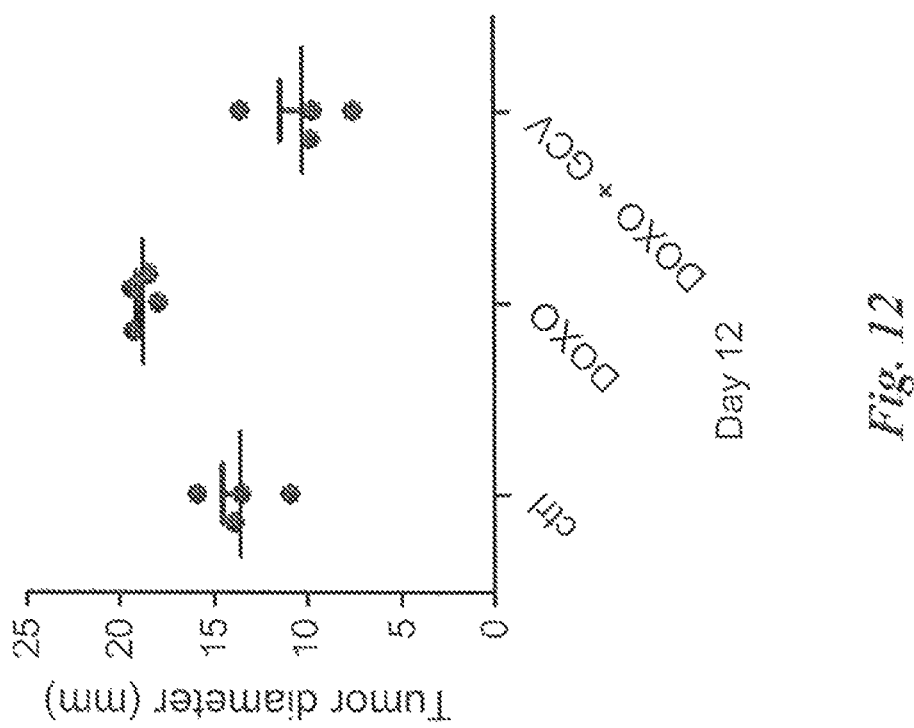
FIG. 12 shows that clearance of senescent cells in doxorubicin treated p16-3MR transgenic mice reduced tumor size. The transgenic p16-3MR mice were vehicle-treated (Ctrl) or treated with doxorubicin (10 mg/kg). 7 days later, the doxorubicin treated mice were mock treated with vehicle (DOXO) or GCV (DOXO+GCV), then injected subcutaneously with fLUC-expressing B16 melanoma cells. Twelve days later, primary tumor diameter was measured.

Tumor growth was increased in doxorubicin-treated mice as compared to vehicle-treated control mice (see FIG. 11). In contrast, doxorubicin-treated mice in which senescent cells were cleared after GCV treatment showed much smaller primary tumors (see FIG. 11). Tumor diameters were also measured and also confirmed that doxorubicin-treated mice in which senescent cells were eliminated by GCV treatment had smaller tumor sizes, and doxorubicin-treated mice had increased tumor sizes (see FIG. 12).

Overall, an increase in senescent cell population induced by radiation correlated with a greatly increased primary tumor size and with metastases, but this was largely abrogated when senescent cells were depleted in mice treated with GCV. In other words, these results show that the persistent presence of senescent cells after exposure to a senescence causing stress can promote the growth of primary tumors and will advance the development of metastases. Thus, senescence cell clearance or depletion can delay, prevent, or reduce the risk or likelihood of tumor formation or metastasis.

Example 4

Senescent Cell Clearance Reduces Likelihood of K-Ras Mediated Tumorigenesis

To examine the role of senescence in contributing to, inducing or increasing the likelihood of K-Ras mediated lung tumor formation or growth and metastasis, tumor formation was monitored in INK-ATTAC transgenic mice that were either depleted of senescent cells or have senescent cells (naturally developed or induced).

Briefly, INK-ATTAC ($p16^{Ink4a}$ apoptosis through targeted activation of caspase) transgenic mice have an FK506-binding protein (FKBP)-caspase 8 (Casp8) fusion polypeptide under the control of the $p16^{Ink4a}$ promoter (see FIG. 5 providing a vector sequence for the transgene and FIG. 6 providing sequences for components of the transgene including the promoter sequence). In the presence of AP20187, a synthetic drug that induces dimerization of a membrane bound myristoylated FKBP-Casp8 fusion protein, senescent cells specifically expressing the FKBP-Casp8 fusion protein via the $p16^{Ink4a}$ promoter undergo programmed cell death (apoptosis) (see, e.g., Baker, Nature, supra, FIG. 1 therein). Two founder lines (INK-ATTAC[3] and INK-ATTAC[5]) were each bred with the K-rasLA1 tumor model. K-rasLA1 mice were first developed by Tyler Jacks at MIT (see Johnson, L. et al., Nature 410:1111-16 (2001). The mice activate a silent K-ras oncogene through a spontaneous recombination event. The mean age of death/sacrifice of K-rasLA1 mice is about 300 days as a result of extensive tumor burden. The most frequent organ site is the lung and varying grades of tumors are present as early as six weeks of age from hyperplasia/dysplasia to carcinomas similar to human non-small cell lung cancer. Metastasis to thoracic lymph nodes, kidney and other visceral organs occurs with low frequency. Other organ sites include the thymus (thymic lymphoma) and skin (papillomas). A companion strain (K-ras$^{LA2}$) carries an allele that recombines to the activated allele (K-Ras$^{G12D}$) 100% of the time.

Figure 4:
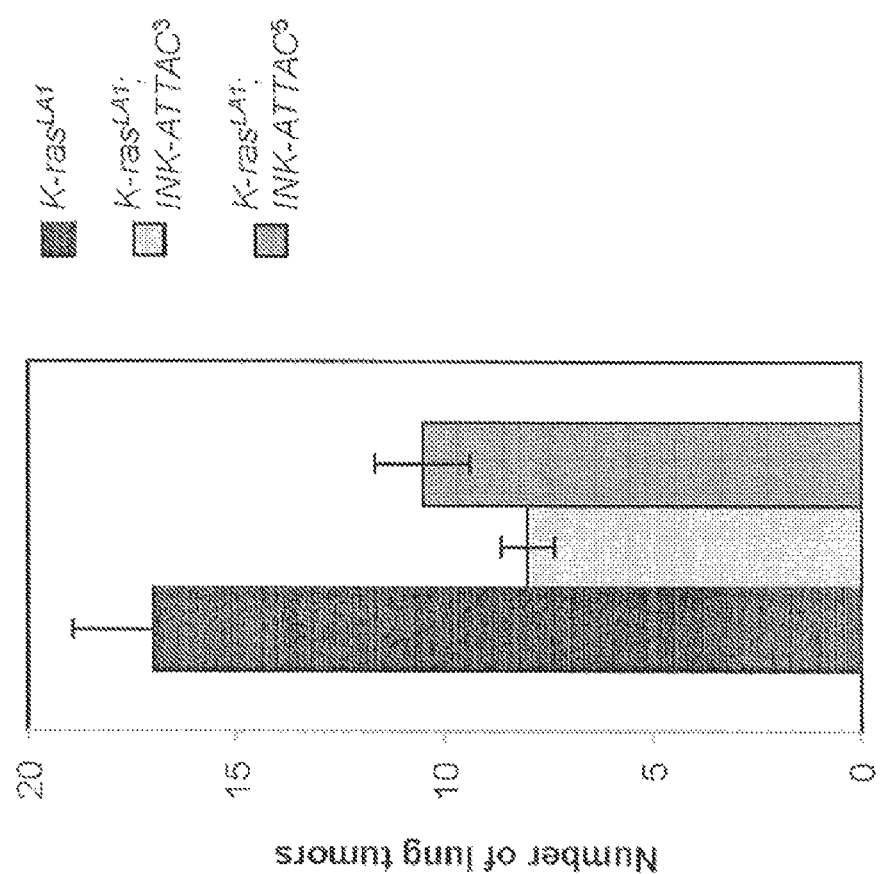
FIG. 4 shows that elimination of senescent cells suppresses the multiplicity of K-Ras induced lung tumors as compared to mice in which senescent cells were not cleared or reduced.

Two INK-ATTAC:K-RasLA1 were produced (one for INK-ATTAC line 3 and one for line 5). Beginning at three weeks of age, one half each cohort was treated with 2 mg AP20187/g body weight and the remaining half with vehicle (PBS). Twenty one days after treatment, the mice were sacrificed and tumor multiplicity in lungs was measured. Tumor numbers were found to be significantly reduced in INK-ATTAC3:K-RasLA1 and INK-ATTAC5:K-RasLA1 transgenic mice that had senescent cells depleted after treatment with AP20187 (see FIG. 4). In addition, metastasis and overall survival will be monitored after tumor induction in the presence or absence of p16-positive cells.

Example 5

Senescent Cell Clearance Reduces Likelihood of Breast Cancer or Skin Carcinogenesis Similar experiments to those of Example 4 are performed using doxycycline-mediated expression of HER2 (see, e.g., Yeh et al., J. Clin. Investig. 121:866-79 (2011); see also Gunther et al., FASEB 16:283-92 (2002)) to examine the role of senescence in contributing to, inducing or increasing the likelihood of breast cancer. For example, founder INK-ATTAC lines are each bred onto a transgenic mouse MMTV-HER2 or a bi-transgenic mouse MMTV-rtT:TetO-HER2 genetic background, wherein doxycycline is used to induce breast tumor formation subsequent to a senescence inducing factor (e.g., radiation or chemotherapy) used to induce senescent cell accumulation.

Alternatively, INK-ATTAC transgenic mice are treated with a senescence inducing factor (e.g., radiation or chemotherapy) and then a carcinogen to examine the role of senescence in contributing to, inducing or increasing the likelihood of skin carcinogenesis (see, e.g., Slaga et al., *J. Investig. Dermatol. Symp. Proc.* 1:151-6 (1996)).

Example 6

Senescent Cell Reduction Reduces Likelihood of Side Effects from Senescence Inducing Chemotherapy To examine the role of senescence in contributing to, inducing or increasing the likelihood of side effects resulting from, for example, radiation or chemotherapy used to treat cancer that has already developed. Such side effects may include returning or recurring tumor formation or growth and metastasis. Side effects are monitored in p16-3MR transgenic mice that are either depleted of senescent cells or have senescent cells (naturally developed or induced).

Briefly, tumor cell lines are engineered to express firefly luciferase (fLUC) to enable their detection of tumors and metastases by bioluminescence in a living animal. For example, a B16-fLUC mouse melanoma cell line (PerkinElmer, Waltham, Mass.) and an MMTV-PymT:fLUC mammary carcinoma cell line can be used in the experiments described in this example. To prepare the MMTV-PyMT-fLUC cell line, MMTV cells were infected with a lentivirus that contained a sequence that encodes Firefly Luciferase and contained the mammalian puromycin resistance gene. Cells were then selected through puromycin treatment and tested for luminescence.

Figure 14:
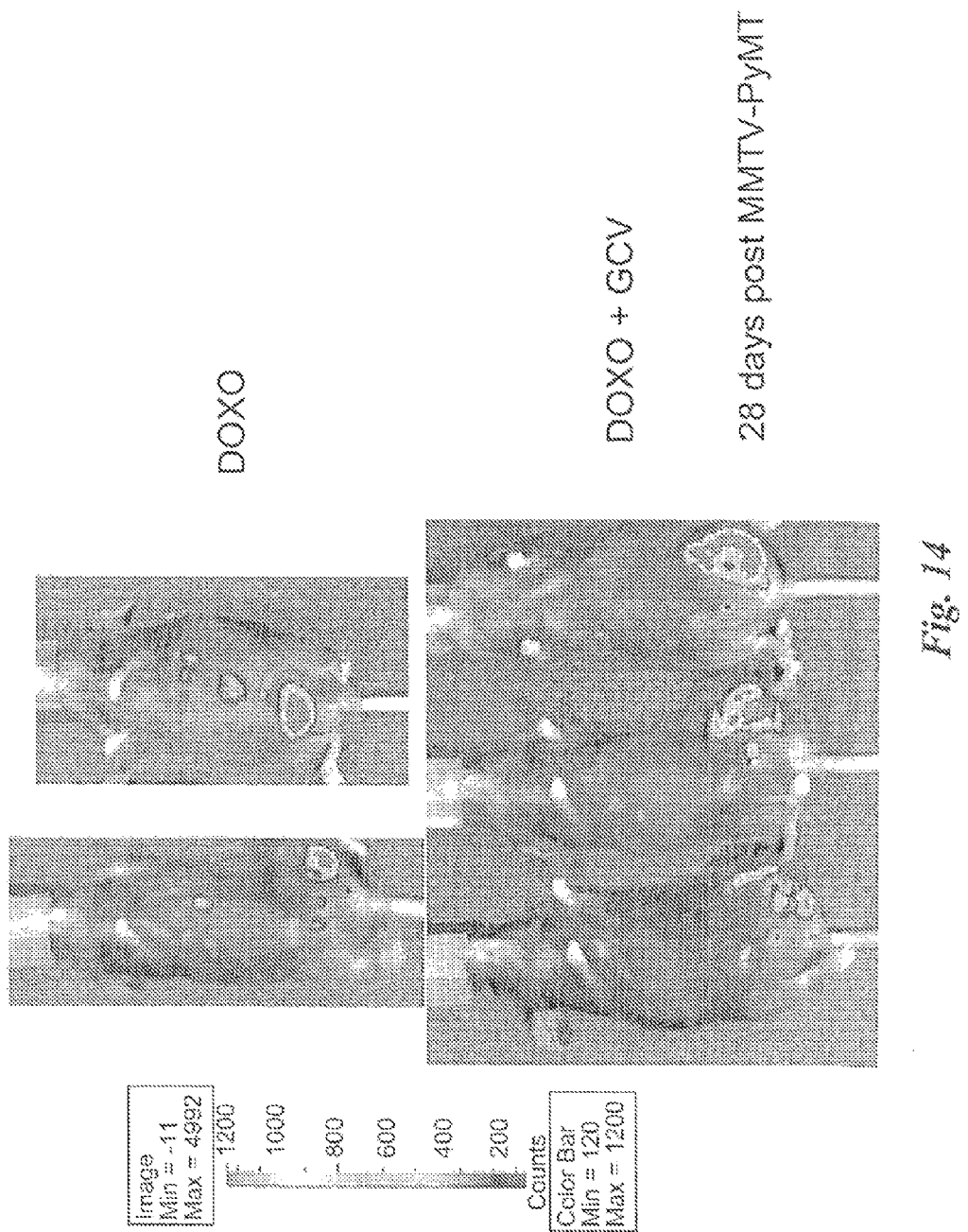
FIG. 14 illustrates the quantity of tumor cells and the location of the tumor cells in p16-3MR transgenic mice 28 days after injection with MMTV-PyMT cells, followed by treatment with doxorubicin (DOXO) or doxorubicin and ganciclovir (DOXO+GCV).

The MMTV-PymT tumor cells ($5 \times 10^5$ cells) were injected into a mammary fat pad of each mouse. Small primary tumors formed over a period of one week. Then doxorubicin (DOXO) at 10 mg/kg or vehicle only (PBS) was administered once at Day 7. Beginning three days after mice received DOXO, GCV was then administered daily for five days intraperitoneally at 25 mg/kg, or vehicle only was administered. Four different treatment groups of mice (7 mice per group) included (1) no doxorubicin (vehicle), no GCV (vehicle); (2) doxorubicin, no GCV; (3) no doxorubicin, GCV; and (4) doxorubicin, GCV. Mouse survival was monitored, and the results are presented in FIG. 13. Bioluminescence in tissues was examined (after administering the firefly luciferase (fLUC) substrate) to monitor tumor formation (see FIG. 14).

Figure 15:
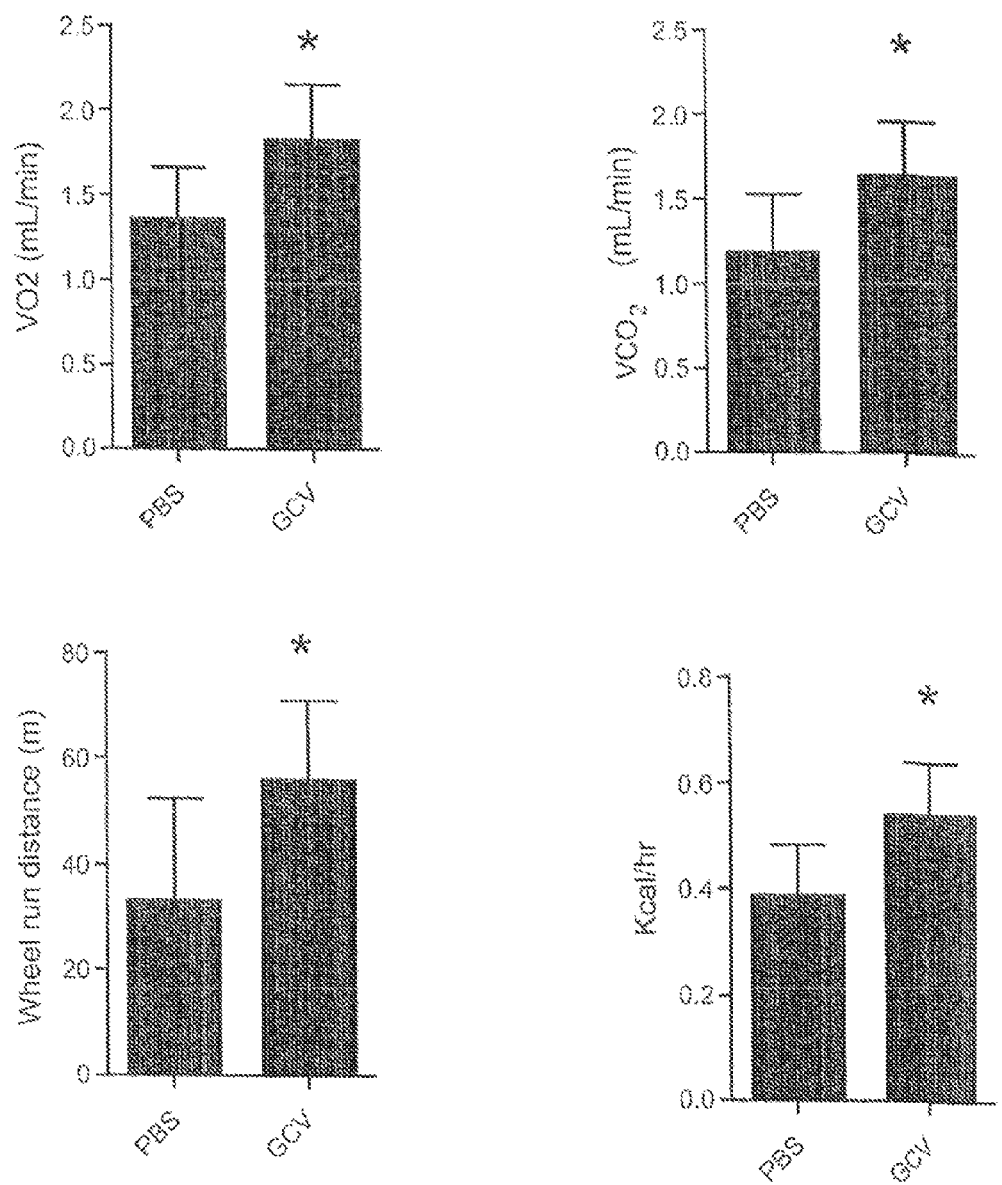
FIG. 15 illustrates metabolic measurements obtained from p16-3MR transgenic mice that were injected with MMTV-PyMT cells and then treated with (1) doxorubicin (DOXO) or (2) doxorubicin and ganciclovir (GCV) as shown in FIG. 13 (top). The measurements were taken 18 days after injection with tumor cells. * indicates $p<0.05$.

Mice were housed in metabolic cages (Promethion, Sable Systems International, Las Vegas, Nev.) for a period of 4 days to monitor food consumption, water consumption, body mass, spontaneous activity and behavior, voluntary exercise, oxygen consumption, and carbon dioxide production. Three days after GCV treatment, animals were monitored for three nights, and the following nocturnal measurements were obtained: $VO_2$ (mL/min); $VCO_2$ (mL/min); food uptake (g); water uptake (g); Kcal/hr; and wheel run distance (m). These data are presented in Table 2 below and in FIG. 15. The data represent the average of the three nocturnal measurements.

TABLE 2

|  | DOXO + PBS | DOXO + GCV |
|---|---|---|
| $VO_2$ (mL/min) | 1.35 ± 0.33 | 1.83 ± 0.34* |
| $VCO_2$ (mL/min) | 1.19 ± 0.35 | 1.63 ± 0.35* |
| Kcal/hr | 0.39 ± 0.1 | 0.54 ± 0.1* |
| Wheel run distance (m) | 3315 ± 1958 | 5588 ± 1552* | p-value: *<0.05; <0.01; *<0.001

Figure 16:
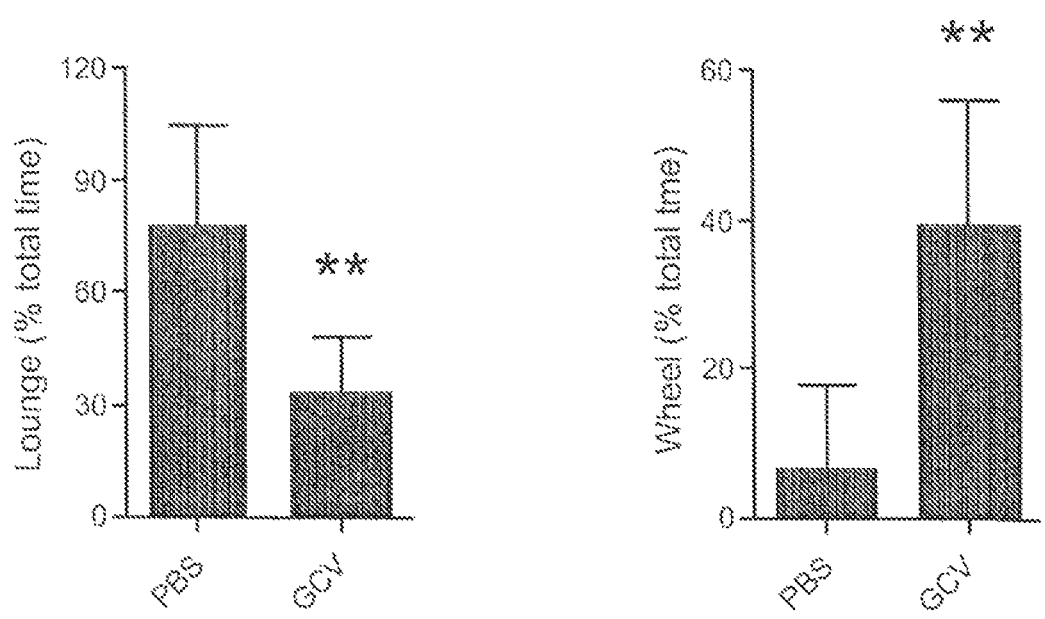
FIG. 16 shows the behavior of the p16-3MR transgenic mice that were injected with MMTV-PyMT cells and then treated with (1) doxorubicin (DOXO) or (2) doxorubicin and ganciclovir (GCV). The measurements were taken 28 days after injection with tumor cells. ** indicates $p<0.01$.

Behavior of animals treated doxorubicin or doxorubicin and GCV was assessed by several criteria accepted in the art as behavior metrics. The metrics and data are presented in Table 3 and in FIG. 16. The animals in the tumor model that were treated with GCV after being treated with doxorubicin exhibited significantly more active behaviors (see interaction with wheel (WHEEL) and long lounge (LLNGE) and short lounge (SLNGE) in Table 3 and FIG. 16).

TABLE 3

|  | DOXO + PBS | DOXO + GCV |
|---|---|---|
| WHEEL | 7.09 ± 10.84 | 39.36 ± 16.77** |
| IHOME | 4.86 ± 12.3 | 14.38 ± 16.62 |
| THOME | 1.16 ± 2.54 | 1.58 ± 0.91 |
| LLNGE | 72.06 ± 24.05 | 23.16 ± 13.68*** |
| SLNGE | 5.34 ± 3.64 | 9.77 ± 2.19* |

WHEEL: Interaction with wheel (>=1 revolution)
IHOME: Entered habitat (stable mass reading)
THOME: Interaction with habitat (no stable mass reading)
LLNGE: Long lounge (>60 sec, no non-XY sensor interactions)
SLNGE: Short lounge (5-60 sec, no non-XY sensor interactions)
p-value: *<0.05; <0.01; *<0.001

To determine if differences in the metabolic data and behavioral data resulted from reduction in tumor size and metastasis that was observed in mice treated with doxorubicin and GCV compared with mice treated with doxorubicin only, an experiment was performed in which mice were not injected with tumor cells. Groups of p16-3MR transgenic mice (5 mice per group) were treated once with doxorubicin (10 mg/kg) or vehicle only as described above. Three days later, GCV was administered 5× daily intraperitoneally at 25 mg/kg, or vehicle only was administered. Three different treatment groups of mice included (1) untreated (NT); (2) doxorubicin, no GCV (DOXO+PBS); (3) doxorubicin and GCV (DOXO+GCV). Mice were housed in metabolic cages for 5-8 days and monitored as described above. The data are presented in Table 4 and Table 5.

TABLE 4

|  | DOXO + PBS | DOXO + GCV | NT |
|---|---|---|---|
| $VO_2$ (mL/min) | 1.14 ± 0.34 | 1.72 ± 0.35* | 1.8 ± 0.29* |
| $VCO_2$ (mL/min) | 1.1 ± 0.36 | 1.71 ± 0.40* | 1.61 ± 0.27* |
| Kcal/hr | 0.34 ± 0.1 | 0.52 ± 0.11* | 0.53 ± 0.09* |
| Wheel run distance (total m) | 2708 ± 1867 | 4627 ± 2486 | 4874 ± 2183 | p-value: *<0.05; <0.01; *<0.001

TABLE 5

|  | DOXO + PBS | DOXO + GCV | NT |
|---|---|---|---|
| WHEEL | 9.58 ± 13.12 | 37.22 ± 14.29* | 36.771 ± 18.13* |
| IHOME | 1.86 ± 1.66 | 2.64 ± 3.34 | 7.026 ± 6.05 |
| THOME | 1.15 ± 1.12 | 1.09 ± 1.58 | 1.91 ± 1.19 |

TABLE 5-continued

|  | DOXO + PBS | DOXO + GCV | NT |
| --- | --- | --- | --- |
| LLNGE | 61.46 ± 18.11 | 37.67 ± 15.81 | 27.53 ± 18.81* |
| SLNGE | 6.94 ± 2.51 | 9.52 ± 2.13 | 11.17 ± 1.96* | p-value: *<0.05; <0.01; *<0.001

Example 7

Senescent Cell Reduction Reduces Likelihood of Side Effects from Senescence Inducing Radiotherapy To examine the role of senescence in contributing to, inducing or increasing the likelihood of side effects resulting from, for example, radiation or chemotherapy used to treat cancer that has already developed. Such side effects may include returning or recurring tumor formation or growth and metastasis. Side effects are monitored in p16-3MR transgenic mice that are either depleted of senescent cells or have senescent cells (naturally developed or induced).

Briefly, tumor cell lines are engineered to express firefly luciferase (fLUC) to enable their detection of tumors and metastases by bioluminescence in a living animal. In particular, a B16-fLUC mouse melanoma cell line and an MMTV-PymT:fLUC mammary carcinoma cell line are generated. The tumor cells are injected into the mice (i.e., B16 into a tail vein; and MMTV-PymT into a mammary fat pad) and small primary tumors are allowed to form over a period of one to four weeks. Then groups of animals are exposed to non-lethal ionizing radiation (IR) or sham-irradiated. Three days after the last irradiation exposure, GCV is administered 5× daily intraperitoneally at 25 mg/kg or vehicle only is administered. Four different treatment groups of mice include (1) no IR (sham irradiated), no GCV; (2) IR, no GCV; (3) no IR, GCV; and (4) IR, GCV. Bioluminescence in tissues is examined (after administering the rLUC substrate) to monitor tumor formation and mouse survival is also monitored. In addition, mice may be housed in metabolic cages for periods of 5-8 days to monitor food consumption, water consumption, body mass, spontaneous activity and behavior, voluntary exercise, oxygen consumption, and carbon dioxide production.

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A mouse from a strain of mice having a transgene inserted in their genome,
   wherein the transgene contains a p16$^{INK4a}$ promoter sequence that controls expression of an enzyme so as to cause the enzyme to be expressed in senescent cells in the mouse,
   wherein the enzyme converts a prodrug to a cytotoxic agent,
   wherein treating the mouse with the prodrug results in the prodrug being converted to the cytotoxic agent by senescent cells, thereby killing the senescent cells but killing less than 10% of non-senescent cells in the mouse,
   wherein the mouse bears a tumor formed from syngeneic cancer cells.

2. The mouse of claim 1, wherein the enzyme is a thymidine kinase.

3. The mouse of claim 1, wherein the prodrug is ganciclovir.

4. The mouse of claim 1, wherein the p16$^{INK4a}$ promoter also controls expression of a luminescent protein so as to cause it to be expressed in senescent cells in the mouse.

5. The mouse of claim 4, wherein the luminescent protein is luciferase.

6. The mouse of claim 1, wherein the p16$^{INK4a}$ promoter also controls expression of a fluorescent protein so as to cause it to be expressed in senescent cells in the mouse.

7. The mouse of claim 6, wherein the fluorescent protein is monomeric red fluorescent protein (mRFP).

8. The mouse of claim 1, wherein the syngeneic cancer cells are melanoma cells.

9. The mouse of claim 1, wherein the syngeneic cancer cells are engineered to express a marker protein so that tumors and metastases can be determined when the mouse is alive.

10. The mouse of claim 9, wherein the marker protein is luciferase.

11. The mouse of claim 1, wherein when the mouse is treated with the prodrug, smaller tumors or fewer metastases form from the injected cancer cells compared with an untreated mouse of the same strain.

12. The mouse of claim 1, wherein when the mouse is treated with the prodrug, there is reduced likelihood of side effects from senescence inducing chemotherapy compared with an untreated mouse of the same strain.

* * * * *

SEQUENCE LISTING

```
<160> NUMBER OF SEQ ID NOS: 25

<210> SEQ ID NO 1
<211> LENGTH: 9267
<212> TYPE: DNA
<213> ORGANISM: Artificial Sequence
<220> FEATURE:
<223> OTHER INFORMATION: pBLUESCRIPT II KS vector containing a p16Ink4a
      promoter-FKBP-caspase-IRES-GFP nucleic acid construct

<400> SEQUENCE: 1
ctaaattgta agcgttaata ttttgttaaa attcgcgtta aattttttgtt aaatcagctc        60 attttttaac caataggccg aaatcggcaa aatcccttat aaatcaaaag aatagaccga       120
gatagggttg agtgttgttc cagtttggaa caagagtcca ctattaaaga acgtggactc       180
caacgtcaaa gggcgaaaaa ccgtctatca gggcgatggc ccactacgtg aaccatcacc       240
ctaatcaagt tttttggggt cgaggtgccg taaagcacta aatcggaacc ctaaagggag       300
cccccgattt agagcttgac ggggaaagcc ggcgaacgtg gcgagaaagg aagggaagaa       360
agcgaaagga cgggcgcta gggcgctggc aagtgtagcg gtcacgctgc gcgtaaccac       420
cacacccgcc gcgcttaatg cgccgctaca gggcgcgtcc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta tagggcgaat tggagctcca       660
ccgcggtggc ggccgctcta gaactagtgg atccgtgtaa agtcactgct tttatagcta       720
catctgcata gatcccctgt atgaaagcat gtactacctg gataataata tctgtatttt       780
```

```
tctgtagtag gaaatcagtg tagtttttaa aaccaaaaag tattgttatt aatctatctt    840
tgatctcaaa caatttcaat gacctagtat agtgatttct acggaaagcc ctgcaattta    900
ctcaaagcag ttttttaaata ttgttttaaa agtgtgtgtg tgtgtgtgtg tgtgtgtgtg    960
tgtgtgtgtg gtgttaaagt cattttcaaa cccctcacaa tgtcttgaat gtgacatttg   1020
agtcatttat ggtaacttat aactcctttg aagaagttat tcagaattga ggttccagac   1080
acacaaatgc acaatacacc attttttcctt ccagttaaca atcagagggc aacacttatt   1140
tttaaggaa aatcgactcc ataagggact ttataaaggg gtagacataa accagtatca   1200
gggataaact ctccgttccc ctgtttaacc taattttccc agggccatcc tggaatacga   1260
attttctctt gaaatacagt caaagaaaaa gtggtaggct acagagcaga ggaaacactg   1320
gacacagcga cccaccccag agtcacttcc cttaatctaa tgactaggtt ttttctgaaa   1380
gttattttgt tagaacacag gaacttttgc gaccacagtg atgctttag agggttgaat   1440
cctcaaaaag aaaattaatc gcaactagta gaagggagat tacttattga ttcttataac   1500
ttctgcagga atacacagtt atgagttagg gcaaagagaa aattgacttt taatattctc   1560
tatcactaac atgagagaac atgtatgtgt tccaaaataa tttttattta ttgaaaaccc   1620
gctatatacc tggattttca cagaatattc attactctcc aaaatggcct tttctaggtg   1680
aatttttattt tccttacaga cctcaagaag tttacataat ttacttaaac ctgaggagag   1740
agaacaaagc ctcagaaaat ttacatagtt tatttaaact aaactcagct tgcttggtag   1800
cagcttctaa tcccagcagt taaagagaca gaagcagggc caacctgggg tataatataa   1860
ggtgagactc tcctttctt ctctctgtct ctgtctgtct ctgtctctgt gtgtgtgtgt   1920
gtgtgtgtgt gtgtgtgtgt gtgtctcctc tctctctctc tctctctctc tctctctctc   1980
tctgtctctc tctccctccc cctccctccc tctcccctc ctctctccct ccctctccct   2040
ccccccccc cacacatttg aattcgtgga gttggtaaat gaggggtcag ttctctgtct   2100
gtctgtagtt ttgtgtccac aggatatgac tgacattctc accacacaca tacaaagtca   2160
aaaatagctg tggccatata aagaatatgg ggagagaaaa ttattcaaaa tctgcagaaa   2220
ataatgccag gcctttaatc ctggcaccca ggaggcagaa gggagacaga gttctgagtt   2280
tatgctgagt tccaggagtg gaagaaaggg ccattgcctt tctggtgagg actgtctttt   2340
taaatcctcc cttctgtcca gtactggtaa ctctgcccaa agcgtgttct tcttcctgcc   2400
tcacaagatt gcaaagacgt ttttaacgaa caatttaaac cggtgcaacg tttatgcgca   2460
gcacaccaac tcatttaaac aaacaacagc cccataaaat agaaatactt tataagcaga   2520
ttgccctccg atgacttcac cccgtcactt ttttatagtt gtgtacagaa tcctagcact   2580
gatacagcaa catcagaaat gtttctgcaa atccttcgca aagattcgga tttcatactg   2640
ggcgtggtac cctccaaaat gagttgtttg agctaggggt gttgggatct cagcttggcg   2700
aagttgtagc tctttcttct gaataaaaga tgacacaatt ttctgctaag atgttaaata   2760
ccttaagttt cagtgtagtg atgaaaatta ccctccttcg ttttttctaat acctgggtgt   2820
tgcactgggg aggaaggaga gatttcgaga aggactagtt cactttctca gaagacacgt   2880
gtgcacttct ttgctgtgcg ggtccagaag gagcccagcg tgtcaaaggg tgaccaggca   2940
tggggagggg gtgttagcgt gggtagcagg cggggggctgt ccgatccttt agcgctgttt   3000
caacgcccag ctctcctcct gaaccctgca tctcttctgt agtccgggct ccatcccttt   3060
cccctccccc atccggaggt gggggggaaca gcagtgtttt caggggtgtt caattcatgc   3120
tatattcagg gcaaatagcg ccacctatgg cgggctgtgg agccaggtca ggagcagagt   3180
```

```
gtggctcccc cccccccca caccatcctc agaggaagga aggagggacc cactggtcac    3240
acgactgggc gattgggcgg gcactgaatc tccgcgagga aagcgaactc gaggagagcc    3300
atcacgcgta gcatggggag tagcaagagc aagcctaagg accccagcca gcgctctaga    3360
ggcgtccaag tcgaaaccat tagtcccggc gatggcagaa catttcctaa aaggggacaa    3420
acatgtgtcg tccattatac aggcatgttg gaggacggca aaaggtgga cagtagtaga    3480 gatcgcaata aacctttcaa attcatgttg ggaaaacaag aagtcattag gggatgggag    3540
gagggcgtgg ctcaaatgtc cgtcggccaa cgcgctaagc tcaccatcag ccccgactac    3600
gcatacggcg ctaccggaca tcccggaatt attcccctc acgctacctt ggtgtttgac    3660
gtcgaactgt tgaagctcga gactagagga gtgcaggtgg agactatctc cccaggagac    3720
gggcgcacct tccccaagcg cggccagacc tgcgtggtgc actacaccgg gatgcttgaa    3780
gatggaaaga agttgattc ctcccgggac agaaacaagc cctttaagtt tatgctaggc    3840
aagcaggagg tgatccgagg ctgggaagaa ggggttgccc agatgagtgt gggtcagaga    3900
gccaaactga ctatatctcc agattatgcc tatggtgcca ctgggcaccc aggcatcatc    3960
ccaccacatg ccactctcgt cttcgatgtg gagcttctaa aactggaaac tagtagtgaa    4020
tcacagactt tggacaaagt ttaccaaatg aaaagcaaac ctcggggata ctgtctgatc    4080
atcaacaatc acaattttgc aaaagcacgg agaaagtgc ccaaacttca cagcattagg    4140
gacaggaatg gaacacactt ggatgcaggg gctttgacca cgacctttga agagcttcat    4200
tttgagatca gccccacga tgactgcaca gtagagcaaa tctatgagat tttgaaaatc    4260
taccaactca tggaccacag taacatggac tgcttcatct gctgtatcct ctcccatgga    4320
gacaagggca tcatctatgg cactgatgga caggaggccc ccatctatga gctgacatct    4380
cagttcactg gtttgaagtg cccttccctt gctggaaaac ccaaagtgtt tttattcag    4440 gcttgtcagg gggataacta ccagaaaggt atacctgttg agactgattc agaggagcaa    4500
ccctatttag aaatggattt atcatcacct caaacgagat atatcccgga tgaggctgac    4560
tttctgctgg ggatggccac tgtgaataac tgtgttcct accgaaaccc tgcagggga    4620 acctggtaca tccagtcact tgccagagc ctgagagagc gatgtcctcg aggcgatgat    4680
attctcacca tcctgactga agtgaactat gaagtaagca acaaggatga caagaaaaac    4740
atggggaaac agatgcctca gcctactttc acactaagaa aaaacttgt cttcccttct    4800 gatgattaca aggatgacga cgataagtga ggatcaacct cgaggaattc acgcgtttaa    4860
ttaactcgag gttttcgagg tcgacggtat cgataagctt gatatcgaat tccgcccctc    4920
tccctccccc cccctaacg ttactggccg aagccgcttg gaataaggcc ggtgtgcgtt    4980
tgtctatatg ttattttcca ccatattgcc gtcttttggc aatgtgaggg cccggaaacc    5040
tggccctgtc ttcttgacga gcattcctag gggtctttcc cctctcgcca aggaatgca    5100 aggtctgttg aatgtcgtga aggaagcagt tcctctggaa gcttcttgaa gacaaacaac    5160
gtctgtagcg acccttgca ggcagcggaa ccccccacct ggcgacaggt gcctctgcgg    5220
ccaaaagcca cgtgtataag atacacctgc aaaggcggca caaccccagt gccacgttgt    5280
gagttggata ttgtggaaa gagtcaaatg gctctcctca gcgtattca acaagggct    5340 gaaggatgcc cagaaggtac cccattgtat gggatctgat ctggggcctc ggtgcacatg    5400
ctttacatgt gtttagtcga ggttaaaaaa acgtctaggc cccccgaacc acggggacgt    5460
ggttttcctt tgaaaaacac gatgataata tggccacaac catggtgagc aagggcgagg    5520
```

```
agctgttcac cggggtggtg cccatcctgg tcgagctgga cggcgacgta aacggccaca    5580
agttcagcgt gtccggcgag ggcgagggcg atgccaccta cggcaagctg accctgaagt    5640
tcatctgcac caccggcaag ctgcccgtgc cctggcccac cctcgtgacc accctgacct    5700
acggcgtgca gtgcttcagc cgctaccccg accacatgaa gcagcacgac ttcttcaagt    5760
ccgccatgcc cgaaggctac gtccaggagc gcaccatctt cttcaaggac gacggcaact    5820
acaagacccg cgccgaggtg aagttcgagg gcgacaccct ggtgaaccgc atcgagctga    5880
agggcatcga cttcaaggag gacggcaaca tcctggggca caagctggag tacaactaca    5940
acagccacaa cgtctatatc atggccgaca agcagaagaa cggcatcaag gtgaacttca    6000
agatccgcca caacatcgag gacggcagcg tgcagctcgc cgaccactac cagcagaaca    6060
cccccatcgg cgacggcccc gtgctgctgc ccgacaacca ctacctgagc acccagtccg    6120
ccctgagcaa agaccccaac gagaagcgcg atcacatggt cctgctggag ttcgtgaccg    6180
ccgccgggat cactctcggc atggacgagc tgtacaagta aagcggccgc gatctttttc    6240
cctctgccaa aaattatggg gacatcatga agccccttga gcatctgact tctggctaat    6300
aaaggaaatt tattttcatt gcaatagtgt gttggaattt tttgtgtctc tcactcggaa    6360
ggacatatgg gagggcaaat catttaaaac atcagaatga gtatttggtt tagagtttgg    6420
caacatatgc catatgctgg ctgccatgaa caaaggtggc tataaagagg tcatcagtat    6480
atgaaacagc cccctgctgt ccattcctta ttccatagaa aagccttgac ttgaggttag    6540 attttttttta tattttgttt tgtgttattt ttttctttaa catccctaaa attttcctta    6600
catgttttac tagccagatt tttcctcctc tcctgactac tcccagtcat agctgtccct    6660
cttctcttat gaagatccct cgacctgcag cccaagcttg gcgtaatcat ggtcatagct    6720
gtttcctgtg tgaaattgtt atccgctcac aattccacac aacatacgag ccggaagcat    6780
aaagtgtaaa gcctggggtg cctaatgagt gagctaactc acattaattg cgttgcgctc    6840
actgcccgct ttccagtcgg gaaacctgtc gtgccagcgg atccgcatct caattagtca    6900
gcaaccatag tcccgcccct aactccgccc atcccgcccc taactccgcc cagttccgcc    6960
cattctccgc cccatggctg actaattttt tttatttatg cagaggccga ggccgcctaa    7020
acggccggcc atcgataccg tcgacctcga ggggggggcc cggtacccagc ttttgttccc    7080 tttagtgagg gttaattgcg cgcttggcgt aatcatggtc atagctgttt cctgtgtgaa    7140
attgttatcc gctcacaatt ccacacaaca tacgagccgg aagcataaag tgtaaagcct    7200
ggggtgccta atgagtgagc taactcacat taattgcgtt gcgctcactg cccgctttcc    7260
agtcgggaaa cctgtcgtgc cagctgcatt aatgaatcgg ccaacgcgcg gggagaggcg    7320
gtttgcgtat tgggcgctct tccgcttcct cgctcactga ctcgctgcgc tcggtcgttc    7380
ggctgcggcg agcggtatca gctcactcaa aggcggtaat acggttatcc acagaatcag    7440
gggataacgc aggaaagaac atgtgagcaa aaggccagca aaaggccagg aaccgtaaaa    7500
aggccgcgtt gctggcgttt ttccataggc tccgccccc tgacgagcat cacaaaaatc    7560
gacgctcaag tcagaggtgg cgaaacccga caggactata aagataccag gcgtttcccc    7620
ctggaagctc cctcgtgcgc tctcctgttc cgaccctgcc gcttaccgga tacctgtccg    7680
cctttctccc ttcgggaagc gtggcgcttt ctcatagctc acgctgtagg tatctcagtt    7740
cggtgtaggt cgttcgctcc aagctgggct gtgtgcacga accccccgtt cagcccgacc    7800
gctgcgcctt atccggtaac tatcgtcttg agtccaaccc ggtaagacac gacttatcgc    7860
cactggcagc agccactggt aacaggatta gcagagcgag gtatgtaggc ggtgctacag    7920
```

```
agttcttgaa gtggtggcct aactacggct acactagaag gacagtattt ggtatctgcg      7980
ctctgctgaa gccagttacc ttcggaaaaa gagttggtag ctcttgatcc ggcaaacaaa      8040
ccaccgctgg tagcggtggt ttttttgttt gcaagcagca gattacgcgc agaaaaaaag      8100
gatctcaaga agatcctttg atcttttcta cggggtctga cgctcagtgg aacgaaaact      8160
cacgttaagg gattttggtc atgagattat caaaaaggat cttcacctag atccttttaa      8220
attaaaaatg aagttttaaa tcaatctaaa gtatatatga gtaaacttgg tctgacagtt      8280
accaatgctt aatcagtgag gcacctatct cagcgatctg tctatttcgt tcatccatag      8340
ttgcctgact ccccgtcgtg tagataacta cgatacggga gggcttacca tctggcccca      8400
gtgctgcaat gataccgcga gacccacgct caccggctcc agatttatca gcaataaacc      8460
agccagccgg aagggccgag cgcagaagtg gtcctgcaac tttatccgcc tccatccagt      8520
ctattaattg ttgccgggaa gctagagtaa gtagttcgcc agttaatagt ttgcgcaacg      8580
ttgttgccat tgctacaggc atcgtggtgt cacgctcgtc gtttggtatg gcttcattca      8640
gctccggttc ccaacgatca aggcgagtta catgatcccc catgttgtgc aaaaaagcgg      8700
ttagctcctt cggtcctccg atcgttgtca gaagtaagtt ggccgcagtg ttatcactca      8760
tggttatggc agcactgcat aattctctta ctgtcatgcc atccgtaaga tgcttttctg      8820
tgactggtga gtactcaacc aagtcattct gagaatagtg tatgcggcga ccgagttgct      8880
cttgcccggc gtcaatacgg gataataccg cgccacatag cagaacttta aaagtgctca      8940
tcattggaaa acgttcttcg gggcgaaaac tctcaaggat cttaccgctg ttgagatcca      9000
gttcgatgta acccactcgt gcacccaact gatcttcagc atcttttact ttcaccagcg      9060
tttctgggtg agcaaaaaca ggaaggcaaa atgccgcaaa aaagggaata agggcgacac      9120
ggaaatgttg aatactcata ctcttccttt ttcaatatta ttgaagcatt tatcagggtt      9180
attgtctcat gagcggatac atatttgaat gtatttagaa aaataaacaa atagggggttc     9240 cgcgcacatt tccccgaaaa gtgccac                                          9267

<210> SEQ ID NO 2
<211> LENGTH: 134
<212> TYPE: DNA
<213> ORGANISM: Artificial Sequence
<220> FEATURE:
<223> OTHER INFORMATION: 5 prime terminal synthetic vector sequence

<400> SEQUENCE: 2
ctaaattgta agcgttaata ttttgttaaa attcgcgtta aatttttgtt aaatcagctc        60
attttttaac caataggccg aaatcggcaa aatcccttat aaatcaaaag aatagaccga      120
gatagggttg agtg                                                        134

<210> SEQ ID NO 3
<211> LENGTH: 325
<212> TYPE: DNA
<213> ORGANISM: Artificial Sequence
<220> FEATURE:
<223> OTHER INFORMATION: F1 ori synthetic nucleotide sequence

<400> SEQUENCE: 3
ttgttccagt ttggaacaag agtccactat taaagaacgt ggactccaac gtcaaagggc        60
gaaaaaccgt ctatcagggc gatggcccac tacgtgaacc atcaccctaa tcaagttttt      120
tggggtcgag gtgccgtaaa gcactaaatc ggaaccctaa agggagcccc cgatttagag      180
```

-continued

```
cttgacgggg aaagccggcg aacgtggcga gaaaggaagg gaagaaagcg aaaggagcgg      240
gcgctagggc gctggcaagt gtagcggtca cgctgcgcgt aaccaccaca cccgccgcgc      300
ttaatgcgcc gctacagggc gcgtc                                            325

<210> SEQ ID NO 4
<211> LENGTH: 139
<212> TYPE: DNA
<213> ORGANISM: Artificial Sequence
<220> FEATURE:
<223> OTHER INFORMATION: LacZ alpha synthetic nucleotide sequence

<400> SEQUENCE: 4
ccattcgcca ttcaggctgc gcaactgttg ggaagggcga tcggtgcggg cctcttcgct       60
attacgccag ctggcgaaag ggggatgtgc tgcaaggcga ttaagttggg taacgccagg     120
gttttcccag tcacgacgt                                                   139

<210> SEQ ID NO 5
<211> LENGTH: 26
<212> TYPE: DNA
<213> ORGANISM: Artificial Sequence
<220> FEATURE:
<223> OTHER INFORMATION: M13 fwd synthetic nucleotide sequence

<400> SEQUENCE: 5
tgtaaaacga cggccagtga gcgcgc                                            26

<210> SEQ ID NO 6
<211> LENGTH: 65
<212> TYPE: DNA
<213> ORGANISM: Artificial Sequence
<220> FEATURE:
<223> OTHER INFORMATION: T7 synthetic nucleotide sequence

<400> SEQUENCE: 6
gtaatacgac tcactatagg gcgaattgga gctccaccgc ggtggcggcc gctctagaac       60
tagtg                                                                   65

<210> SEQ ID NO 7
<211> LENGTH: 5
<212> TYPE: DNA
<213> ORGANISM: Artificial Sequence
<220> FEATURE:
<223> OTHER INFORMATION: p16 synthetic promoter sequence

<400> SEQUENCE: 7 gatcc                                                                    5

<210> SEQ ID NO 8
<211> LENGTH: 13
<212> TYPE: DNA
<213> ORGANISM: Artificial Sequence
<220> FEATURE:
<223> OTHER INFORMATION: p16 synthetic promoter sequence

<400> SEQUENCE: 8
gtgtaaagtc act                                                          13

<210> SEQ ID NO 9
<211> LENGTH: 2604
<212> TYPE: DNA
<213> ORGANISM: Artificial Sequence
<220> FEATURE:
<223> OTHER INFORMATION: p16 synthetic promoter sequence
```

<400> SEQUENCE: 9

```
cttttatagc tacatctgca tagatcccct gtatgaaagc atgtactacc tggataataa    60
tatctgtatt tttctgtagt aggaaatcag tgtagttttt aaaaccaaaa agtattgtta   120
ttaatctatc tttgatctca aacaatttca atgacctagt atagtgattt ctacggaaag   180
ccctgcaatt tactcaaagc agttttaaa tattgtttta aaagtgtgtg tgtgtgtgtg    240
tgtgtgtgtg tgtgtgtgtg tggtgttaaa gtcattttca aacccctcac aatgtcttga   300
atgtgacatt tgagtcattt atggtaactt ataactcctt tgaagaagtt attcagaatt   360
gaggttccag acacacaaat gcacaataca ccattttttcc ttccagttaa caatcagagg   420
gcaacactta tttttaaagg aaaatcgact ccataaggga ctttataaag gggtagacat   480
aaaccagtat cagggataaa ctctccgttc ccctgtttaa cctaattttc cagggccat    540
cctggaatac gaattttctc ttgaaataca gtcaaagaaa aagtggtagg ctacagagca   600
gaggaaacac tggacacagc gacccacccc agagtcactt cccttaatct aatgactagg   660
ttttttctga aagttatttt gttagaacac aggaactttt gcgaccacag tgatgctttt   720
agagggttga atcctcaaaa agaaaattaa tcgcaactag tagaagggag attacttatt   780
gattcttata acttctgcag gaatacacag ttatgagtta gggcaaagag aaaattgact   840
tttaatattc tctatcacta acatgagaga acatgtatgt gttccaaaat aattttttatt  900
tattgaaaac ccgctatata cctggatttt cacagaatat tcattactct ccaaaatggc   960
cttttctagg tgaatttat tttccttaca gacctcaaga agtttacata atttacttaa   1020
acctgaggag agagaacaaa gcctcagaaa atttacatag tttatttaaa ctaaactcag  1080
cttgcttggt agcagcttct aatcccagca gttaaagaga cagaagcagg gccaacctgg  1140
ggtataatat aaggtgagac tctcctttct ttctctctgt ctctgtctgt ctctgtctct  1200
gtgtgtgtgt gtgtgtgtgt gtgtgtgtgt gtgtgtctcc tctctctctc tctctctctc  1260
tctctctctc tctctgtctc tctctcccct cccctccctc cctctccccc tcctctctcc  1320
ctccctctcc ctcccccccc cccacacatt tgaattcgtg gagttggtaa atgaggggtc  1380
agttctctgt ctgtctgtag ttttgtgtcc acaggatatg actgacattc tcaccacaca  1440
catacaaagt caaaaatagc tgtggccata taaagaatat ggggagagaa aattattcaa  1500
aatctgcaga aaataatgcc aggcctttaa tcctggcacc caggaggcag aagggagaca  1560
gagttctgag tttatgctga gttccaggag tggaagaaag ggccattgcc tttctggtga  1620
ggactgtctt tttaaatcct cccttctgtc cagtactggt aactctgccc aaagcgtgtt  1680
cttcttcctg cctcacaaga ttgcaaagac gttttttaacg aacaatttaa accggtgcaa  1740
cgtttatgcg cagcacacca actcatttaa acaaacaaca gccccataaa atagaaaatac  1800
tttataagca gattgccctc cgatgacttc accccgtcac ttttttatag ttgtgtacag  1860
aatcctagca ctgatacagc aacatcagaa atgtttctgc aaatccttcg caaagattcg  1920
gatttcatac tgggcgtggt accctccaaa atgagttgtt tgagctaggg ttgttgggat  1980
ctcagcttgg cgaagttgta gctctttctt ctgaataaaa gatgacacaa ttttctgcta  2040
agatgttaaa taccttaagt ttcagtgtag tgatgaaaat taccctcctt cgttttttcta  2100
atacctgggt gttgcactgg ggaggaagga gagatttcga gaaggactag ttcactttct  2160
cagaagacac gtgtgcactt cttttgctgtg cgggtccaga aggagcccag cgtgtcaaag  2220
ggtgaccagg catgggggag gggtgttagc gtgggtagca ggcgggggct gtccgatcct  2280
```

| | |
|---|---|
| ttagcgctgt tcaacgccc agctctcctc ctgaaccctg catctcttct gtagtccggg | 2340 |
| ctccatccct ttcccctccc ccatccggag gtgggggggaa cagcagtgtt ttcagggggtg | 2400 |
| ttcaattcat gctatattca gggcaaatag cgccacctat ggcgggctgt ggagccaggt | 2460 |
| caggagcaga gtgtggctcc cccccccccc cacaccatcc tcagaggaag gaaggaggga | 2520 |
| cccactggtc acacgactgg gcgattgggc gggcactgaa tctccgcgag gaaagcgaac | 2580 |
| tcgaggagag ccatcacgcg tagc | 2604 |

<210> SEQ ID NO 10
<211> LENGTH: 702
<212> TYPE: DNA
<213> ORGANISM: Artificial Sequence
<220> FEATURE:
<223> OTHER INFORMATION: FKBP synthetic nucleotide sequence

<400> SEQUENCE: 10

| | |
|---|---|
| atggggagta gcaagagcaa gcctaaggac cccagccagc gctctagagg cgtccaagtc | 60 |
| gaaaccatta gtcccggcga tggcagaaca tttcctaaaa ggggacaaac atgtgtcgtc | 120 |
| cattatacag gcatgttgga ggacggcaaa aaggtggaca gtagtagaga tcgcaataaa | 180 |
| cctttcaaat tcatgttggg aaaacaagaa gtcattaggg gatgggagga gggcgtggct | 240 |
| caaatgtccg tcggccaacg cgctaagctc accatcagcc ccgactacgc atacggcgct | 300 |
| accggacatc ccggaattat tccccctcac gctaccttgg tgtttgacgt cgaactgttg | 360 |
| aagctcgaga ctagaggagt gcaggtggag actatctccc aggagacgg gcgcaccttc | 420 |
| cccaagcgcg gccagacctg cgtggtgcac tacaccggga tgcttgaaga tggaaagaaa | 480 |
| gttgattcct cccgggacag aaacaagccc tttaagttta tgctaggcaa gcaggaggtg | 540 |
| atccgaggct gggaagaagg ggttgcccag atgagtgtgg gtcagagagc caaactgact | 600 |
| atatctccag attatgccta tggtgccact gggcacccag gcatcatccc accacatgcc | 660 |
| actctcgtct tcgatgtgga gcttctaaaa ctggaaacta gt | 702 |

<210> SEQ ID NO 11
<211> LENGTH: 789
<212> TYPE: DNA
<213> ORGANISM: Artificial Sequence
<220> FEATURE:
<223> OTHER INFORMATION: Casp8 synthetic nucleotide sequence

<400> SEQUENCE: 11

| | |
|---|---|
| agtgaatcac agactttgga caaagtttac caaatgaaaa gcaaacctcg gggatactgt | 60 |
| ctgatcatca acaatcacaa ttttgcaaaa gcacgggaga agtgcccaa acttcacagc | 120 |
| attagggaca ggaatggaac acacttggat cagggggctt tgaccacgac ctttgaagag | 180 |
| cttcattttg agatcaagcc ccacgatgac tgcacagtag agcaaatcta tgagattttg | 240 |
| aaaatctacc aactcatgga ccacagtaac atggactgct tcatctgctg tatcctctcc | 300 |
| catggagaca aagggcatca tctatggcact gatggacagg aggcccccat ctatgagctg | 360 |
| acatctcagt tcactggttt gaagtgccct tcccttgctg gaaaacccaa agtgtttttt | 420 |
| attcaggctt gtcagggga taactaccag aaaggtatac ctgttgagac tgattcagag | 480 |
| gagcaaccct atttagaaat ggatttatca tcacctcaaa cgagatatat cccggatgag | 540 |
| gctgactttc tgctggggat ggccactgtg aataactgtg tttcctaccg aaaccctgca | 600 |
| gagggaacct ggtacatcca gtcactttgc agagcctga gagcgatg tcctcgaggc | 660 |
| gatgatattc tcaccatcct gactgaagtg aactatgaag taagcaacaa ggatgacaag | 720 |

```
aaaaacatgg ggaaacagat gcctcagcct actttcacac taagaaaaaa acttgtcttc    780
ccttctgat                                                            789

<210> SEQ ID NO 12
<211> LENGTH: 27
<212> TYPE: DNA
<213> ORGANISM: Artificial Sequence
<220> FEATURE:
<223> OTHER INFORMATION: Flag synthetic nucleotide sequence

<400> SEQUENCE: 12
gattacaagg atgacgacga taagtga                                         27

<210> SEQ ID NO 13
<211> LENGTH: 5
<212> TYPE: DNA
<213> ORGANISM: Artificial Sequence
<220> FEATURE:
<223> OTHER INFORMATION: 3 prime UTR synthetic nucleotide sequence

<400> SEQUENCE: 13 ggatc                                                                  5

<210> SEQ ID NO 14
<211> LENGTH: 39
<212> TYPE: DNA
<213> ORGANISM: Artificial Sequence
<220> FEATURE:
<223> OTHER INFORMATION: Multiple cloning site synthetic nucleotide
      sequence

<400> SEQUENCE: 14
aacctcgagg aattcacgcg tttaattaac tcgaggttt                             39

<210> SEQ ID NO 15
<211> LENGTH: 1268
<212> TYPE: DNA
<213> ORGANISM: Artificial Sequence
<220> FEATURE:
<223> OTHER INFORMATION: IRES GFP synthetic nucleotide sequence

<400> SEQUENCE: 15
tcgaggtcga cggtatcgat aagcttgata tcgaattccg ccccctctccc tccccccccc    60 ctaacgttac tggccgaagc cgcttggaat aaggccggtg tgcgtttgtc tatatgttat    120
tttccaccat attgccgtct tttggcaatg tgagggcccg gaaacctggc cctgtcttct    180
tgacgagcat tcctaggggt cttttccctc tcgccaaagg aatgcaaggt ctgttgaatg    240
tcgtgaagga agcagttcct ctggaagctt cttgaagaca acaacgtct gtagcgaccc    300 tttgcaggca gcggaacccc ccacctggcg acaggtgcct ctgcggccaa aagccacgtg    360
tataagatac acctgcaaag gcggcacaac cccagtgcca cgttgtgagt tggatagttg    420
tggaaagagt caaatggctc tcctcaagcg tattcaacaa ggggctgaag gatgcccaga    480
aggtacccca ttgtatggga tctgatctgg ggcctcggtg cacatgcttt acatgtgttt    540
agtcgaggtt aaaaaaacgt ctaggccccc cgaaccacgg ggacgtggtt ttcctttgaa    600
aaacacgatg ataatatggc cacaaccatg gtgagcaagg gcgaggagct gttcaccggg    660
gtggtgccca tcctggtcga gctggacggc gacgtaaacg gccacaagtt cagcgtgtcc    720
ggcgagggcg agggcgatgc cacctacggc aagctgaccc tgaagttcat ctgcaccacc    780
ggcaagctgc ccgtgccctg gcccaccctc gtgaccaccc tgacctacgg cgtgcagtgc    840
```

```
ttcagccgct accccgacca catgaagcag cacgacttct tcaagtccgc catgcccgaa        900
ggctacgtcc aggagcgcac catcttcttc aaggacgacg gcaactacaa gacccgcgcc        960
gaggtgaagt tcgagggcga caccctggtg aaccgcatcg agctgaaggg catcgacttc       1020
aaggaggacg gcaacatcct ggggcacaag ctggagtaca actacaacag ccacaacgtc       1080
tatatcatgg ccgacaagca gaagaacggc atcaaggtga acttcaagat ccgccacaac       1140
atcgaggacg gcagcgtgca gctcgccgac cactaccagc agaacacccc catcggcgac       1200
ggccccgtgc tgctgcccga caaccactac ctgagcaccc agtccgccct gagcaaagac       1260
cccaacga                                                                1268
```

<210> SEQ ID NO 16
<211> LENGTH: 565
<212> TYPE: DNA
<213> ORGANISM: Artificial Sequence
<220> FEATURE:
<223> OTHER INFORMATION: Rabbit B-globin PA synthetic nucleotide
      sequence

<400> SEQUENCE: 16

```
gaagcgcgat cacatggtcc tgctggagtt cgtgaccgcc gccgggatca ctctcggcat         60
ggacgagctg tacaagtaaa gcggccgcga tcttttttccc tctgccaaaa attatgggga       120
catcatgaag ccccttgagc atctgacttc tggctaataa aggaaattta ttttcattgc       180
aatagtgtgt tggaattttt tgtgtctctc actcggaagg acatatggga gggcaaatca       240
tttaaaacat cagaatgagt atttggttta gagtttggca acatatgcca tatgctggct       300
gccatgaaca aggtggcta taaagaggtc atcagtatat gaaacagccc cctgctgtcc       360
attccttatt ccatagaaaa gccttgactt gaggttagat ttttttttata ttttgttttg       420 tgttattttt ttctttaaca tccctaaaat tttccttaca tgttttacta gccagatttt       480
tcctcctctc ctgactactc ccagtcatag ctgtccctct tctcttatga agatccctcg       540
acctgcagcc caagcttggc gtaat                                             565
```

<210> SEQ ID NO 17
<211> LENGTH: 26
<212> TYPE: DNA
<213> ORGANISM: Artificial Sequence
<220> FEATURE:
<223> OTHER INFORMATION: M13-rev synthetic nucleotide sequence

<400> SEQUENCE: 17

```
catggtcata gctgtttcct gtgtga                                             26
```

<210> SEQ ID NO 18
<211> LENGTH: 285
<212> TYPE: DNA
<213> ORGANISM: Artificial Sequence
<220> FEATURE:
<223> OTHER INFORMATION: LacO synthetic nucleotide sequence

<400> SEQUENCE: 18

```
aattgttatc cgctcacaat tccacacaac atacgagccg aagcataaa gtgtaaagcc         60 tggggtgcct aatgagtgag ctaactcaca ttaattgcgt tgcgctcact gcccgctttc       120
cagtcgggaa acctgtcgtg ccagcggatc cgcatctcaa ttagtcagca accatagtcc       180
cgcccctaac tccgcccatc ccgcccctaa ctccgcccag ttccgcccat tctccgcccc       240
atggctgact aattttttttt atttatgcag aggccgaggc cgcct                      285
```

<210> SEQ ID NO 19
<211> LENGTH: 58
<212> TYPE: DNA
<213> ORGANISM: Artificial Sequence
<220> FEATURE:
<223> OTHER INFORMATION: Fse1 linker synthetic nucleotide sequence

<400> SEQUENCE: 19
aaacggccgg ccatcgatac cgtcgacctc gagggggggc cggtaccca gcttttgt       58

<210> SEQ ID NO 20
<211> LENGTH: 37
<212> TYPE: DNA
<213> ORGANISM: Artificial Sequence
<220> FEATURE:
<223> OTHER INFORMATION: T3 synthetic nucleotide sequence

<400> SEQUENCE: 20
tccctttagt gagggttaat tgcgcgcttg gcgtaat                              37

<210> SEQ ID NO 21
<211> LENGTH: 26
<212> TYPE: DNA
<213> ORGANISM: Artificial Sequence
<220> FEATURE:
<223> OTHER INFORMATION: M13-rev synthetic nucleotide sequence

<400> SEQUENCE: 21
catggtcata gctgtttcct gtgtga                                         26

<210> SEQ ID NO 22
<211> LENGTH: 362
<212> TYPE: DNA
<213> ORGANISM: Artificial Sequence
<220> FEATURE:
<223> OTHER INFORMATION: LacO synthetic nucleotide sequence

<400> SEQUENCE: 22
aattgttatc cgctcacaat tccacacaac atacgagccg gaagcataaa gtgtaaagcc    60
tggggtgcct aatgagtgag ctaactcaca ttaattgcgt tgcgctcact gcccgctttc   120
cagtcgggaa acctgtcgtg ccagctgcat taatgaatcg gccaacgcgc ggggagaggc   180
ggtttgcgta ttgggcgctc ttccgcttcc tcgctcactg actcgctgcg ctcggtcgtt   240
cggctgcggc gagcggtatc agctcactca aaggcggtaa tacggttatc cacagaatca   300
ggggataacg caggaaagaa catgtgagca aaaggccagc aaaaggccag gaaccgtaaa   360
aa                                                                  362

<210> SEQ ID NO 23
<211> LENGTH: 780
<212> TYPE: DNA
<213> ORGANISM: Artificial Sequence
<220> FEATURE:
<223> OTHER INFORMATION: ColE1 origin synthetic nucleotide sequence

<400> SEQUENCE: 23
ggccgcgttg ctggcgtttt tccataggct ccgcccccct gacgagcatc acaaaaatcg    60
acgctcaagt cagaggtggc gaaacccgac aggactataa agataccagg cgtttccccc   120
tggaagctcc ctcgtgcgct ctcctgttcc gaccctgccg cttaccggat acctgtccgc   180
ctttctccct tcgggaagcg tggcgctttc tcatagctca cgctgtaggt atctcagttc   240

```
ggtgtaggtc gttcgctcca agctgggctg tgtgcacgaa ccccccgttc agcccgaccg    300
ctgcgcctta tccggtaact atcgtcttga gtccaacccg gtaagacacg acttatcgcc    360
actggcagca gccactggta acaggattag cagagcgagg tatgtaggcg gtgctacaga    420
gttcttgaag tggtggccta actacggcta cactagaagg acagtatttg gtatctgcgc    480
tctgctgaag ccagttacct tcggaaaaag agttggtagc tcttgatccg gcaaacaaac    540
caccgctggt agcggtggtt ttttgtttg caagcagcag attacgcgca gaaaaaaagg    600
atctcaagaa gatcctttga tcttttctac ggggtctgac gctcagtgga acgaaaactc    660
acgttaaggg attttggtca tgagattatc aaaaaggatc ttcacctaga tccttttaaa    720
ttaaaaatga agttttaaat caatctaaag tatatatgag taaacttggt ctgacagtta    780
```

<210> SEQ ID NO 24
<211> LENGTH: 986
<212> TYPE: DNA
<213> ORGANISM: Artificial Sequence
<220> FEATURE:
<223> OTHER INFORMATION: AmpR synthetic nucleotide sequence

<400> SEQUENCE: 24

```
ccaatgctta atcagtgagg cacctatctc agcgatctgt ctatttcgtt catccatagt     60
tgcctgactc cccgtcgtgt agataactac gatacgggag ggcttaccat ctggccccag    120
tgctgcaatg ataccgcgag acccacgctc accggctcca gatttatcag caataaacca    180
gccagccgga agggccgagc gcagaagtgg tcctgcaact ttatccgcct ccatccagtc    240
tattaattgt tgccgggaag ctagagtaag tagttcgcca gttaatagtt tgcgcaacgt    300
tgttgccatt gctacaggca tcgtggtgtc acgctcgtcg tttggtatgg cttcattcag    360
ctccggttcc caacgatcaa ggcgagttac atgatccccc atgttgtgca aaaaagcggt    420
tagctccttc ggtcctccga tcgttgtcag aagtaagttg gccgcagtgt tatcactcat    480
ggttatggca gcactgcata attctcttac tgtcatgcca tccgtaagat gcttttctgt    540
gactggtgag tactcaacca agtcattctg agaatagtgt atgcggcgac cgagttgctc    600
ttgcccggcg tcaatacggg ataataccgc gccacatagc agaactttaa aagtgctcat    660
cattggaaaa cgttcttcgg ggcgaaaact ctcaaggatc ttaccgctgt tgagatccag    720
ttcgatgtaa cccactcgtg cacccaactg atcttcagca tcttttactt tcaccagcgt    780
ttctgggtga gcaaaaacag gaaggcaaaa tgccgcaaaa aagggaataa gggcgacacg    840
gaaatgttga atactcatac tcttcctttt tcaatattat tgaagcattt atcagggtta    900
ttgtctcatg agcggataca tatttgaatg tatttagaaa aataaacaaa tagggggttcc    960 gcgcacattt ccccgaaaag tgccac                                          986
```

<210> SEQ ID NO 25
<211> LENGTH: 2664
<212> TYPE: DNA
<213> ORGANISM: Artificial Sequence
<220> FEATURE:
<223> OTHER INFORMATION: p16-3MR synthetic transgene nucleotide sequence

<400> SEQUENCE: 25

```
atggcttcca aggtgtacga ccccgagcaa cgcaaacgca tgatcactgg gcctcagtgg     60
tgggctcgct gcaagcaaat gaacgtgctg gactccttca tcaactacta tgattccgag    120
aagcacgccg agaacgccgt gatttttctg catggtaacg ctgcctccag ctacctgtgg    180
aggcacgtcg tgcctcacat cgagcccgtg gctagatgca tcatccctga tctgatcgga    240
```

```
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tgggggcctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt catcgagtc cgaccctggg     780 ttcttttcca cgctattgt cgagggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cagctcgaga attctcacgc gtctgcagga    960
tatcaagctt ccaccatggc ctcctccgag gacgtcatca agttcatgcg cttcaaggtg   1020
cgcatggagg gctccgtgaa cggccacgag ttcgagatcg agggcgaggg cgagggccgc   1080
ccctacgagg gcacccagac cgccaagctg aaggtgacca agggcggccc cctgcccttc   1140
gcctgggaca tcctgtcccc tcagttccag tacggctcca aggcctacgt gaagcacccc   1200
gccgacatcc ccgactactt gaagctgtcc ttccccgagg gcttcaagtg ggagcgcgtg   1260
atgaacttcg aggacggcgg cgtggtgacc gtgacccagg actcctccct gcaggacggc   1320
gagttcatct acaaggtgaa gctgcgcggc accaacttcc cctccgacgg ccccgtaatg   1380
cagaagaaga ccatgggctg ggaggcctcc accgagagga tgtaccccga ggacggcgcc   1440
ctgaagggcg agatcaagat gaggctgaag ctgaaggacg gcggccacta cgacgccgag   1500
gtcaagacca cctacatggc caagaagccc gtgcagctgc ccggcgccta caagaccgac   1560
atcaagctgg acatcaccct ccacaacgag gactaccaca tcgtggaaca gtacgagcgc   1620
gccgagggcc gccactccac cggcgccacc gcgggcccgg gatccgccac catgcccacg   1680
ctactgcggg tttatataga cggtccccac gggatgggga aaaccaccac caccacgcaa   1740
ctgctggtgg ccctgggttc gcgcgacgat atcgtctacg tacccgagcc gatgacttac   1800
tggcgggtgc tggggcttc cgagacaatc gcgaacatct acaccacaca acaccgcctc   1860
gaccagggtg agatatcggc cggggacgcg gcggtggtaa tgacaagcgc ccagataaca   1920 atgcctatg ccgtgaccga cgccgttctg gctcctcata tcggggggga ggctgggagc    1980
tcacatgccc cgcccccggc cctcaccatc ttcctcgacc gccatcccat cgccttcatg   2040
ctgtgctacc cggccgcgcg gtaccttatg gcagcatga ccccccaggc cgtgctggcg     2100
ttcgtggccc tcatcccgcc gaccttgccc ggcaccaaca tcgtgcttgg ggcccttccg   2160
gaggacagac acatcgaccg cctggccaaa cgccagcgcc ccggcgagcg ctggacctg     2220 gctatgctgg ctgcgattcg ccgcgtttac gggctacttg ccaatacggt gcggtatctg   2280
cagtgcggcg ggtcgtggcg ggaggactgg ggacagcttt cggggacggc cgtgccgccc   2340
cagggtgccg agcccagag caacgcgggc ccacgcacccc atatcgggga cacgttattt    2400
accctgtttc gggccccga gttgatggcc cccaacggcg acctgtataa cgtgtttgcc   2460
tgggccttgg acgtcttggc caaacgcctc cgttccatgc acgtctttat cctggattac   2520
gaccaatcgc ccgccggctg ccgggacgcc ctgctgcaac ttacctccgg gatggtccag   2580
```

-continued

```
acccacgtca ccaccccgg ctccataccg acgatatgcg acctggcgcg cacgtttgcc    2640
cgggagatgg gggaggctaa ctga                                          2664
```